(12) United States Patent
Undheim et al.

(10) Patent No.: US 8,153,609 B2
(45) Date of Patent: Apr. 10, 2012

(54) PURINE NUCLEOTIDE DERIVATIVES

(75) Inventors: Kjell Undheim, Olso (NO); Kjetil Taskén, Oslo (NO); Jo Klaveness, Oslo (NO); Geir Langli, Oslo (NO); Vidar Bjørnstad, Olso (NO)

(73) Assignee: Lauras AS, Olso (NO)

( * ) Notice: Subject to any disclaimer, the term of this patent is extended or adjusted under 35 U.S.C. 154(b) by 897 days.

(21) Appl. No.: 11/629,908

(22) PCT Filed: Jun. 20, 2005

(86) PCT No.: PCT/GB2005/002418
§ 371 (c)(1),
(2), (4) Date: Jan. 15, 2008

(87) PCT Pub. No.: WO2005/123755
PCT Pub. Date: Dec. 29, 2005

(65) Prior Publication Data
US 2008/0293665 A1 Nov. 27, 2008

(30) Foreign Application Priority Data
Jun. 18, 2004 (GB) .................................. 0413726.1

(51) Int. Cl.
*A01N 43/04* (2006.01)
*A61K 31/70* (2006.01)
*C07H 19/20* (2006.01)
*G01N 33/00* (2006.01)
(52) U.S. Cl. .......................... 514/47; 536/26.13; 436/94
(58) Field of Classification Search .................. None
See application file for complete search history.

(56) References Cited

U.S. PATENT DOCUMENTS

| 3,968,101 A | 7/1976 | Christensen et al. |
| 5,625,056 A | 4/1997 | Genieser |
| 5,843,916 A | 12/1998 | Cho-Chung |

FOREIGN PATENT DOCUMENTS

| WO | WO 89/07108 A | 8/1989 |
| WO | WO 93/21929 | 11/1993 |
| WO | WO 98/48809 | 11/1998 |
| WO | WO 03/104250 | 12/2003 |

OTHER PUBLICATIONS

Tian, et al. Progress in Natural Science, 4(6), 726-31, 1992.*
Eckstein et al, *Biochemistry*, 13(18):3806-3810 (1974).
Baraniak et al, *J.C.S. Chem. Comm.*, pp. 940-941 (1979).
Barniak et al, *J.C.S. Chem. Comm.*, 1:1645-1656 (1987).
Vroom et al, *Rec. Trav. Chim., Pays-Bas*, 106:577-580 (1987).
Chirstensen et al, *J. Biol. Chem.*, 278:35394-35402 (2003).
Gjertsen et al, *Am. Soc. Biochem. Mol. Biol.*, 270:20599-20607 (1995).
Dostmann et al, *J. Biol. Chem.*, 265:10484-10491 (1990).
Otmakhov et al, *Neurophysiol*, 87:3018-3032 (2002).
Genieser et al, *Tetrahedron Lett.*, 29:2803-2804 (1988).
Eckstein et al, *Tetrahedron Lett.*, 27:1657-1660 (1986).
Bentrude et al, *Synthesis*, pp. 27-29 (1984).
Rottländer et al, *Chem. Eur. J.*, 6:767-770 (2000).
Stec, *Acc. Chem. Res.*, 16:411-417 (1983).
Beres et al, *J. Org. Chem.*, 50:1271-1278 (1985).
Stec et al, *J. Org. Chem.*, 41:227-233 (1976).
Cooper et al, *Chem. Soc., Perkin Trans.*, 1:1969-1980 (1977).
Tian et al, *Progress in Natural Science*, 4(6):726-731 (1994).
Gjertsen et al, *J. Biol. Chem.*, 270:20599-20607 (1995).
Clayden, J. et al., "Organic Chemistry", Oxford University Press, Oxford, 2011, Chapter 48, pp. 1324-1332.

* cited by examiner

*Primary Examiner* — Traviss C McIntosh, III
(74) *Attorney, Agent, or Firm* — Sughrue Mion, PLLC

(57) ABSTRACT

This invention provides novel 8-carbyl substituted cAMPS and a novel procedures for the preparation of 8-Br-cAMP, a key starting material.

22 Claims, 1 Drawing Sheet

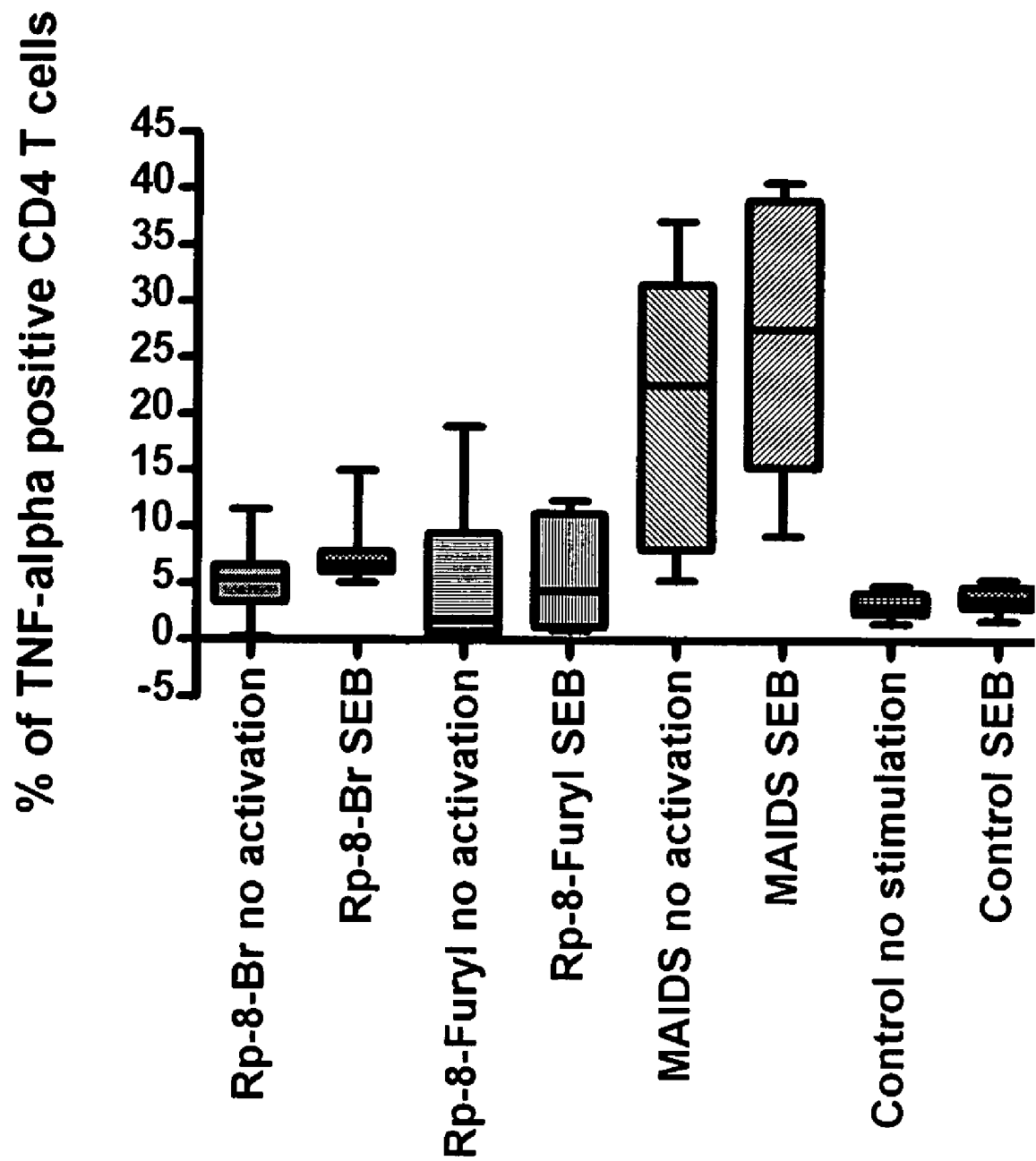

PURINE NUCLEOTIDE DERIVATIVES

This invention relates to novel purine nucleotide derivatives, to processes for their preparation, intermediates in their preparation, compositions containing them, their use in medicine and diagnostics, and to methods of treatment and assay methods using them, in particular where the purine nucleotide derivative is a purine cyclic monophosphate phosphorothioate substituted at the 8-carbon of the purine ring by a carbon-attached substituent.

The naturally occurring purine cyclic monophosphates, cyclic adenosine monophosphate (cAMP) and cyclic guanosine monophosphate (cGMP), are messenger molecules important for mediating the effects on cell function of hormones.

It has been proposed that analogs of such cyclic nucleotides may be used in treating disease states associated with reduced or enhanced immune function. Thus one such analog is adenosine cyclic monophosphorothioate (cAMPS), or more exactly adenosine 3',5'-cyclic monophosphorothioate, in which one of the oxygens pendant from the phosphorus atom is replaced by a sulphur. The phosphorus as a result is a chiral centre and in the Rp configuration (at the phosphorus atom) cAMPS is a cAMP antagonist while in the Sp configuration (at the phosphorus atom) it is a cAMP agonist. The use of Rp-cAMPS as a cAMP antagonist as part of an HIV treatment has been proposed for example in WO98/48809 and the use of cAMPS as an inhibitor of neoplastic growth has been proposed in U.S. Pat. No. 5,843,916.

WO98/48809 suggested in particular the use of cAMP antagonists which inhibit the activity of the enzyme cAMP-dependent protein kinase I (PKAI) and in this regard suggested the use of Rp-cAMPS substituted at the 8-carbon of the purine ring by a heteroatom (e.g. Br or Cl) or a heteroatom-attached group (e.g. piperidine). Moreover Gjertsen et al in J. Biol. Chem. 270:20599-20607 (1995) demonstrated that 8-chloro and 8-bromo Rp-cAMPS had a higher antagonistic activity relative to PKAI than 8-unsubstituted Rp-cAMPS.

Various 8-substituted cAMPS are available commercially from Biolog-Life Science Institute of Bremen, Germany, in particular Rp-8-Br-cAMPS, Rp-8-Br-MB-cAMPS (MB is a monobutyryl substituent at the 2' position of the ribose ring), Rp-8-Cl-cAMPS, Rp-8-CPT-cAMPS (where CPT=4-chlorophenylthio), Rp-8-HA-cAMPS (where HA=hexylamino), Rp-8-OH-cAMPS, Rp-8-PIP-cAMPS (where PIP=piperidino), Rp-8-AEA-cAMPS (where AEA=2-aminoethylamino), Rp-8-AHA-cAMPS (where AHA=6-aminohexylamino), Rp-8-$N_3$-cAMPS (where $N_3$=azido), and Rp-8-I-cAMPS. Biolog also supply Sp-cAMPS compounds but again all are either 8-unsubstituted or are 8-substituted by a heteroatom or a heteroatom-attached group.

The present treatment of HIV infection is a potent cocktail of anti-HIV drugs; highly active antiretroviral therapy (HAART). HAART includes protease inhibitors and nucleoside and nonnucleoside analogs that target the virus and is the main component in the treatment of HIV-infected patients. However, although HAART significantly prolongs life of HIV infected patients by stopping the development of AIDS, impaired T cell function seems to persist. In fact, the HIV-specific immune response has been seen to decline rather than increase during HAART. Furthermore, HAART does not eradicate the virus, patients display virological relapse upon withdrawal of treatment and in some patients the virus develops resistance to the treatment. In addition, a large number of patients develop intolerance to the present drugs with potentially serious adverse events.

Thus, there is an increasingly recognized need for other treatment modalities. Treatment based on immunomodulation that can improve the function of the somewhat "knocked down" immune system of HIV-patients might make the immune system competent in driving out the virus from its reservoirs and could be an important adjuvant therapy in HIV-patients. Elevated levels of cAMP and thus increased activation of PKA type I significantly inhibit proliferation of T cells from HIV-infected individuals independent of ongoing HAART. Use of a selective antagonist of PKA type I improves the impaired proliferation of T cells from HIV-infected patients up to 300%. The observations described above suggest PKA type I as a potential target for immunomodulating therapy. PKA type I selective antagonists such as Rp-8-Br-cAMPS offer one possibility to reverse the inappropriate activation of PKA type I in immunodeficiencies and thereby restore T cell function and immune responsiveness. It has been shown that most Rp-cAMPS isomers act as antagonists of PKA by competitively binding to the cAMP binding sites of the R subunit, but do not dissociate and activate the enzyme.

Furthermore, characterization of derivatives of Rp-cAMPS has shown that some compounds (e.g. Rp-8-Br-cAMPS) act as selective and full antagonists of the PKA type I isoenzyme and as partial agonists of the PKA type II isoenzyme. Most cells and tissues contain highly significant amounts of PKA type II anchored at a number of subcellular sites and implicated in mediating a large number of cAMP induced effects.

In contrast, although PKA type I is also widely distributed, it has mainly been shown to be necessary and sufficient for regulation of function of immune cells. This offers some tissue/cell selectivity, which could favor a potential treatment based on a PKA type I selective antagonist. Despite PKA type I being an interesting drug target, no pharmaceutically acceptable cAMP antagonist is available. Development of immunostimulatory drugs that interfere with cAMP action will improve the immune function of T lymphocytes and can be brought to pre-clinical testing by developing PKA type I selective cAMP antagonists that counteract cAMP action. The specific aims of the performed research were the development of such compounds and development of methods and models for evaluation of compounds as immunostimulatory drugs that reverse the immunodeficiency in HIV.

We have now surprisingly found that particularly high PKAI (or more precisely PKA RIα) affinity, i.e. cAMP agonism and more especially antagonism, may be achieved using cAMPS in which the purine 8-carbon is substituted by a carbyl group, i.e. a carbon-attached group.

Thus viewed from one aspect the invention provides 8-carbyl substituted cAMPS or a derivative thereof.

By the term derivative in this context is meant a compound which is chemically modified but retains the ability to exert the activity of the 8-substituted cAMPS in use, e.g. a salt, ester, prodrug (i.e. bioprecursor), etc. form. Where the derivative contains or generates in use a component separate from the 8-substituted cAMPS, e.g. a counterion or a cleavable protective group, this component is preferably physiologically tolerable.

The 8-substituent, which as stated is required to be attached to the 8-position on the adenine ring by a carbon-carbon bond, may typically contain up to 25 non-hydrogen atoms, more preferably up to 20, especially up to 15, particularly up to 10. These non-hydrogen atoms include at least one carbon and may all be carbon; however preferably at least one, e.g. up to 6, of the non-hydrogen atoms may be heteroatoms, e.g. halogen, oxygen, sulphur, nitrogen or phosphorus, especially O, N or S. The 8-substituent may be linear, branched or cyclic or a combination of two or more thereof and may be saturated or unsaturated. Especially preferably the substituent is or contains a cyclic group, in particular a homo or heterocyclic aryl group, e.g. containing 5 to 10 ring atoms, most particularly a heteroaryl group containing 5 ring atoms or a phenyl group. Thus for example the substituent may be an aryl, aralkyl, alkaryl, alkyl, cyclic alkyl, alkenyl, or alkynyl group optionally attached via a carbonyl or thiocarbonyl group and optionally substituted by acyl, halo, hydroxy, thiol, amino, carboxy (or other oxyacid), cyano, azido, alkoxy, ester, ether or alkylthio groups. In any such substituents, alkyl groups or unsaturated analogs thereof preferably contain up to 10 carbons, particularly up to 6 carbons.

Examples of typical 8-substituents according to the invention include aryl groups such as benzene, naphthalene and annulated carboxylic systems, and annulated heterocyclic systems including pyridine, di- and triazines, furan, thiophene and pyrrole, and the azoles, and triazoles, and oxa- and thiadiazoles, and tetrazoles; heteroaryl groups such as the six-membered ring azines, pyridine, the diazines, triazines and annulated carbocyclic systems, and annulated heterocyclic systems as defined above, and five-membered ring systems such as furan, thiophene and pyrrole, the azoles, and triazoles, and oxa- and thiadiazoles, and tetrazoles and annulated heterocyclic and carbocyclic systems as defined above; optionally substituted aryl and heteroaryl groups, e.g. substituted by (i) $OR^1$ where $R^1$=H, $C_1$-$C_{10}$ alkyl, $C_2$-$C_{10}$ alkenyl, $C_2$-$C_{10}$ alkynyl, aryl or heteroaryl groups, and optionally substituted derivatives thereof,
(ii) $SR^1$, $SOR^1$ and $SO_2R^1$, where $R^1$ is as defined above,
(iii) $NR^1R^1$ where each $R^1$ which may be the same or different is as defined above,
(iv) halogen,
(v) $CO_2R^1$, $COR^1$, or $CONR^1R^1$ where each $R^1$ which may be the same or different is as defined above, and
(vi) additional optionally substituted aryl and heteroaryl groups;

carbonyl, thiocarbonyl, iminocarbonyl and cyano derivatives such as $CO_2R^1$, $COR^1$, $CONR^1R^1$, $C(NR^1)NR^1R^1$, $CSNR^1R^1$ and CN where each $R^1$ which may be the same or different is as defined above; and non-aromatic carbon substituents which are optionally substituted, such as $C_1$-$C_{10}$ alkyl,
$C_2$-$C_{10}$ alkenyl,
$C_2$-$C_{10}$ alkynyl, e.g. where the optional substitution involves
(a) insertion of additional double and triple bonds into $C_2$-$C_{10}$ alkenyl or alkynyl groups
(b) insertion of oxo groups to form ketones or aldehydes
(c) substitution by aryl and heteroaryl substituents themselves optionally substituted by halogen (e.g. F and/or Cl), $OR^1$, $SR^1$, S-oxides (e.g. $SOR^1$ and $SO_2R^1$), $NR^1R^1$, $CO_2R^1$, or $CONR^1R^1$ where each $R^1$ which may be the same or different is as defined above.

Particularly preferred 8-substituents include phenyl, furyl, and thienyl groups, especially 2-furyl groups.

Where the 8-substituent is an aryl group it may if desired be substituted by one or more polar groups, e.g. $OR^1$, $SR^1$, $SOR^1$, $SO_2R^1$, $NR^1_2$, halogen, $CO_2R^1$, $COR^1$, $CONR^1R^1$, $NO_2$, $P(OR^1)_2$, and $CH_2OR^1$.

In the 8-carbyl-substituted cAMPS of the invention, other skeletal positions may if desired also be substituted, e.g. the 2'-oxygen, the nitrogen of the 6-amino group and the oxygen and sulphurs pendant from the cyclic phosphorus atom. In this regard the substituents may be substituents as defined above for the 8-position or for example substituents known in conjunction with cAMP and cAMPS (e.g. acyl, alkylcarbonyl, aryl, etc.) Silyl substitution of the 2'-oxygen is especially preferred in compounds according to the invention which are 2'-protected versions of active compounds.

With the exception of substitutions to produce a prodrug, the compounds according to the invention are desirably used in a form where only the 8 position is substituted. Prodrug forms in which the phosphorus-pendant oxygen or sulphur is substituted so as to mask the acidity of the cyclic phosphorus group however are particularly preferred. Such prodrugs may thus for example typically be S-alkylated. While S-alkylation is a preferred option, the group introduced may typically be an ester, or thioester (i.e. R—CS—S—R—, R—CO—S—R— or R—CS—O—R—) group attached directly or indirectly to a methylene group attached to the sulphur of the phosphorothioic acid. In the case of indirect attachment, the linker preferably contains a delocalized electron structure such that (thio)ester cleavage triggers deprotection (e.g. using P-acyl-benzyl protecting group as in Scheme 2b below). Alternatively, prodrug forms may be used in which the amino group in the 6-position of the adenine ring or the hydroxyl group on the furyl ring is protected by a group eliminatable following administration, e.g. an ester or double ester protective group. Similarly, the 6-amino group can be N-protected by an acyloxyalkyl group such as pivalyloxymethyl or by an alkyloxymethyl group. In general, in the production of such prodrugs, the amine or hydroxyl protection can be effected either before or after the thiation depending on the nature of the O- and N-protective groups.

Compounds substituted at the phosphorus-pendant oxygen or sulphur may be especially useful where the preparation process requires separation of the Rp and Sp isomers, e.g. by chromatography or crystallization. Compounds in which the 2'-position is silylated may likewise be particularly preferred as intermediates to facilitate purification.

The 8-carbyl substituted cAMPS of the invention may be in the Rp or the Sp configuration or may contain both Rp and Sp isomers. For use according to the invention, the compound is preferably at least 90% Rp (or Sp), especially at least 95%, particularly at least 98%. For use as a cAMP antagonist, the compound is preferably majoratively in the form of the Rp isomer; for use as a cAMP agonist it is preferably majoratively in the form of the Sp isomer.

Described in particular detail below are four process schemes by which the 8-carbyl substituted compounds of the invention may be made. In the first, an 8-halogenated 3'5'-cyclic phosphoramidate is 8-carbylated whereafter the phosphorus attached nitrogen is replaced by a sulphur in a reaction which retains the configuration of the chiral phosphorus; in the second and third an adenosine is 8-carbylated whereafter the cyclic phosphorus group is introduced; and in the fourth an 8-halo-cAMPS is 8-carbylated. The first and second process schemes are preferred for reasons of flexibility (and retention of stereochemistry) in the case of the first and of economy in the case of the second. All these process schemes form a further aspect of the invention. Viewed from this aspect the invention provides a process for the preparation of an 8-carbylated cAMPS or derivative thereof, said process comprising at least one of the following steps:

a) reacting a 2'-protected 8-carbylated-adenosine 3',5'-cyclic phosphoramidate with carbon disulphide and deprotecting the 2'-hydroxyl;
b) reacting an 8-carbylated-adenosine with $SPCl_3$ in a dry solvent;
c) reacting an 8-carbylated-adenosine with a phosphite and subsequently with sulphur;
d) reacting an optionally 2'-protected-8-halo-cAMPS with an alkylating agent and if required deprotecting the 2'-hydroxyl;
e) transforming an 8-carbylated cAMPS into a salt thereof;
f) reacting an 8-carbylated cAMPS with a biologically cleavable protecting group; and
g) separating Rp and Sp isomers of an $R_p/S_p$ isomer mixture of an 8-carbylated cAMPS or derivative thereof.

Carbylation in the purine 8-position can be effected particularly readily using a material functionalized in the 8-position. A convenient functionalisation in the 8-position in the purine heterocycle can be achieved by introduction of a bromine atom by a simple bromination.

The 8-carbyl substituent in the compounds of the invention may be an electron donor or electron withdrawing group as desired.

Adenosine is brominated regioselectively in the 8-position by addition of bromine to a NaOAc buffered aqueous solution at ambient temperature. cAMP can be brominated in a similar manner, but is also commercially available. Alternatively, halogenation in the 8-position can be effected by way of the corresponding lithiated species and addition of halogen, in particular the method has been used for bromination and iodination of adenosine. The substrate in this case was fully silyl-protected (TBDMS) adenosine. Lithiation in the 8-position was effected with nBuLi under standard conditions. This approach may offer the best access to 8-iodo derivatives.

Carbylation Reactions:
(i) At both the nucleoside level or the cyclic nucleotide level, carbylation can be effected by transition metal catalysed cross-coupling reactions. We have developed methodology useful for the preparation of a series of palladium-catalysed reactions.
(ii) At the intermediate cyclic phosphoramidate level, carbylation in the purine 8-position can be effected by transition metal catalysed cross-coupling reactions.
(iii) Carbylation can also be effected at the cyclic phosphorothioic acid level. Preferentially the phosphorothioic acid exists in the form of an O-ester or an S-ester. The ester can subsequently be cleaved to the corresponding phosphorothioic acid derivative.

In cross-coupling reactions, simple alkylation has been effected under Pd-catalytic conditions in reactions between peracetylated 8-Br-adenosine and tetraalkyl stannanes. A more convenient method for the synthesis of lower alkyl purine nucleosides is available by palladium-catalysed cross-coupling reaction of halogenopurine nucleosides with trialkylaluminums. Both vinylation and allylation have been effected from the appropriate stannanes using Pd-catalysis. The alkyne function has been introduced via an 8-bromo derivative which was coupled with terminal alkynes using Pd-catalysis in the presence of Cu(I) iodide under the Sonogashira conditions.

The reaction schemes shown below are illustrative—other reagents and end products may be used or made analogously.

Process I

Amidate Intermediates for Thiylation:

Preparation of $(R_p)$-8-Substituted Adenosinephosphorothioic Acids

Scheme 1

General methodology:

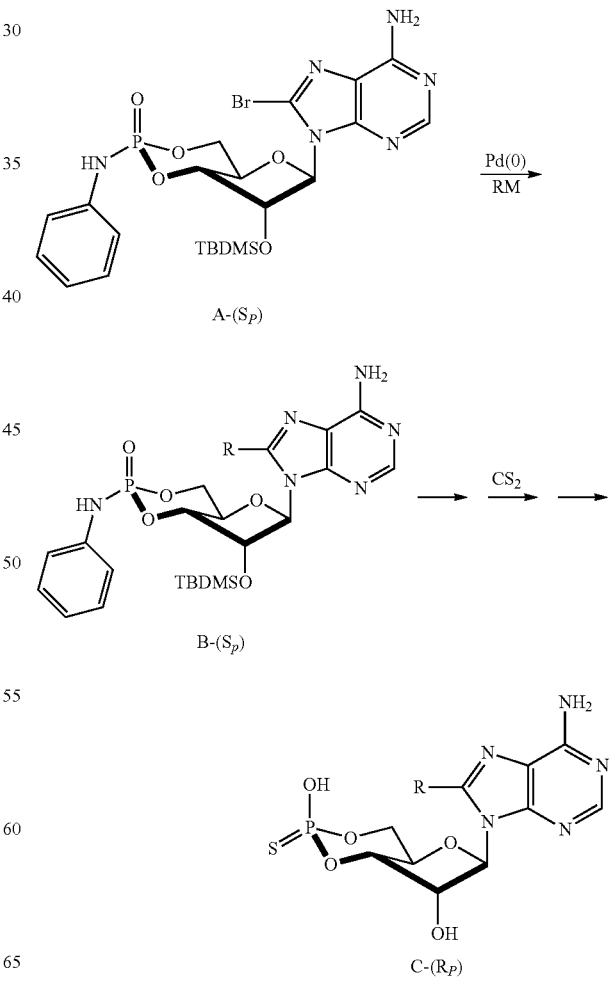

In this method for the synthesis of the phosphorothioates C in Scheme 1, cAMP amidates intermediates are essential substrates. cAMP is brominated as described for adenosine, or the bromo compound is obtained commercially. The literature describes a method for the preparation of a diastereomer mixture of 3',5'-cyclic phosphoramidates (see Stec, Acc. Chem. Res. 16:411-417 (1983) and Beres et al. J. Org. Chem. 50:1271-1278 (1985)). The initial step involves an Apple-type reaction with $Ph_3P/CCl_4$ to provide the corresponding phosphoryl chlorides. Apparently there is little stereochemical control during chlorination at the phosphorus atom. Hence a diastereoisomer mixture of anilides results after amidation of the chlorides. (cf. Scheme 2). The amidates are neutral molecules which are soluble in a number of organic solvents and can be separated into the pure diastereoisomers by chromatographic procedures, or by fractional crystallisations.

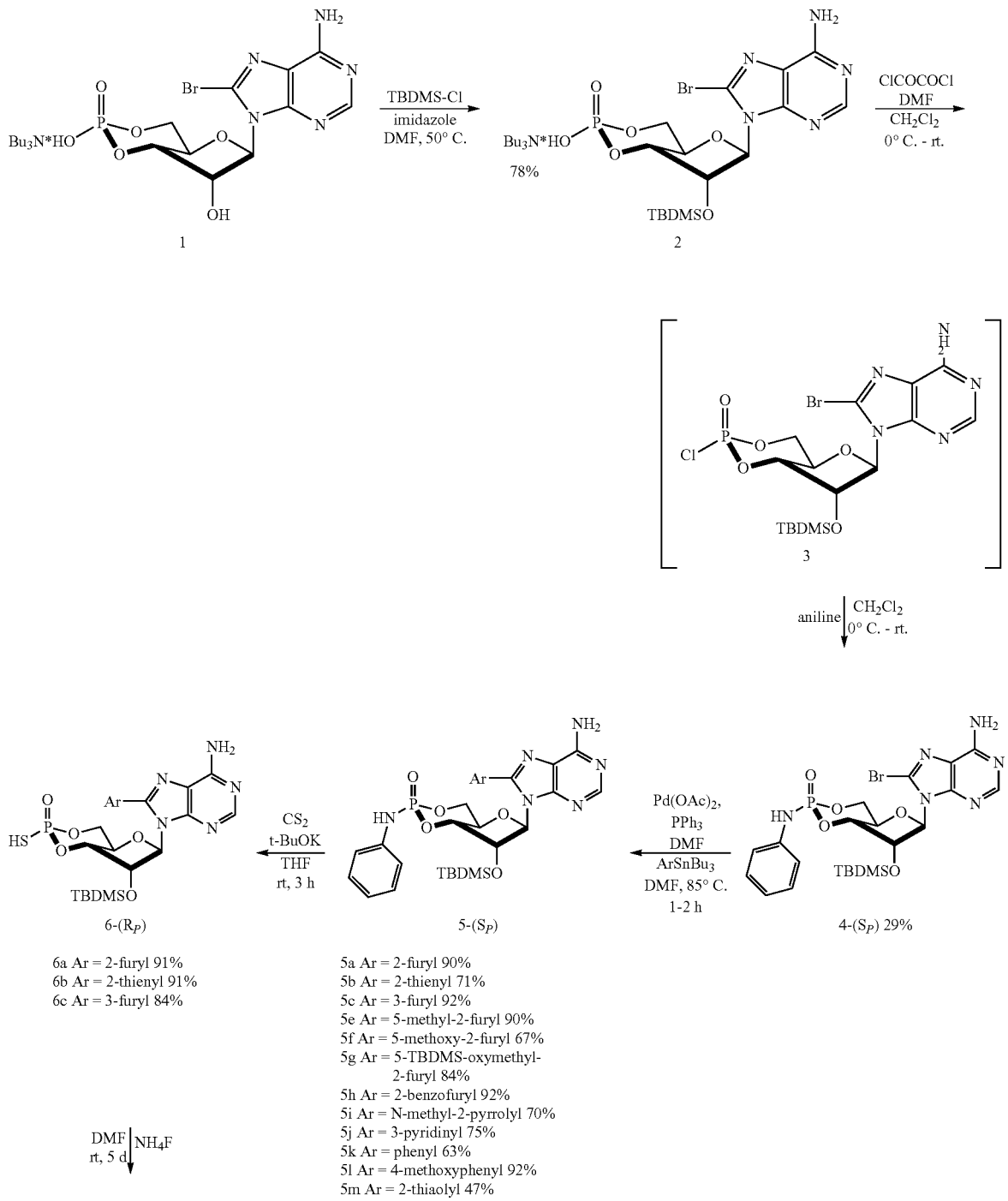

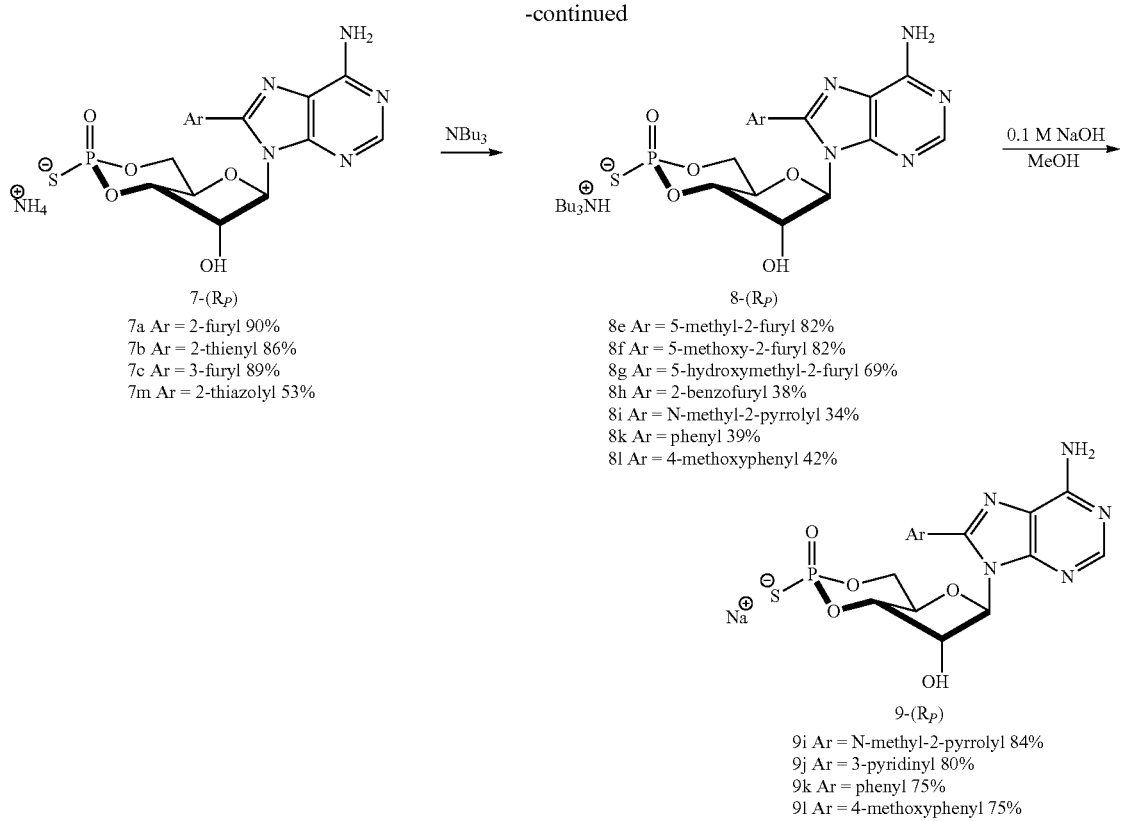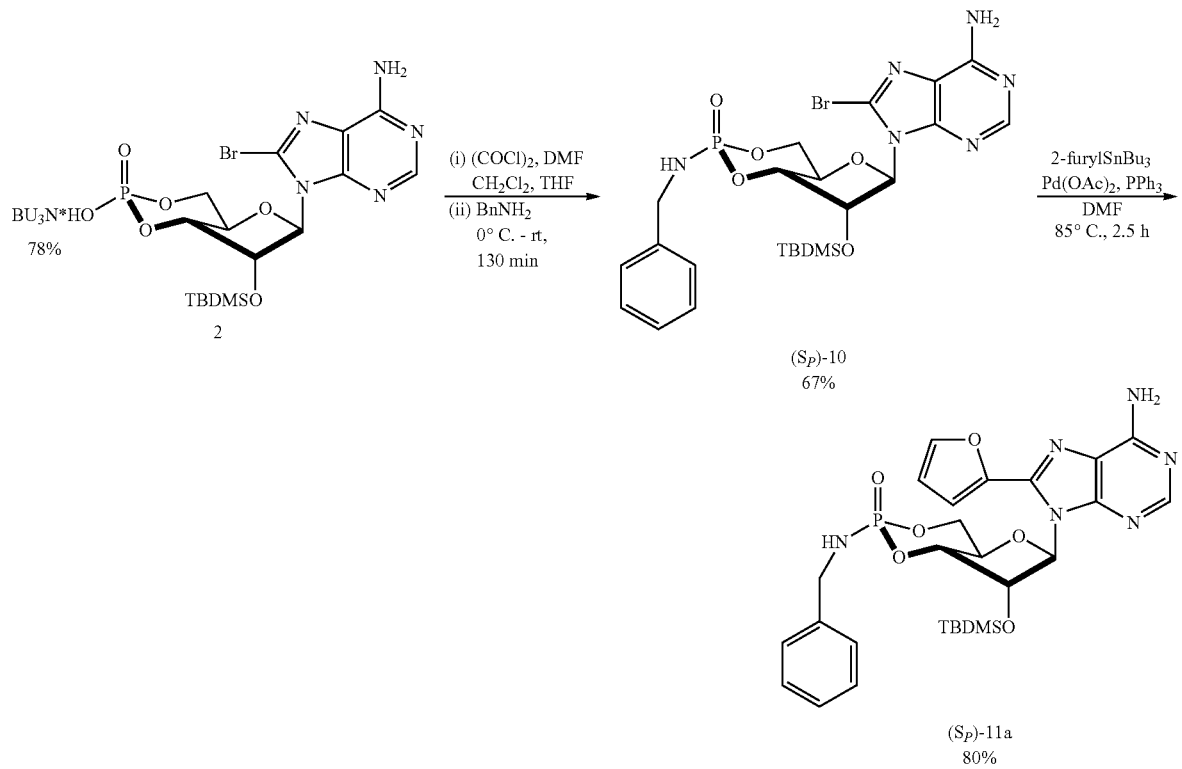

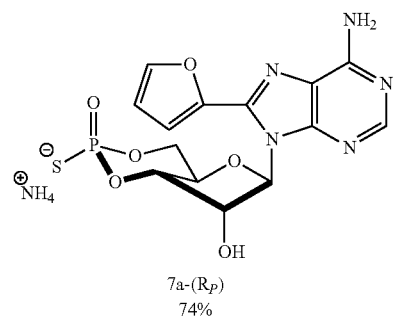
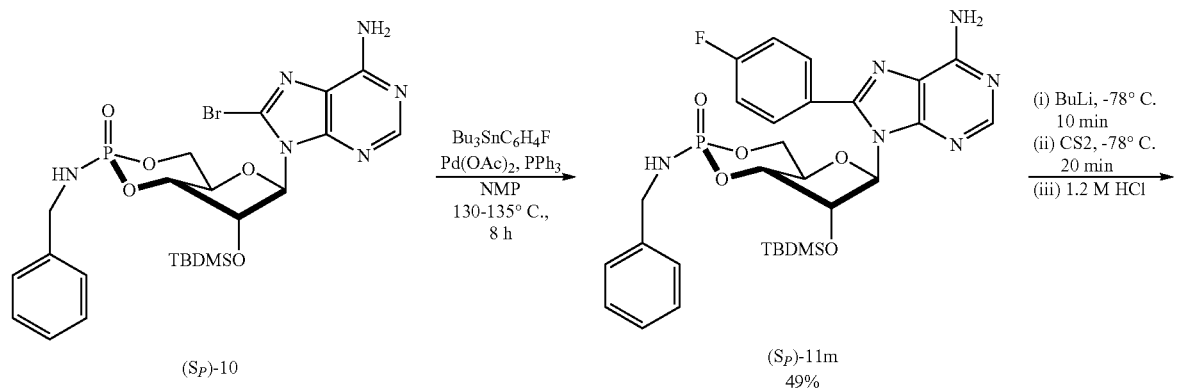
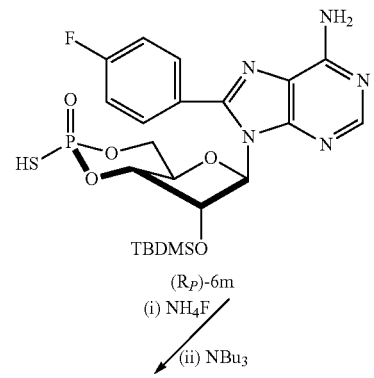
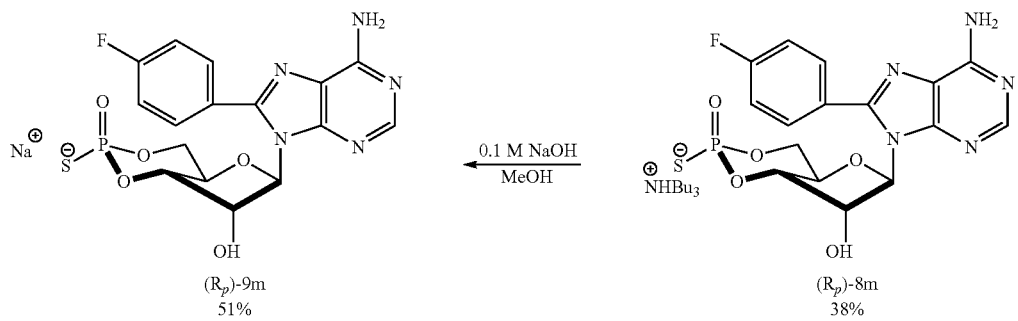

Scheme 2b

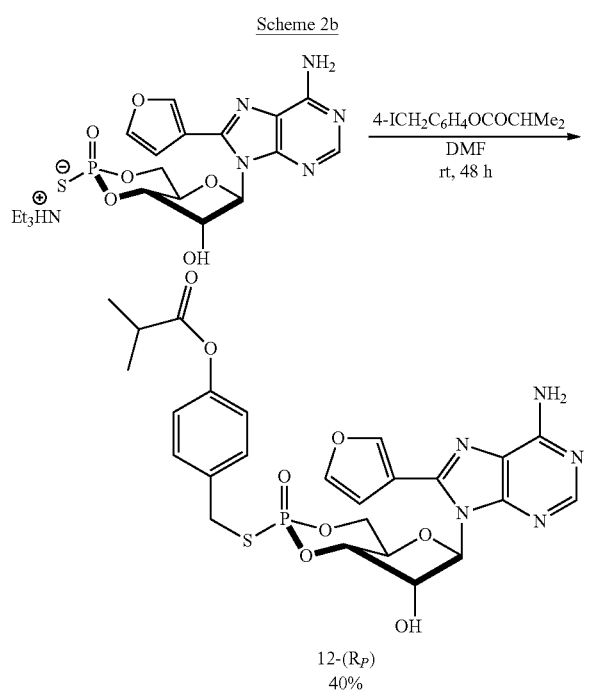

12-(R$_P$)
40%

In our new and inventive procedure in Scheme 2, cAMP-8-Br as an ammonium salt 1 is 2'-O-protected by a bulky silyl group. TBDMS-Cl is a convenient and efficient reagent for this purpose (TBDMS=tert-butyl dimethyl silyl). The silyl ether 2 is subsequently chlorinated to form structure 3.

The bulky silyl group also has a second important function in the synthetic sequence. It allows the product after thiation to be precipitated efficiently from an aqueous reaction mixture and is helpful in the purification as described below. Other protecting groups with similar properties might also be used.

In the chlorination method, oxalyl chloride has been used successfully together with catalytic amounts of, or even an excess of DMF. The actual chlorinating agent of phosphorus is an intermediate chloro-imino derivative which is generated in situ from oxalyl chloride and DMF. The desired phosphoryl chloride stereomer 3 can be isolated. The crude product, however, may be used in the subsequent amidation step.

Various primary amines, or masked amines, can be used for the amination. Nucleophilic amines react readily with the chloride. The amidates, however, must be sufficiently strong acids for an abstraction of the remaining hydrogen of the amino group. Several aromatic amines would satisfy the latter requirement. We have chosen aniline for our work. The reaction with aniline can be effected in dichloromethane in the cold. Under these conditions the reaction is stereospecific in that only one amidate stereoisomer 4 is obtained from the reaction mixture.

The amidates are neutral molecules which are readily dissolved in several common organic solvents. Hence these molecules are appropriate for carbylation reactions in the 8-position. Several transition metals will catalyse this process. We have used extensively palladium in the catalyst systems. In most cases Stille conditions with stannyl reagents have been used in our preliminary work. The yields of cross-coupled products are excellent. Other organometallic reagents can be used, e.g. zinc and boron compounds. Coupling of a boronic acid under Suzuki conditions proceeds in the same manner as shown in Scheme 3. Hence a number of 8-substituted derivatives will become available by this methodology.

Scheme 3

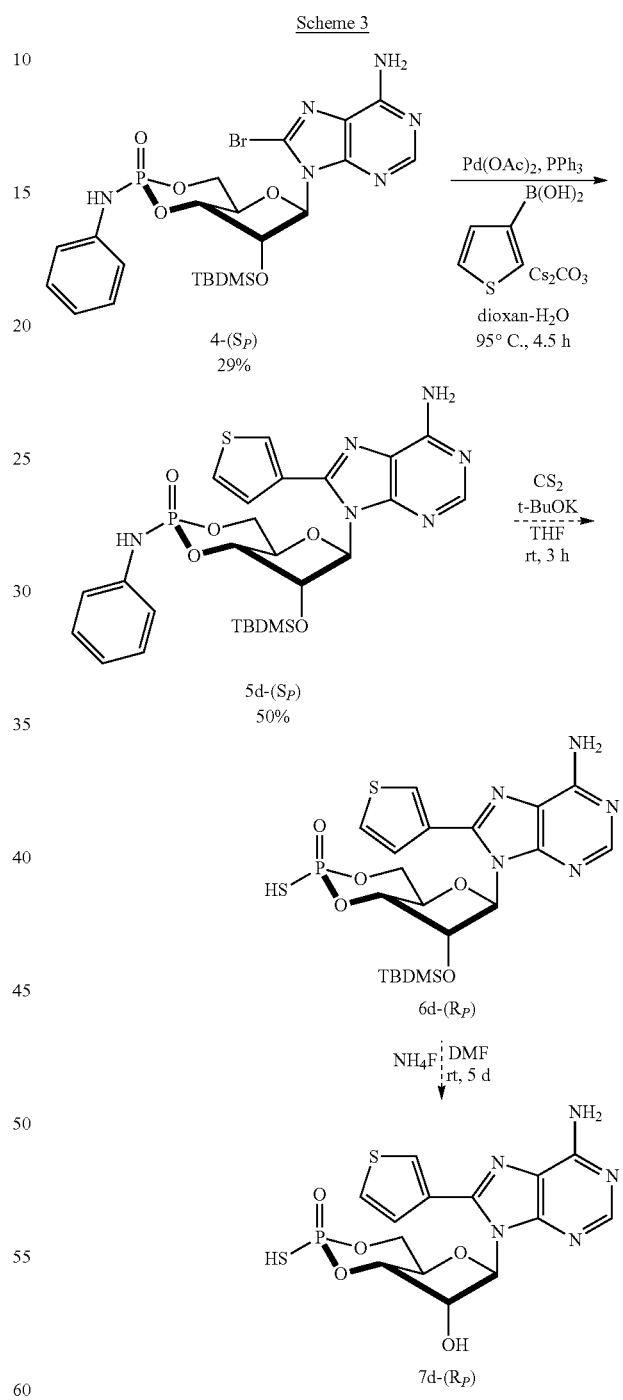

The 8-bromo derivative 4 and the 8-carbylated amidates 5 and 11 in Schemes 2, 2a and 3 are subsequently thiated. Thiylation by means of carbon disulfide for displacement of the amine has been recommended. We find that with carbon disulfide in THF and potassium tert-butoxide as base, the thiation at room temperature requires less than 3 hours. The phosphorothioates 6 are obtained in excellent yields. The substitution proceeds stereoselectively with retention of the configuration at the phosphorus atom. However, the formal configurational assignments are changed because of the nomenclature priority rules. This work leads to the Rp configuration in the phosphorothioic acid target molecules.

Besides protection, the presence of a bulky silyl group is very important for the isolation of the thiated product 6 because of its relative solubilities in the isolation and purification process.

Desilylation of the product 6 is effected by ammonium fluoride in DMF solution. The desilylation is run at room temperature over 5 days after which the target products 7 are isolated in excellent yield. In this way both 8-carbylated target products, as well as the 8-bromo cAMPS, are obtained. When desirable, the 8-bromo cAMPS can be a substrate for cross-coupling reactions after O- or S-protection in the acid function as referred to in Process IV.

The formation of the amidates (4 in Scheme 2) in a stereoselective manner is an important step in the synthesis outlined in this section. The aniline amidate hydrogen is sufficiently acidic to allow ready abstraction (e.g. with an alkoxide base) for the subsequent thiation. A very efficient and stereoselective thiation however can also be achieved where an aliphatic or substituted aliphatic amine (e.g. benzylamine) is used in place of aniline for amidate formation. In this case a strong base (e.g. butyl lithium) is used for deprotonation (see for example Scheme 2A).

Where aliphatic or substituted amines (such as benzylamine) are used, moreover, 8-carbylation may advantageously be effected using organozinc compounds, especially the ones where the organo group is a small heterocycle, in particular one attached at a ring carbon adjacent a ring heteroatom, e.g. in conjunction with a palladium catalyst. In general, where a cyclic group is to be linked to the 8-position, it is preferred that the atoms adjacent to the ring carbon attachment site are unsubstituted.

Process II

Thiation by Ring-Closing Reactions:

(Rp)-cAMPS has been synthesized enzymatically from the corresponding nucleoside 5'-O-(1-thiotriphosphate). Enzymatic techniques are not used in the Examples below but would provide an alternative procedure.

In a chemical synthesis N-benzoyl-adenosine without O-protection was treated with bis(p-nitrophenyl)phosphorochlorothioate in pyridine. The product, adenosine 5'-bis(p-nitrophenyl)phosphorothioate, was subsequently cyclised in dry DMF with potassium tert-butoxide as base. After deblocking with conc. aqueous ammonia, the diastereomers were separated by chromatography.

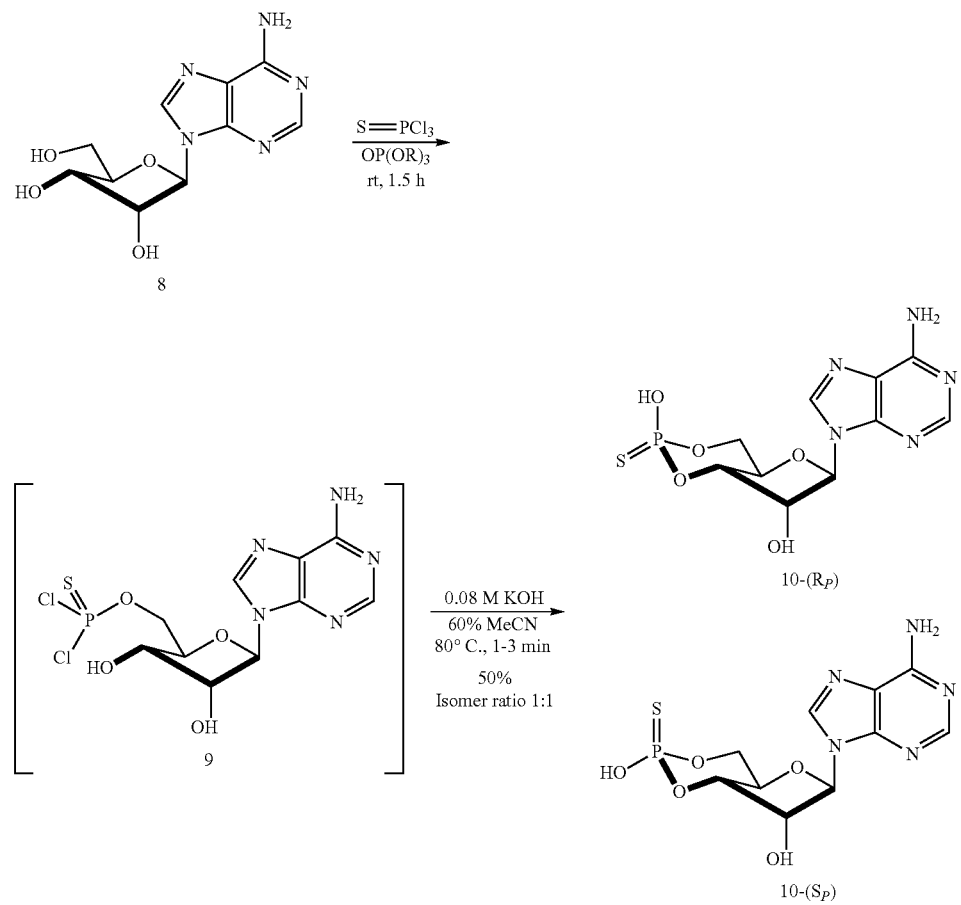

Scheme 4

Synthesis of nucleoside-3',5'-cyclic phosphorothioate by cyclothiophosphorylation of unprotected nucleosides has been effected with thiosphosphoryl trichloride (Scheme 4). The initial phosphorylation presumably takes place at the 5'-OH group in the sugar. Trialkyl phosphates are recommended as solvents. The products have been cyclised directly at high dilution by alkali hydroxide in aqueous acetonitrile to give the diastereoisomeric nucleosides-3',5'-cyclic phosphorothioates cAMP in a 1:1 ratio which have to be separated by chromatographic techniques. The diastereoisomers of the parent compound 10 in Scheme 4 carry no substituent in the 8-position.

In the present invention the adenosines 8 have been converted into (Rp)-8-substituted-adenosine-3',5'-cyclic phosphorothioates 7 as outlined in Scheme 6. We have developed a method which delivers almost exclusively the desired 3',5'-cyclic phosphorothioates 7, but as a stereochemical mixture. The reaction is clean in this respect when thiophosphorylation and cyclisation are effected in dry pyridine in the cold. Either stereoisomer can be isolated in a pure state after a chromatographic separation. The 8-phenyl derivative 7e was prepared by this methodology shown in Scheme 5.

When desirable, ($S_p$)-cAMPS derivatives would be available in a similar manner.

Scheme 5

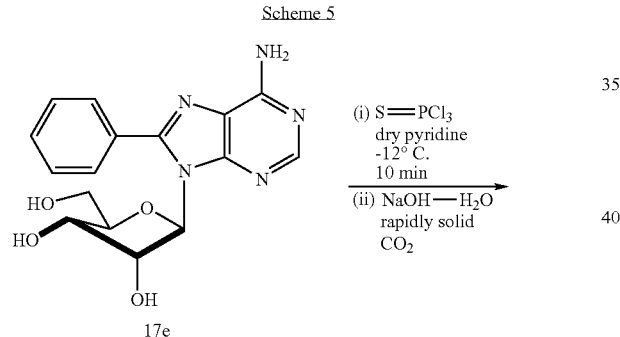

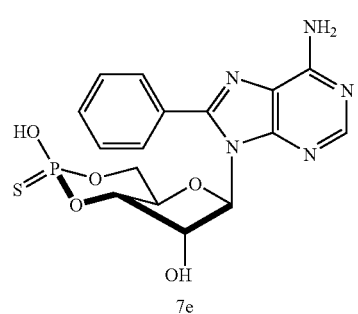

The finding that the pyridine and similar solvents must be especially dried represents an invention since the cyclisation reaction under these conditions is much improved both in selectivity and yield.

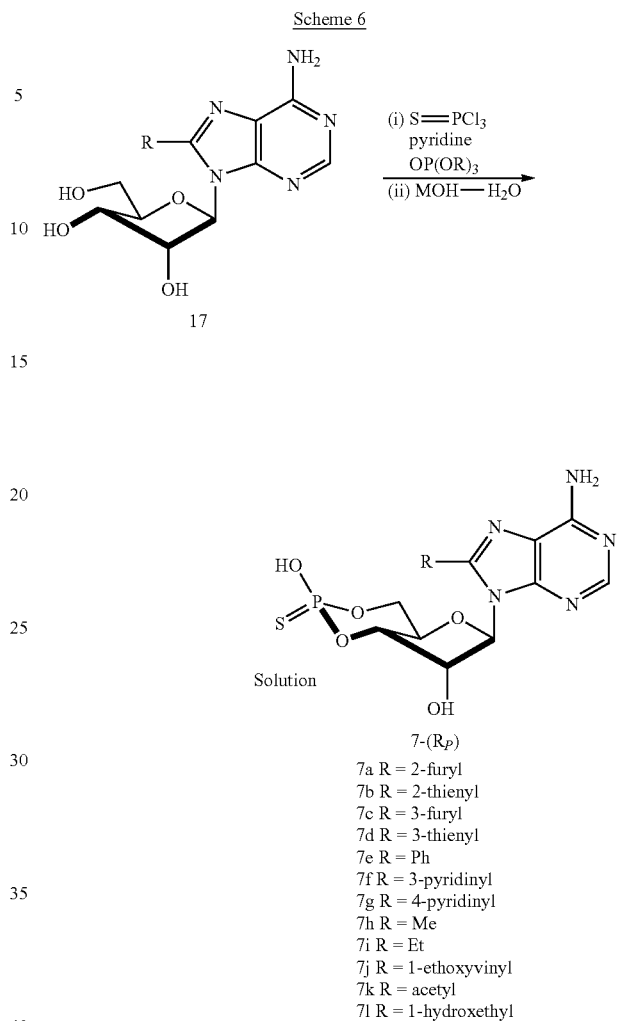

For Process II and Process III work, we have prepared a great number of 8-carbylated nucleosides. The nucleoside intermediates were cyclised in a routine fashion using thiophosphoryl chloride. The carbylation reactions of adenosines are summarized in Scheme 6.

For the carbylation of nucleosides in Scheme 7, the 8-bromo derivative 11 of adenosine was used. Protection of the sugar hydroxyl groups was either by acetylation to provide the triacetylated substrate 12 or by silylation to provide the trisilylated substrate 13 Several Pd-catalyst systems were used for the cross-coupling reaction. The reaction conditions had to be varied. Some of our better conditions are given in Scheme 7 for the preparation of the compounds 14-16. Stille conditions were used for the preparation of cross-coupled products 14, whereas methylation (15a) was effected from trimethylaluminum under Negishi conditions. The same conditions were also used to prepare the 2-furyl derivative 15b in the same yield as obtained under the Stille conditions which provided the same compound numbered 14b.

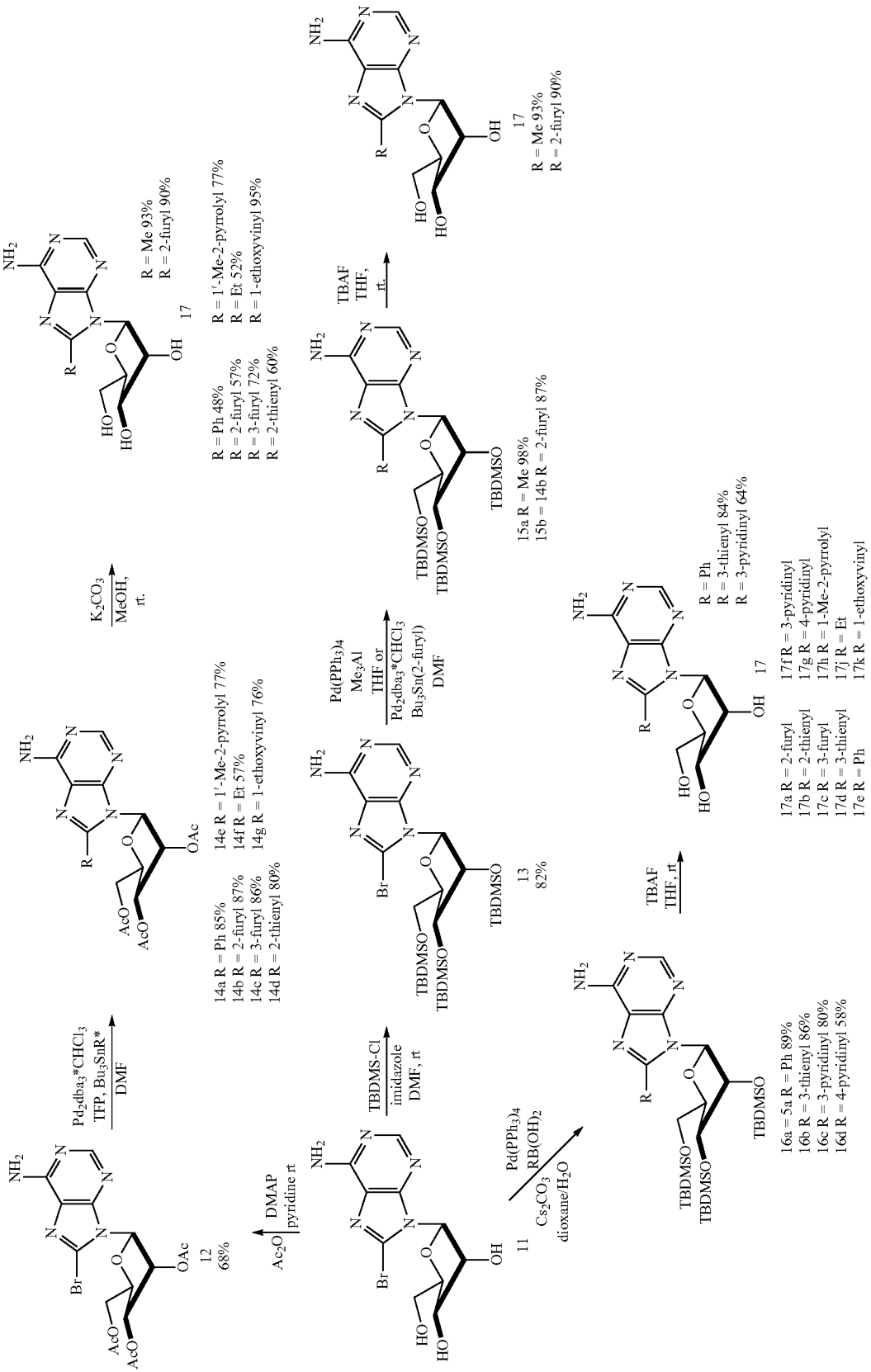

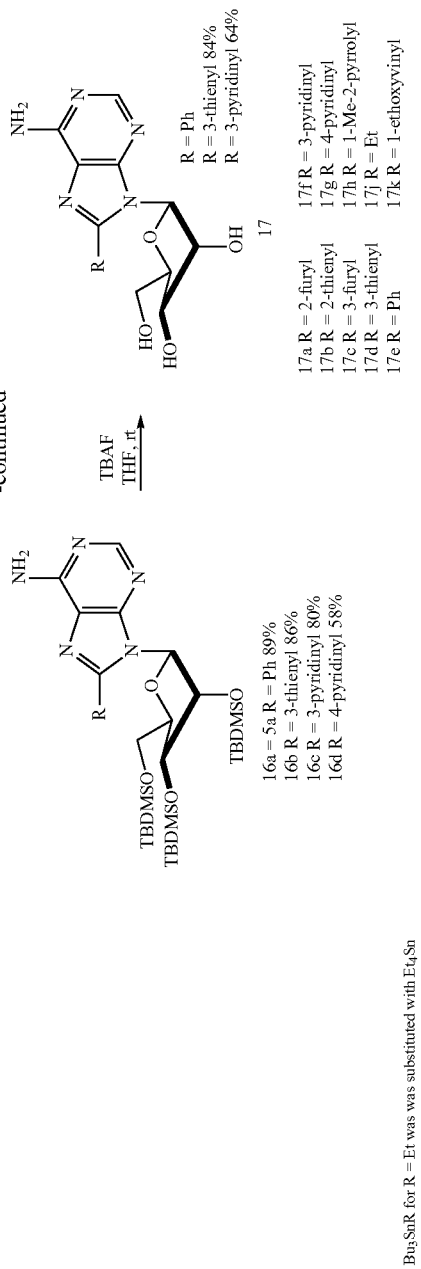

Reactions from boronic acids under the Suzuki conditions also proceeded well to furnish compounds 16 in high yields. The phenyl compound 16a was obtained in approximately the same yield as 14a under the Stille conditions. The 8-substituted adenosines were subsequently prepared under hydrolytic conditions from the esters 14, and by tetrabutylammonium fluoride desilylation from the silyl ethers 15 and 16. All reactions proceeded satisfactorily.

Scheme 8

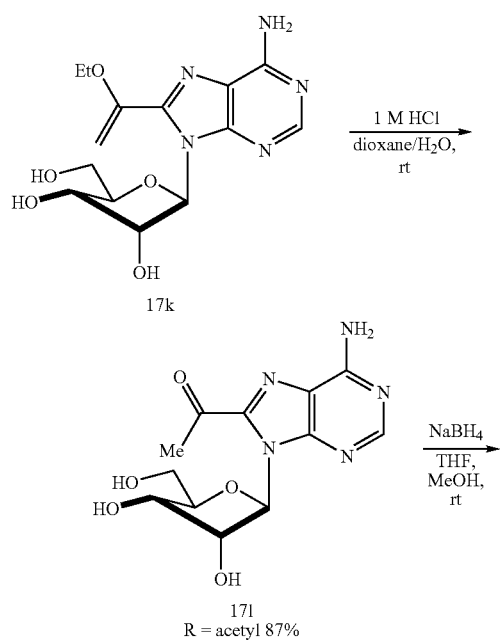

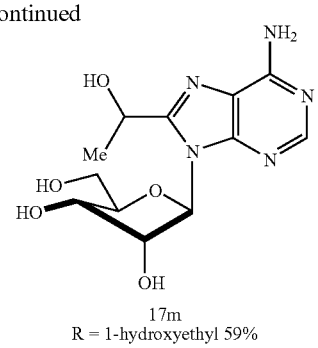

17m
R = 1-hydroxyethyl 59%

Scheme 8 shows the preparation of adenosins carrying an oxo group and a hydroxyl group at the α-carbon in the 8-substituent. The starting material was the cross-coupled 8-(α-ethoxyethenyl)adenosine 17k. Mild acid conditions cleaved the vinyl ether function with formation of the acetyl derivative 17l in high yield. A subsequent sodium borohydride reduction gave the corresponding hydroxyl derivative 17m. No stereoselectivity was observed at the epimeric alcohol carbon. No attempts were made to separate the stereoisomers present in equal amounts.

Process III

Phosphite P(III) Approach:

The 8-carbylated nucleosides 17 and their derivatives in Schemes 7 and 8 are appropriate substrates for Process III as well as for Process II (vide supra). So far, we have demonstrated the principle for Process III by the preparation of the parent phosphorothioic acids 19. 8-Carbylated analogs are indicated by the 8-R substituent in substrate 9 displayed in Scheme 9.

Scheme 9

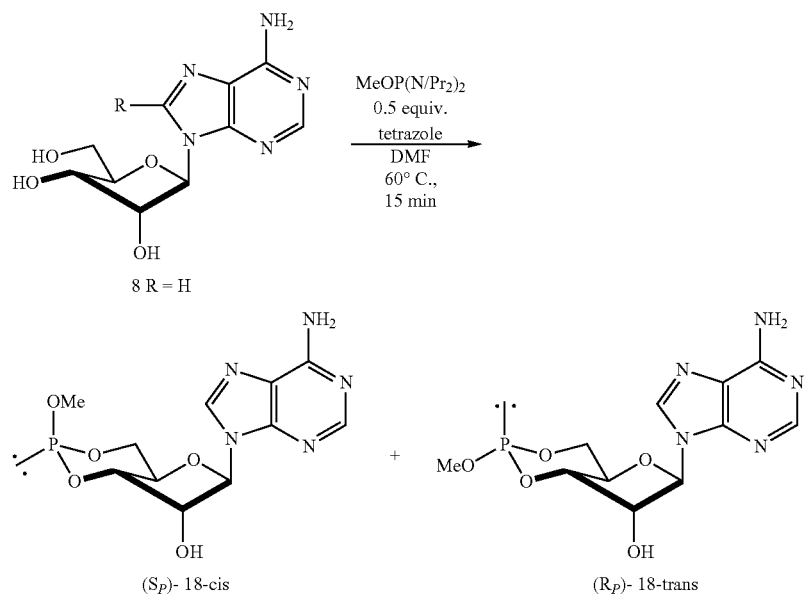

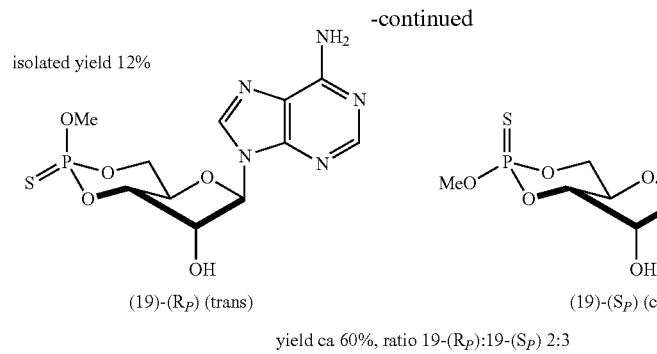

isolated yield 12%

(19)-(R_P) (trans)    (19)-(S_P) (cis)

yield ca 60%, ratio 19-(R_P):19-(S_P) 2:3

Adenosine will react with trivalent phosphorus reagents to form cyclic phosphites. To ensure regioselective 3',5'-cyclophosphitylation, an initial attack from a bifunctional phosphorus(III) reagent on the primary 5'-hydroxy group is required. Therefore the best reagents would have a considerable steric bulkiness. According to the literature, 2'O-methyladenosine can be converted into 2'O-methyl-cis-adenosine-3',5'-cyclic methyl monophosphite in reactions with bis(N,N-diisopropylamino)methoxyphosphine. The reaction is promoted by 1H-tetrazole. Both the cis- and trans-cyclophosphite esters are formed. At elevated temperature the trans-diastereomer is inverted to the cis-isomer.

Each isomer separately, or as a mixture, can subsequently be thiated with sulfur. The oxidative addition of sulfur occurs at the site of the lone pairs of electrons on the phosphorus atom with retention of the relative configuration at the phosphorus atom. The oxidative thiation is run on a stereoisomer mixture or on a pure stereoisomer. In the former approach, an additional separation of the phosphorothioic acid stereomers is required.

We have found that phosphitylation can equally well be performed on the unprotected adenosine. The product first formed was a mixture of cis-($^{31}$P NMR δ 123 and trans-($^{31}$P NMR δ 129) phosphites. The mixture was equilibrated to the cis-isomer without loss of material. Additional 1H-tetrazole was found to accelerate the isomer transformation. Each isomer separately, or as a mixture, was subsequently thiated with sulfur. The oxidative addition of sulfur occurs at the site of the lone pairs of electrons on the phosphorus atom with retention of the relative configuration at the phosphorus atom. In the example described herein, the oxidative thiation was carried out on a mixture of the phosphate diastereoisomers. In this case the phosphorothioic acid diastereomers are separated by chromatography.

Process IV

Carbylations

Carbylations by cross-coupling reactions can be carried out at the final phosphorothioic acid level as indicated in Scheme 10. The substrate carries a leaving group in the purine 8-position. A reaction sequence is illustrated for the 2'-OTBDMS-8-bromo derivative 20 which is available by reactions shown in previous schemes, either as a pure stereoisomer or as a diastereoisomer mixture, which needs to be separated into pure stereoisomers after the carbylation reaction has been effected.

Either the S- or the O-atom of the thiophosphoric acid is protected to provide the S-ester 21 or the corresponding O-ester. As shown in Scheme 11, the S-ester 21 is cross-coupled either under Stille or Suzuki conditions, or subjected to alternative modifications used in cross-coupling reactions, to provide the 8-carbylated product 22. The latter can be deprotected to the thioic acid 6, and further to the target compound 7. Coupling reactions can in a similar way be effected on substrates with a free 2'-OH group, the sequence 23→25, and further on to the target compound 7.

Scheme 10

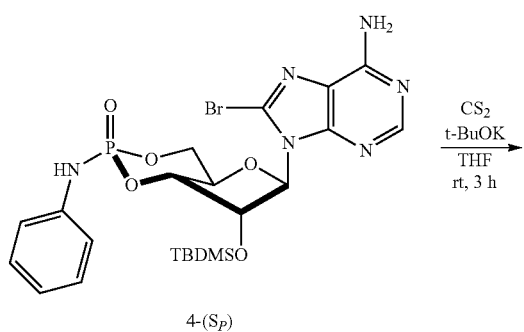

4-(S_P)

27 28
-continued
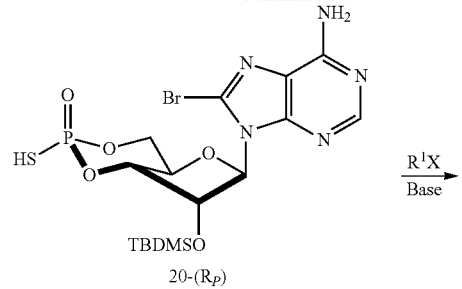
20-($R_P$)
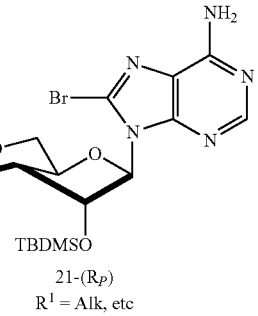
21-($R_P$)
$R^1$ = Alk, etc
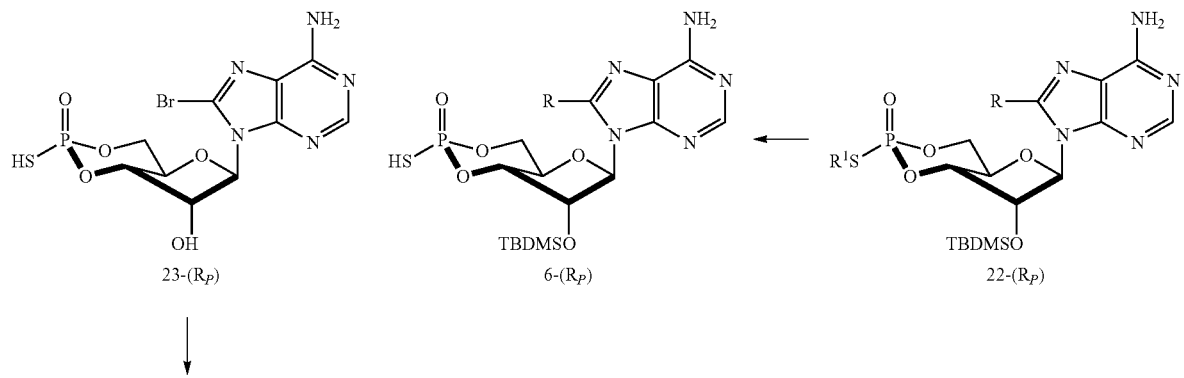
23-($R_P$)     6-($R_P$)     22-($R_P$)
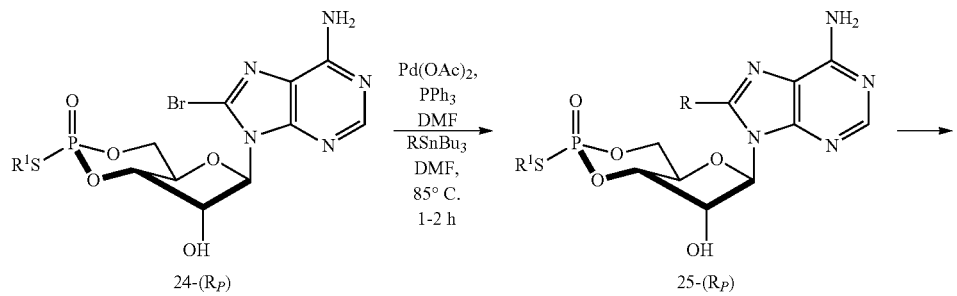
24-($R_P$)     25-($R_P$)
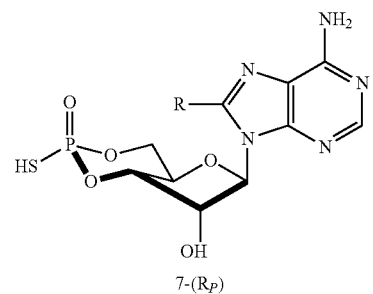
7-($R_P$)

As mentioned above, it may be desirable to use the compounds of the invention in prodrug form. Typical such prodrugs may be produced by S-alkylation and two reaction schemes for S-alkylation are set out as Schemes and 12 below. Schemes 11 and 12 describe reaction of the phosphorothioate with an alkyl halide, or more specifically a haloalkyl carboxylate.

Scheme 11

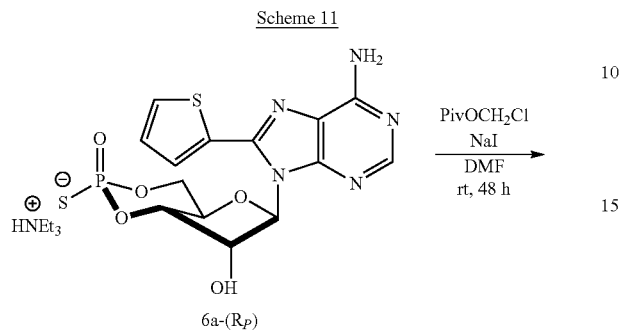

6a-(R$_P$)

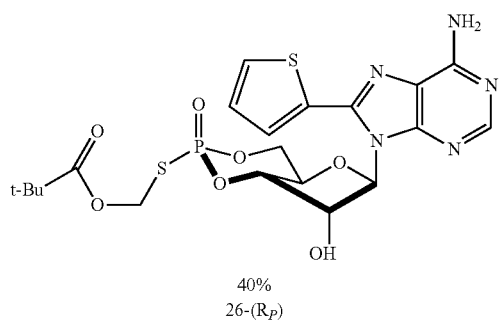

40%
26-(R$_P$)

Scheme 12

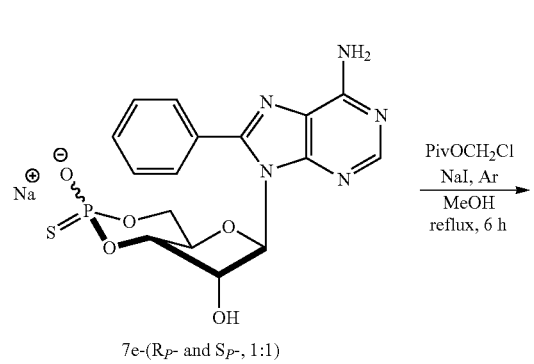

7e-(R$_P$- and S$_P$-, 1:1)

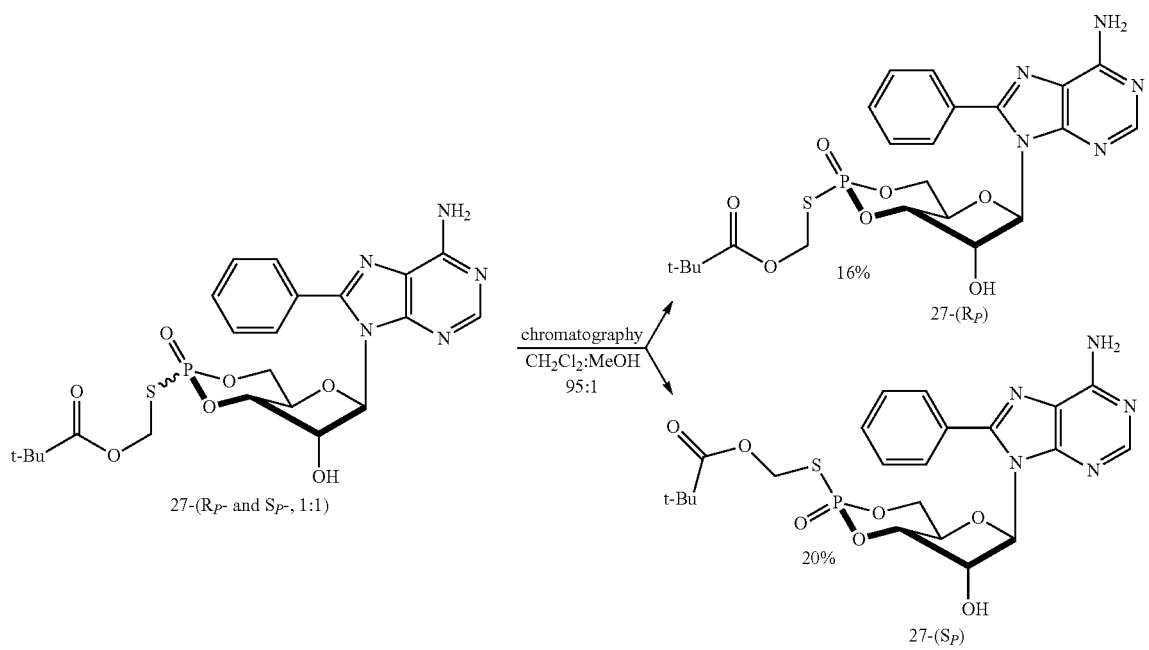

27-(R$_P$- and S$_P$-, 1:1)

27-(R$_P$)  16%

27-(S$_P$)  20%

Various of the intermediates in the process schemes discussed above are novel and themselves form further aspects of the invention.

The hydrophilic 8-substituted cAMPS compounds of the invention are preferably purified by transformation into their soluble trialkylammonium (e.g. tributylammonium) salts followed by flash chromatography, e.g. on silica gel. Such alkylammonium salts may be prepared by mixing the ammonium salts with an alkylamine and evaporating off ammonia. The resultant product may then if desired be transformed into alternative salt form, e.g. sodium salt form, prior to use.

The conditions and reagents used in these processes are only exemplary. Other reagents, solvents and reaction conditions can also be used, especially when these processes are used industrially to produce pharmaceuticals. A skilled chemist with a background in development chemistry will routinely improve these processes by selection of conditions, reagents and solvents with focus on: cost, safety, hazard, toxicity, environment and regulatory aspects.

Thus viewed from a further aspect the invention provides an 8-carbylated adenosine cyclic 3',5'-phosphoramidate or a derivative thereof.

Viewed from a still further aspect the invention provides an 8-carbylated-2'-protected (e.g. silylated) adenosine cyclic 3',5'-phosphorothioate or a derivative thereof.

Viewed from another aspect the invention provides an 8-halo (and preferably 2'-protected (e.g. silylated)) adenosine cyclic 3',5'-phosphoramidate or a derivative thereof.

Viewed from a still further aspect the invention provides an 8-carbylated adenosine cyclic 3',5'-monophosphite or a derivative thereof.

Viewed from a further aspect the invention provides a pharmaceutical composition comprising an 8-carbylated cAMPS or a derivative thereof together with a physiologically tolerable carrier or recipient.

The composition of the invention may take any convenient administration form, e.g. tablet, capsule, powder, syrup, spray, solution, dispersion, suppository, etc. The active agent will be admixed with a suitable carrier or excipient, e.g. a solvent (such as water for injections), diluents, stabilizers, viscosity modifiers, pH modifiers, aromas, flavours, antioxidants, etc. and the composition may be prepared in conventional fashion.

Viewed from a still further aspect the invention provides a method of treatment of the human or non-human animal (preferably mammalian) body to achieve a cAMP agonist or antagonist effect therein, said method comprising administering to said body an effective amount of an 8-carbylated cAMPS or derivative thereof according to the invention.

The method of treatment is especially preferably for treatment of neoplastic diseases, immunodeficiencies and viral infections, especially HIV infection.

Viewed from a further aspect the invention provides the use of an 8-carbylated cAMPS or derivative thereof according to the invention for the manufacture of a medicament for use in a method of treatment of the human or non-human animal (preferably mammalian) body to achieve a cAMP agonist or antagonist effect therein.

The dosage of the 8-carbylated cAMPS or derivative will depend on the nature of the condition being treated as well as the size, sex and species of the recipient. In general daily dosages for human subjects in particular will be of the order of 0.01 to 100 mg/kg bodyweight. Administration is preferably orally or iv.

Because of their cAMP agonist/antagonist properties, the 8-carbylated cAMPS and derivatives of the invention may be used in competitive binding assays for cAMP, e.g. in biological samples. One such assay is described in WO 2004/027074. In such assays the 8-carbylated cAMPS is preferably labelled (e.g. radiolabelled or chromophore labelled) and may conveniently be substrate-bound.

Thus viewed from a further aspect the invention provides an assay method for determining cAMP in a sample, generally a biological sample, which method involves contacting said sample with a cAMP-analog and a cAMP binding reagent, characterized in that said analog is an 8-carbylated cAMPS or derivative thereof.

The invention is applicable to other purine nucleotides than adenosine, in particular guanosine, and adenosine and guanosine analogs including their di- and tri-aza analogs, e.g. the annular di- and tri-aza analogs (for example annulated imidazo-pyridines, benzimidazole and annulated pyrrolo-pyrimidines and pyrrolo-pyridines) such as 1-deazapurine, 3-deazapurine, 7-deazapurine and 1,3-deazapurine, and in further aspects of the invention the definitions and experimental teaching contained herein may be applied mutatis mutandi to such other purine nucleotides which may of course be substituted at other skeletal positions analogously to the 8-carbylated cAMPS described above. Such 8-carbylated non-adenosine purine cyclic 3',5' phosphorothioates may be used therapeutically in applications applicable to the particular nucleotide, e.g. for treatment of virus infections, immune deficiencies and neoplastic diseases.

One aspect of the present invention is the use of a combination of the present cAMP antagonists/agonists with other drugs that have an effect on the immune system.

Another aspect of the present invention relates to a combination of the present cAMP antagonists/agonists with other drugs useful for treatment of HIV infections and neoplastic diseases.

A key reagent in the preparation of many of the compounds according to the invention is 8-Br-cAMP. Up until now, reports in the literature only refer to small scale preparations (e.g. <100 mg) of this material using dilute (0.1M) solutions of cAMP in an acetic acid/acetate medium. Attempts to use similar dilute conditions in larger scale work resulted in problems due to the large volumes of solvent required. We have now found that the procedure may be scaled up using concentrated solutions of cAMP with a concentrated buffer to scavenge the HBr that is produced during the reaction of cAMP with bromine. By using concentrated cAMP solutions, a two-fold benefit is also achieved—the proportion of the 8-Br-cAMP product that is precipitated out as if forms is optimised (thus making product collection easier) and the cAMP(H) starting material contributes to the buffer system. Thus for example 0.2M cAMP(H) and 0.4M sodium acetate creates a buffer system equivalent to 0.2M NaOAc/AcOH with a pH which remains stable during the bromination at about 4.7.

Such a process forms a further aspect of the invention. Viewed from this aspect the invention provides a process for the preparation of 8-Br-cAMP which comprises reacting cAMP with bromine in a buffered solution (preferably aqueous), reacting with a reducing agent (e.g. sodium sulphite) to remove excess bromine, collecting the 8-Br-cAMP produced, and optionally removing free bromine from the collected 8-Br-cAMP, wherein cAMP is used in concentrated solution form (e.g. 0.15 to 0.6M, preferably 0.16 to 0.3M, especially 0.17 to 0.25M) and the buffer (e.g. an acetate buffer) is sufficiently concentrated to maintain a solution pH which is in the range 3.5 to 5.5, especially 4 to 5. In this process, the bromine is preferably added slowly and the reducing agent is also subsequently added slowly. This process is exemplified in Example 47 below.

The invention will now be described further with reference to the following non-limiting Examples.

EXAMPLE 1

8-Bromo-2'O-(tert-butyldimethylsilyl)adenosine-3', 5'-cyclic phosphate tributylammonium salt (2)

TBDMS-Cl (2.72 g, 18 mmol) was added to a solution of 8-bromo-cAMP tributylammonium salt (1) (7.0 g, 11.8 mmol) and imidazole (2.45 g, 36 mmol) in DMF (30 ml) at room temperature. The mixture was stirred at 50° C. for 48 h under argon. The solvent was removed at reduced pressure, the crude product suspended in water (150 ml), and 1.2 M HCl (76 ml) was added. The precipitate was filtered off, washed with water and dried under vacuum. The acid was suspended in MeOH (80 ml) and Bu$_3$N (5 ml) was added. The mixture was stirred at room temperature for 3 h, the solvent distilled off and the product dried under vacuum; yield 6.50 g (78%) of a white solid. $^1$H NMR (DMSO-d$_6$, 300 MHz): δ 0.01 (3H, s, Si—CH$_3$), 0.03 (3H, s, Si—CH$_3$), 0.83 (9H, s, Si-t-Bu), 0.87 (9H, t), 1.28 (6H, m), 1.53 (6H, m), 2.79 (6H, m), 3.90 (2H, m), 4.11 (1H, m), 5.02 (2H, m), 7.53 (2H, s, NH$_2$), 8.15 (1H, s, H-2) $^{13}$C NMR (DMSO-d$_6$, 75 MHz): δ −5.3, −4.7, 13.6, 18.0, 19.6, 25.6, 25.7, 51.9, 65.4, 72.3, 72.4, 76.2, 94.3, 119.2, 126.5, 150.0, 153.2, 155.0. $^{31}$P NMR (CDCl$_3$, 81 MHz): δ −1.36. HRMS (Electrospray)): Found negative ions: M 520.0427. Calc. 520.0422.

EXAMPLE 2

(S$_p$)-8-Bromadenosine-2'O-(tert-butyldimethylsilyl)-3',5'-cyclic N-phenylphosphoramidate (4)

A solution of 8-bromadenosine-2'O-(tert-butyldimethylsilyl)-3',5'-cyclic phosphate tributylammonium salt (2) (500 mg, 0.71 mmol) in CH$_2$Cl$_2$ (7 ml) was added dropwise to a solution of oxalyl chloride (0.24 ml, 2.8 mmol) and DMF (1 drop) in CH$_2$Cl$_2$ (15 ml) at 0° C. The mixture was stirred at room temperature for 30 min before the solvent was removed under vacuum. The crude product was redissolved in CH$_2$Cl$_2$ (20 ml) and aniline (0.5 ml, 4.26 mmol) added dropwise at 0° C., and the mixture stirred at room temperature overnight. The solvent was evaporated and the residue purified by flash chromatography using CH$_2$Cl$_2$:MeOH (3:97 and 5:95) for elution; yield 125 mg (29%) of a white solid. $^1$H NMR (DMSO-d$_6$, 300 MHz): δ −0.09 (3H, s, Si—CH$_3$), 0.02 (3H, s, Si—CH$_3$), 0.79 (9H, s, Si-t-Bu), 4.4 (2H, m), 4.65 (1H, m), 5.12 (1H, d), 5.52 (1H, m), 5.92 (1H, s), 6.93 (1H, t), 7.10 (2H, d), 7.20 (2H, t), 7.56 (2H, s, NH$_2$), 8.23 (1H, s, H-2), 8.55 (1H, d, Ar—NH). $^{13}$C NMR (DMSO-d$_6$, 75 MHz): δ −5.2-5.0, 17.8, 24.9, 68.2, 70.4, 72.3, 76.1, 92.9, 117.7, 118.5, 121.8, 128.9, 135.9, 139.5, 149.7, 153.4, 155.1. $^{31}$P NMR (DMSO-d$_6$, 81 MHz): δ 2.28.

EXAMPLE 3

(S$_p$)-8-(2-Furyl)adenosine-2'O-(tert-butyldimethylsilyl)-3', 5'-cyclic N-phenylphosphoramidate (5a)

A solution of Pd(OAc)$_2$ (99 mg, 0.37 mmol) and PPh$_3$ (253 mg, 0.81 mmol) in DMF (15 ml) was stirred at 50° C. for 15 min before tri-n-butyl(2-furyl)stannane (1.4 ml, 4.4 mmol) was added. Thereafter was added a solution of (S$_p$)-8-bromadenosine-2'O-(tert-butyldimethylsilyl)-3', 5'-cyclic N-phenylphosphoramidate (4) (2.2 g, 3.7 mmol) in DMF (10 ml). The mixture was stirred at 80° C. for 1 h. The solvent was evaporated and the residue purified by flash chromatography using CH$_2$Cl$_2$:MeOH 3:97 and 5:95 as eluant; yield 1.93 g (90%) of a white solid. $^1$H NMR (DMSO-d$_6$, 300 MHz): δ −0.14 (3H, s, Si—CH$_3$), −0.11 (3H, s, Si—CH$_3$), 0.70 (9H, s, Si-t-Bu), 4.4-4.5 (2H, m), 4.65 (1H, dm), 5.19 (1H, d), 5.65 (1H, m), 6.31 (1H, s), 6.77 (1H, dd), 6.93 (1H, t), 7.1-7.2 (5H, m), 7.58 (2H, br. s), 8.00 (1H, d), 8.27 (1H, s), 8.56 (1H, d) $^{13}$C NMR (DMSO-d$_6$, 75 MHz): δ −5.6, −5.0, 17.7, 25.3, 68.3, 70.2, 72.4, 76.3, 93.6, 112.3, 113.9, 118.45, 121.8, 128.9, 139.6, 140.3, 143.2, 145.6, 149.8, 153.4, 156.1. $^{31}$P NMR (CDCl$_3$, 81 MHz): δ 3.06. HRMS (Electrospray, TOF ES)—positive ions: M 585.2023. Calc 585.2041.

EXAMPLE 4

(S$_p$)-8-(2-Thienyl)adenosine-2'O-(tert-butyldimethylsilyl)-3',5'-cyclic N-phenylphosphoramidate (5b)

A solution of Pd(OAc)$_2$ (117 mg, 0.44 mmol) and PPh$_3$ (299 mg, 0.96 mmol) in DMF (15 ml) was stirred at 50° C. for 30 min before tri-n-butyl(2-thienyl)stannane (2.2 ml, 6.8 mmol) was added. Thereafter a solution of (S$_p$)-8-bromadenosine-2'O-(tert-butyldimethylsilyl)-3',5'-cyclic N-phenylphosphoramidate (4) (2.72 g, 4.6 mmol) in DMF (10 ml) was added. The mixture was stirred at 85° C. for 1 h. The solvent was evaporated and the residue purified by flash chromatography on silica gel using CH$_2$Cl$_2$:MeOH 3:97 and 5:95 as eluant; yield 1.91 g (71%) of a white solid. $^1$H NMR (DMSO-d$_6$, 200 MHz): δ −0.18 (3H, s, Si—CH$_3$), −0.17 (3H, s, Si—CH$_3$), 0.63 (9H, s, Si-t-Bu), 4.4-4.5 (2H, m), 4.69 (1H, dm), 5.23 (1H, d), 5.55 (1H, m), 5.97 (1H, s), 6.93 (1H, t), 7.0-7.2 (4H, m), 7.31 (1H, dd), 7.55 (3H, br. m), 7.90 (1H, dd), 8.26 (1H, s), 8.56 (1H, d). $^{13}$C NMR (DMSO-d$_6$, 50 MHz): δ −5.6, −5.0, 17.7, 25.3, 68.3, 70.2, 71.9, 76.5, 93.6, 118.3, 118.5, 118.7, 121.8, 128.3, 128.9, 129.4, 129.7, 130.6, 139.5, 143.9, 150.1, 153.3, 155.9. $^{31}$P NMR (DMSO-d$_6$, 81 MHz): δ 2.41.

EXAMPLE 5

(S$_p$)-8-(3-Furyl)adenosine-2'O-(tert-butyldimethylsilyl)-3',5'-cyclic N-phenylphosphoramidate (5c)

A solution of Pd(OAc)$_2$ (133 mg, 0.50 mmol) and PPh$_3$ (342 mg, 1.1 mmol) in DMF (20 ml) was stirred at 50° C. for 30 min before tri-n-butyl(3-furyl)stannane (2.67 g, 7.5 mmol) was added. Thereafter a solution of (S$_p$)-8-bromadenosine-2'O-(tert-butyldimethylsilyl)-3',5'-cyclic N-phenylphosphoramidate (4) (3.00 g, 5.0 mmol) in DMF (10 ml) was added. The mixture was stirred at 85° C. for 2 h. The solvent was evaporated and the residue purified by flash chromatography using CH$_2$Cl$_2$:MeOH 3:97 and 5:95 as eluant; yield 2.70 g (92%) of a white solid. $^1$H NMR (DMSO-d$_6$, 200 MHz): δ −0.16 (s, 3H, Si—CH$_3$), −0.14 (3H, s, Si—CH$_3$), 0.66 (9H, s, Si-t-Bu), 4.4-4.5 (2H, m), 4.65 (1H, dm), 5.26 (1H, d), 5.44 (1H, m), 5.86 (1H, s), 6.9-7.0 (2H, m), 7.0-7.2 (4H, m), 7.48 (2H, br. s), 7.96 (1H, t), 8.24 (1H, s), 8.29 (1H, s), 8.57 (1H, d). $^{13}$C NMR (DMSO-d$_6$, 50 MHz): δ −5.5, −5.0, 17.7, 25.3, 68.3, 70.0, 71.8, 76.5, 93.4, 110.4, 114.9, 118.4, 118.5, 118.7, 121.8, 128.9, 139.5, 143.2, 143.5, 145.0, 149.9, 153.1, 155.9. $^{31}$P NMR (DMSO-d$_6$, 81 MHz): δ 2.43.

EXAMPLE 6

(S$_p$)-8-(3-Thienyl)adenosine-2'O-(tert-butyldimethylsilyl)-3',5'-cyclic N-phenylphosphoramidate (5d)

A solution of Pd(OAc)$_2$ (0.008 g, 0.03 mmol) and PPh$_3$ (0.02 g, 0.07 mmol) in dioxane (3 ml). was flushed under argon. The mixture was stirred at 50° C. for 25 min when the reaction mixture had become reddish-brown. A solution of ($S_p$)-8-bromadenosine-2'O-(tert-butyldimethylsilyl)-3',5'-cyclic N-phenylphosphoramidate (4) (0.10 g, 0.17 mmol), 3-thiopheneboronic acid (0.03 g, 0.25 mmol) and $Cs_2CO_3$ (0.16 g, 0.50 mmol) in water was added. The temperature was increased to 95° C., stirred for 4.5 h. The resultant solution was cooled, diluted with THF (15 ml) and washed with saturated $NaHCO_3$ (10 ml). The organic phase was separated and dried with $MgSO_4$. The filtrate was evaporated to dryness under reduced pressure and the product isolated from the residual material after flash chromatography using 3% MeOH in EtOAc; yield 50% of a tan solid. $^1$H NMR: (300 MHz, DMSO-$d_6$); δ −0.18 (6H, s, 2×$SiCH_3$), 0.63 (9H, s, 3×$SiCCH_3$), 4.39-4.73 (3H, m), 5.16 (1H, d, J 5.2 Hz), 5.53-5.58 (1H, m), 5.86 (1H, s), 6.91-7.23 (5H, m, Ph-H), 7.46 (1H, dd, J 1.2 Hz, J' 5.0 Hz, H-4"), 7.50 (2H, s, $NH_2$), 7.85 (1H, dd, J 2.9 Hz, J' 5.0 Hz, H-5"), 8.04 (1H, dd, J 1.2 Hz, J' 2.9 Hz, H-2"), 8.26 (1H, s, H-2), 8.56 (1H, d, J 8.9 Hz, NH-Ph).

EXAMPLE 7

($R_p$)-8-(2-Furyl)adenosine-2'O-(tert-butyldimethylsilyl)-3',5'-cyclic phosphorothioic acid (6a)

A 1.0 M solution of t-BuOK in THF (3.6 ml, 3.6 mmol) was added to a solution of ($S_p$)-8-(2-furyl)adenosine-2'O-(tert-butyldimethylsilyl)-3',5'-cyclic N-phenylphosphoramidate (5a) (1.51 g, 2.6 mmol) in THF (30 ml) at room temperature. The mixture was stirred for 1 h at this temperature before $CS_2$ (0.47 ml, 7.8 mmol) was added and the mixture stirred for another 3 h at room temperature. The volume of the solvent was reduced to about 10 ml before hexane (90 ml) was added. A precipitate was formed and was collected by filtration, suspended in water (55 ml) and 1.2 M HCl (9 ml) added. The product was collected by filtration, washed with water and dried; yield 1.23 g (91%) of a light tan solid. $^1$H NMR (DMSO-$d_6$, 300 MHz): δ −0.03 (3H, s, Si—$CH_3$), 0.04 (3H, s, Si—$CH_3$), 0.79 (9H, s, Si-t-Bu), 4.0-4.5 (3H, m), 5.06 (1H, d), 5.34 (1H, m), 6.21 (1H, s), 6.79 (1H, q), 7.18 (1H, d), 8.02 (1H, s,), 8.2 (2H, br. s,), 8.33 (1H, s). $^{13}$C NMR (DMSO-$d_6$, 75 MHz): δ −5.4, −4.6, 17.9, 25.5, 67.7, 71.1, 72.8, 75.9, 93.2, 112.4, 114.4, 119.1, 141.3, 142.8, 146.0, 149.4, 150.2, 153.7. $^{31}$P NMR (DMSO-$d_6$, 81 MHz): δ 58.4. HRMS (electrospray): M 526.1326. Calc. for $C_{20}H_{28}N_5O_6PSSi$: 526.1339.

EXAMPLE 8

($R_p$)-8-(2-Thienyl)adenosine-2'O-(tert-butyldimethylsilyl)-3',5'-cyclic phosphorothioic acid (6b)

A 1.0 M solution of t-BuOK in THF (3.8 ml, 3.8 mmol) was added to a solution of (Sp)-8-(2-thienyl)adenosine-2'O-(tert-butyldimethylsilyl)-3',5'-cyclic N-phenylphosphoramidate (5b) (1.87 g, 3.1 mmol) in THF (35 ml) at room temperature. The mixture was stirred for 1 h before $CS_2$ (0.57 ml, 9.5 mmol) was added and the mixture stirred for another 3 h at room temperature. The volume of the solvent was reduced to about 10 ml before hexane (90 ml) was added. A precipitate was formed and was collected by filtration, suspended in water (55 ml) and 1.2 M HCl (10 ml) added. The product was collected by filtration, washed with water and dried; yield 1.54 g (91%) of a light tan solid. $^1$H NMR (DMSO-$d_6$, 300 MHz): δ −0.07 (3H, s, Si—$CH_3$), 0.03 (3H, s, Si—$CH_3$), 0.73 (9H, s, Si-t-Bu), 4.1-4.5 (3H, m), 5.13 (1H, d), 5.28 (1H, m), 5.92 (1H, s), 7.31 (1H, q), 7.60 (1H, d), 7.94 (1H, d), 8.37 (1H, s). $^{13}$C NMR (DMSO-$d_6$, 75 MHz): δ −5.3, −4.5, 17.8, 25.5, 67.5, 71.2, 72.5, 76.0, 93.3, 118.9, 128.4, 128.6, 129.4, 129.8, 131.0, 145.2, 149.8, 153.4. $^{31}$P NMR (DMSO-$d_6$, 81 MHz): δ 58.18.

EXAMPLE 9

($R_p$)-8-(3-Furyl)adenosine-2'O-(tert-butyldimethylsilyl)-3',5'-cyclic phosphorothioic acid (6c)

A 1.0 M solution of t-BuOK in THF (5.3 ml, 5.3 mmol) was added to a solution of (Sp)-8-(3-furyl)adenosine-2'O-(tert-butyldimethylsilyl)-3',5'-cyclic N-phenylphosphoramidate (5c) (2.58 g, 4.4 mmol) in THF (35 ml) at room temperature. The mixture was stirred for 1 h before $CS_2$ (0.80 ml, 13.3 mmol) was added and the mixture stirred for another 3 h at room temperature. The volume of the solvent was reduced to about 10 ml before hexane (90 ml) was added. A precipitate was formed and was collected by filtration, suspended in water (55 ml) and 1.2 M HCl (10 ml) was added. The product was collected by filtration, washed with water and dried; yield 1.95 g (84%) of a light tan solid. $^1$H NMR (DMSO-$d_6$, 300 MHz): δ −0.057 (3H, s, Si—$CH_3$), 0.033 (3H, s, Si—$CH_3$), 0.76 (9H, s, Si-t-Bu), 4.1-4.5 (3H, m), 5.13 (1H, d), 5.20 (1H, m), 5.81 (1H, s), 6.90 (1H, d), 7.97 (1H, d), 8.29 (1H, s), 8.37 (1H, s). $^{13}$C NMR (DMSO-$d_6$, 75 MHz): δ −5.3, −4.5, 17.9, 25.5, 67.5, 71.0, 72.3, 76.0, 93.1, 110.4, 114.6, 118.8, 143.8, 144.7, 145.1, 149.5, 152.0, 153.2. $^{31}$P NMR (DMSO-$d_6$, 81 MHz) δ 58.08.

EXAMPLE 10

($R_p$)-8-(2-Furyl)adenosine-3',5'-cyclic phosphorothioic acid ammonium salt (7a)

A solution of ($R_p$)-8-(2-furyl)adenosine-2'O-(tert-butyldimethylsilyl)-3',5'-cyclic phosphorothioic acid (6a) (1.15 g, 2.7 mmol) and $NH_4F$ (225 mg, 6.0 mmol) in DMF (10 ml) was stirred at room temperature for 5 days. Subsequently TMSOMe (1 mL) was added and the stirring continued for 24 h. The solvent was distilled off at reduced pressure, the crude product suspended in MeOH (10 ml) and $Et_2O$ (80 ml) added. The light tan coloured solid was filtered off and dried; yield 847 mg (90%). $^1$H NMR (DMSO-$d_6$, 300 MHz): δ 4.0-4.2 (4H, m), 5.03 (1H, d), 5.14 (1H, m), 6.02 (1H, s), 6.76 (1H, dd), 7.13 (1H, d), 8.01 (1H, d), 8.21 (1H, s). $^{13}$C NMR (DMSO-$d_6$, 75 MHz): δ 66.2, 75.3, 76.9, 75.4, 92.8, 112.3, 113.8, 118.9, 141.2, 143.1, 145.8, 149.8, 152.7, 155.6. $^{31}$P NMR (DMSO-$d_6$, 81 MHz): δ 54.3. HRMS (Electrospray, TOF ES)—negative ions: M 410.0330. Calc. 410.0329.

EXAMPLE 11

($R_p$)-8-(2-Thienyl)adenosine-3',5'-cyclic phosphorothioic acid ammonium salt (7b)

A solution of ($R_p$)-8-(2-thienyl)adenosine-2'O-(tert-butyldimethylsilyl)-3',5'-cyclic phosphorothioic acid (6b) (1.33 g, 2.5 mmol) and $NH_4F$ (281 mg, 7.5 mmol) in DMF (15 ml) was stirred at room temperature for 5 days. Subsequently TMSOMe (1 ml) was added and the stirring continued for 24 h. The solvent was distilled off at reduced pressure, the crude product suspended in MeOH (10 ml) and $Et_2O$ (80 ml) added. The light tan coloured solid was filtered off and dried; yield 934 mg (86%) of a light tan solid. $^1$H NMR ($CD_3OD$, 200 MHz): δ 4.2-4.4 (3H, m), 5.20 (1H, d), 5.5 (1H, m), 6.00 (1H, s), 7.27 (1H, dd), 7.69 (1H, d), 7.75 (1H, d), 8.21 (1H, s). $^{13}$C NMR (CD$_3$OD, 75 MHz): δ 68.5, 72.6, 73.2, 77.8, 94.2, 120.0, 129.3, 131.1, 131.2, 147.1, 151.8, 154.0, 156.8. $^{31}$P NMR (CD$_3$OD, 81 MHz): δ 58.0.

EXAMPLE 12

(R$_p$)-8-(3-Furyl)adenosine-3',5'-cyclic phosphorothioic acid ammonium salt (7c)

A solution of (R$_p$)-8-(3-furyl)adenosine-2'O-(tert-butyldimethylsilyl)-3',5'-cyclic phosphorothioic acid (6c) (1.9 g, 3.6 mmol) and NH$_4$F (404 mg, 10.8 mmol) in DMF (20 ml) was stirred at room temperature for 5 days. Subsequently TMSOMe (1 ml) was added and the stirring continued for 24 h. The solvent was distilled off at reduced pressure, the crude product suspended in MeOH (10 ml) and Et$_2$O (80 ml) added. The light tan coloured solid was filtered off and dried; yield 1.38 g (89%) of a light tan solid. $^1$H NMR (CD$_3$OD, 300 MHz): δ 4.2-4.4 (3H, m), 5.24 (1H, d), 5.42 (1H, m), 5.88 (1H, s), 6.89 (1H, d), 7.69 (1H, t), 8.11 (1H, s), 8.18 (1H, s). $^{13}$C NMR (CD$_3$OD, 75 MHz): δ 68.5, 72.4, 73.1, 77.7, 93.9, 111.3, 116.4, 119.9, 144.9, 145.8, 146.7, 151.4, 153.0, 156.2. $^{31}$P NMR (DMSO-d$_6$, 81 MHz): δ 54.3.

EXAMPLE 13

(R$_p$)-8-Phenyladenosine-3',5'-cyclic phosphorothioic acid (7e)

8-Phenyladenosine (17e) (0.343 g, 1 mmol) was dried by repeated azeotropic distillation with pyridine and then dissolved in pyridine (10 ml) which had been freshly distilled from calcium hydride under argon gas on a continuous still. Thiophosphoryl chloride (0.169 g, 1 mmol) in dry THF (2 ml) was added to the above pyridine solution under an argon atmosphere at −12° C. over 10 min. The mixture was stirred at −12° C. for 15 min before the reaction mixture was added to a vigorously stirred solution of sodium hydroxide (0.240 g, 6 mmol) in water (40 ml) at 60° C. and thereafter rapidly poured onto crushed dry ice. When the evolution of carbon dioxide had ceased, the solvents were distilled off at reduced pressure. The bath temperature during the distillation was not allowed to exceed 35° C. The solid residue was washed repeatedly with diethyl ether, extracted into methanol (5 ml), the mixture filtered and the filtrate added slowly with vigorous stirring to THF (100 ml). Filtration through celite and evaporation of the filtrate at reduced pressure left a solid material. The product was a 1:1 mixture of the (R$_p$)- and the (S$_p$)-8-phenyladenosine-3',5'-cyclic phosphorothioic diastereoisomers. The isomers were separated chromatographically when the mixture was subjected to preparative reversed phase chromatography on a C18-functionalised silica gel column using as eluent water:methanol:formic acid 80:20:0.5. Physical data for the title compound: MS (Electrospray; negative ESI, m/z): 863.1 (8%, 2 M+Na-2H), 420 (100%, M−1) 210.1 (35%). $^{31}$PNMR (CD$_3$OD) (sodium salt): 57.8 ppm. The (S$_p$)-8-phenyladenosine-3',5'-cyclic phosphorothioic acid (7e) isomer is similarly available after the HPLC-separation.

EXAMPLE 14

2',3',5'-Tris-(O-acetyl)-8-bromoadenosine (12)

Acetic anhydride (5.66 ml, 60 mmol) was added dropwise to a solution of 8-bromoadenosine (11) (3.46 g, 10 mmol) in pyridine (50 ml) followed by DMAP (1 mmol) and the mixture stirred at room temperature for 5 h. The reaction was quenched by addition of methanol (10 ml). The solution was evaporated to dryness at reduced pressure, the residual material dissolved in ethyl acetate (250 ml), the solution shaken with NaHCO$_3$ (100 ml), water (3×50 ml), dried (MgSO$_4$) and the solution concentrated at reduced pressure. The product was a solid; yield 3.21 g, (68%).

EXAMPLE 15

2',3',5'-Tris-(O-tert-butyldimethylsilyl)-8-bromoadenosine (13)

TBDMS-Cl (2.30 g, 15.0 mmol) was added to a solution of 8-bromoadenosine (11) (1.32 g, 3.82 mmol) and imidazole (2.08 g, 30.5 mmol) in DMF (15 ml) and the solution stirred at room temperature for 24 h. Saturated aqueous NH$_4$Cl (35 ml) was added and the mixture extracted with EtOAc (2×40 ml). The organic extracts were washed with water (2×15 ml), dried (MgSO$_4$) and evaporated to provide the title compound; yield 2.16 g (82%).

EXAMPLE 16

2',3',5'-Tris-(O-acetyl)-8-phenyladenosine (14a)

2',3',5'-Tris-(O-acetyl)-8-bromoadenosine (12) (0.89 g, 1.88 mmol), TFP (0.17 g, 0.75 mmol) and Pd$_2$dba$_3$*CHCl$_3$ (0.10 g, 0.10 mmol) were dissolved in DMF (14 ml) under argon and the solution heated to 50° C. when Bu$_3$SnPh (0.61 ml, 1.88 mmol) was added dropwise. The reaction mixture was heated at 110° C. for 20 h and evaporated to dryness at reduced pressure. The product was isolated from the residual material after flash chromatography on silica gel using EtOAc:MeOH 99:1; yield 0.75 g (85%). HRMS: M 469.1581. Calc. for C$_{22}$H$_{23}$N$_5$O$_7$: 469.1597. MS (EI): M 469 (M, 12%), 259 (25), 212 (27), 211 (68), 139 (40), 104 (9), 97 (18), 43 (100).

EXAMPLE 17

2',3',5'-Tris-(O-acetyl)-8-(2-furyl)adenosine (14b)

2-(Tributylstannyl)furan (12) (1.52 ml, 4.84 mmol) was added to a solution of. 2',3',5'-tris-(O-acetyl)-8-bromoadenosine (1.90 g, 4.03 mmol), TFP (0.37 g, 1.61 mmol) and Pd$_2$dba$_3$*CDCl$_3$ (0.21 g, 0.20 mmol) in DMF (30 ml) under argon at 50° C. The reaction mixture was heated at 110° C. overnight, the solution evaporated at reduced pressure and the title material isolated from the residual material after flash chromatography on silica gel using EtOAc:MeOH, 99:1; yield 1.61 g (87%). HRMS: M 458.1402. Calc. for C$_{20}$H$_{21}$N$_5$O$_8$: 459.1390. MS (EI): 460 (M, 5%), 459 (21), 259 (19), 202 (25), 201 (100), 174 (9), 157 (6), 139 (35), 97 (19), 43 (59).

EXAMPLE 18

2',3',5'-Tris-(O-acetyl)-8-(3-furyl)adenosine (14c)

3-Tributylstannylfuran (1.36 g, 3.81 mmol) was added dropwise at room temperature to a solution of 2',3',5'-tris-(O-acetyl)-8-bromadenosine (12) (1.50 g, 3.18 mmol), TFP (0.30 g, 1.27 mmol) and Pd$_2$dba$_3$*CHCl$_3$ (0.16 g, 0.16 mmol) in DMF (22.5 ml) under argon at 50° C. The temperature was increased to 110° C. and the reaction mixture stirred overnight at this temperature. The solvent was removed at reduced pressure and the residual material subjected to flash chromatography on silica gel using EtOAc:MeOH 99:1; yield 1.25 g (86%). HRMS: M 459.1384. Calc. for $C_{20}H_{21}N_5O_8$: 459.1390. $^1$H NMR: (300 MHz, CDCl$_3$); δ 1.97/2.01/2.08 (9H, s, 3×COCH$_3$), 4.26-4.48 (3H, m, H-5', C-4'), 5.97-6.02 (2H, m, H-1', H-3'), 6.31 (2H, s, NH$_2$), 6.58 (1H, dd, J 4.4 Hz, J' 5.8 Hz, H-2'), 6.81-6.82 (1H, m, furyl-H), 7.53-7.54 (1H, m, furyl-H), 7.93-7.94 (1H, m, furyl-H), 8.27 (1H, s, H-2). $^{13}$C NMR: (75 MHz, CDCl$_3$): δ 20.4/20.46/2.5 (3×COCH$_3$), 62.8 (C-5'), 70.7/71.9/80.1/87.4 (C-2', C-3', C-1', C-4'), 110.7/115.3 (C-4'', C-3''), 119.5 (C-5), 143.3/144.0/145.0/150.5/152.7/155.3 (C-2'', C-5'', C-8, C-6, C-2, C-4), 169.3/169.4/170.5 (3×COCH$_3$). MS (EI): 460 (M, 6%), 459 (28), 260 (6), 259 (54), 202 (34), 201 (100), 139 (81), 97 (39), 43 (92).

EXAMPLE 19

2',3',5'-Tris-(O-acetyl)-8-(2-thienyl)adenosine (14d)

2-(Tributylstannyl)thiophene (0.40 ml, 1.27 mmol) was added dropwise to a solution of 2',3',5-tris-(O-acetyl)-8-bromoadenosine (12) (0.50 g, 1.06 mmol), TFP (0.10 g, 0.42 mmol) and Pd$_2$dba$_3$*CHCl$_3$ (0.05 g, 0.05 mmol) in DMF (9 ml) under argon at 50° C. The resultant mixture was heated at 110° C. with stirring overnight. The mixture was evaporated to dryness at reduced pressure and the title compound isolated after flash chromatography of the residual material using EtOAc:MeOH 99:1; yield >80%. HRMS: M 475.1158. Calc. for $C_{20}H_{21}N_5O_7S$: 475.1162. MS (EI): 476 (M, 3%), 475 (14), 260 (7), 259 (31), 219 (6), 218 (20), 217 (100), 190 (7), 157 (9), 139 (42), 97 (21).

EXAMPLE 20

2',3',5'-Tris-(O-acetyl)-8-(1-methyl-2-pyrrolyl)adenosine (14e)

2',3',5'-Tris-(O-acetyl)-8-bromoadenosine (12) (1.50 g, 3.18 mmol), tris(2-furyl)phosphine (0.29 g, 1.27 mmol) and Pd$_2$dba$_3$*CHCl$_3$ (0.16 g, 0.16 mmol) were flushed under argon and dissolved in DMF (10 ml). The mixture was heated to 50° C., 1-methyl-2-(tributyltin)pyrrole (1.41 g, 3.81 mmol) added and the solution heated at 110° C. overnight. The solvent was removed under reduced pressure and the residual material subjected to flash chromatography on silica gel using EtOAc:MeOH 99:1; yield 1.15 g (77%). HRMS: M 472.1716. Calc. for $C_{21}H_{24}N_6O_7$: 472.1706. $^{13}$C NMR: (75 MHz, CDCl$_3$); δ 20.4/20.5/20.7 COCH$_3$), 35.6 (NCH$_3$), 63.0 (C-5'), 70.6/72.2 (C-2', C-3'), 79.7 (C-4'), 87.7 (C-1'), 108.3/114.3 (C-3'', C-4''), 119.7/120.2 (C-5, C-2''), 126.9 (C-5''), 144.7 (C-8), 150.3 (C-4), 152.6 (C-2), 155.0 (C-6), 169.3/169.5/170.6 (3×CO). MS (EI): M 473 (9%), 472 (40), 215 (17), 214 (100), 213 (35), 139 (21), 97 (10).

EXAMPLE 21

2',3',5'-Tris-(O-acetyl)-8-ethyladenosine (14f)

Et$_4$Sn (0.84 ml, 4.24 mmol) was added dropwise to a solution of 2',3',5'-tris-(O-acetyl)-8-bromoadenosine (12) (1.0 g, 2.12 mmol) and Pd(PPh$_3$)$_4$ (0.24 g, 0.21 mmol) in NMP (25 ml) under argon at room temperature. The mixture was heated to 130° C. and the mixture heated at this temperature for 20 h. EtOAc (100 ml) was added to the cold reaction mixture, the solution washed with water (4×50 ml) and aq. saturated NaCl (50 ml). The organic solution was dried (MgSO$_4$), the solvents distilled off and the residual material subjected to flash chromatography on silica gel using 10% MeOH in CH$_2$Cl$_2$; yield 0.51 g (57%). HRMS: M 421.1585. Calc. for $C_{18}H_{23}N_5O_7$: 421.1597. $^1$H NMR: (300 MHz, CDCl$_3$); δ 1.36 (3H, t, J 7.5 Hz, CH$_2$CH$_3$), 1.98/2.03/2.09 (3×3H, s, COCH$_3$), 2.77-2.78 (1H, m, H-3' or H-4'), 2.83-2.90 (2H, m, CH$_2$CH$_3$), 4.28-4.48 (3H, m, H-5', H-4' or H-3', 5.87-5.93 (3H, m, NH$_2$, H-2' or H-1'), 6.25-6.29 (1H, m, H-1' or H-2'), 8.22 (1H, s, H-2). $^{13}$C NMR: (75 MHz, CDCl$_3$); δ 11.7 (CH$_2$CH$_3$), 20.4/20.5/20.6 (3×COCH$_3$), 21.2 (CH$_2$CH$_3$), 63.0 (C-5'), 70.5/72.3 (C-2', C-3'), 79.9/86.6 (C-4', C-1'), 118.7 (C-5), 150.7/152.2/153.8/154.7 (C-8, C-4, C-2, C-6), 169.4/169.4/170.5 (3×CO). MS (EI): 421 (11), 362 (23), 259 (53), 192 (33), 164 (53), 163 (45), 139 (86), 97 (42), 43 (100).

EXAMPLE 22

2',3',5'-Tris-(O-acetyl)-8-(1-ethoxyvinyl)adenosine (14g)

(1-Ethoxyvinyl)tributyltin (0.60 ml, 1.78 mmol) was added dropwise to a solution of 2',3',5'-tris-(O-acetyl)-8-bromoadenosine (12) (0.70 g, 1.48 mmol), TFP (0.14 g, 0.59 mmol) and Pd$_2$dba$_3$*CHCl$_3$ (0.08 g, 0.07 mmol) DMF (14 ml) under argon at 50° C. The reaction mixture was stirred at 80° C. for 17 h. The reaction mixture was evaporated to dryness at reduced pressure and the residual material subjected to flash chromatography on silica gel using EtOAc:MeOH 99:1; yield 0.52 g (76%) of a white solid.

EXAMPLE 23

2',3',5'-Tris-(O-tert-butyldimethylsilyl)-8-methyladenosine (15a)

AlMe$_3$ (2 M in toluene, 0.44 ml, 0.87 mmol) was added dropwise to a solution of 8-bromo-2',3',5'-tris-(O-tert-butyldimethylsilyl)adenosine (13) (0.30 g, 0.44 mmol) and Pd(PPh$_3$)$_4$ (0.03 g, 0.02 mmol) in THF (5 ml) under argon. The mixture was heated at 70° C. for 4 h when TLC showed the reaction to be completed. The solution was evaporated at reduced pressure and the product isolated after flash chromatography of the residual material on silica gel using 10% MeOH in CH$_2$Cl$_2$; yield 0.27 g (>98%).

EXAMPLE 24

2', 3',5'-Tris-(O-tert-butyldimethylsilyl)-8-(2-furyl)adenosine (15b)

A solution of 8-bromo-2',3',5'-tris-O-(tert-butyldimethylsilyl)adenosine (13) (3.44 g, 5.0 mmol), Pd$_2$dba$_3$.CHCl$_3$ (65 mg, 0.063 mmol), tri(2-furyl)phosphine (115 mg, 0.5 mmol) and 2-tributylstannylfuran (1.9 ml, 6.0 mmol) in NMP (25 ml) was heated at 80° C. for 25 h. EtOAc (300 ml) was added to the cold reaction mixture, the solution shaken with water (3×50 ml), the organic solution dried (MgSO$_4$), evaporated and the residual material subjected to flash chromatography on silica gel using EtOAc:hexane, initially 1:4, then 1:2. The product was a white solid; yield 2.94 g (87%). $^1$H NMR (CDCl$_3$, 200 MHz): δ −0.39 (3H, s, CH$_3$—Si), −0.11 (3H, s, CH$_3$—Si), −0.07 (3H, s, CH$_3$—Si), −0.02 (3H, s, CH$_3$—Si), 0.13 (3H, s, CH$_3$—Si), 0.71 (9H, s, t-Bu-Si), 0.80 (9H, s, t-Bu-Si), 0.92 (9H, s, t-Bu-Si), 3.70 (1H, q), 4.0-4.1 (2H, m), 4.62 (1H, d), 5.60 (1H, dd), 6.20 (1H, d), 6.5 (3H, m), 7.08 (1H, d), 7.60 (1H, d), 8.24 (1H, s, H-2). $^{13}$C NMR (CDCl$_3$, 50 MHz): δ −5.6, −5.5, −5.2, −4.7, −4.60 and −4.58 (SiCH$_3$), 17.8, 18.0 and 18.2 (C in t-Bu), 25.6, 25.7 and 25.8 (CH$_3$ in

EXAMPLE 25

2',3',5'-Tris-(O-tert-butyldimethylsilyl)-8-phenyladenosine (16a)

Phenylboronic acid (0.09 g, 0.76 mmol) and $Cs_2CO_3$ (0.49 g, 1.53 mmol) were added to a solution of 2',3',5'-tris-(O-tert-butyldimethylsilyl)-8-bromoadenosine (13) (0.35 g, 0.51 mmol) and $Pd(PPh_3)_4$ (0.06 g, 0.05 mmol) in dioxane (5 ml). under argon at room temperature. The mixture was heated to 100° C., water added until all the $Cs_2CO_3$ had dissolved, and the solution heated under reflux overnight. EtOAc (15 ml) was added to the cold reaction mixture which was subsequently shaken with water (10 ml). The organic solution was dried ($MgSO_4$), evaporated and the title compound isolated from the residual material after flash chromatography on silica gel using EtOAc:MeOH 99:1; yield 0.31 g (89%). $^1$H NMR: (300 MHz, $CDCl_3$); δ −0.42/−0.12/0.04/0.05/0.09/ 0.11 (18H, s, 3×Si($CH_3$)$_2$), 0.69/0.87/0.88 (27H, s, 3×SiC($CH_3$)$_3$), 3.75 (1H, dd, J 4.7 Hz, J' 10.6 Hz, H-5'), 3.98-4.02 (1H, m, H-4'), 4.12 (1H, dd, J 8.2 Hz, J' 10.6 Hz, H-5'), 4.51 (1H, dd, J 2.1 Hz, J' 4.3 Hz, H-3'), 5.61 (1H, dd, J 4.3 Hz, J' 6.6 Hz, H-2'), 5.96 (1H, d, J 6.6 Hz, H-1'), 6.06 (2H, s, $NH_2$), 7.46-7.51 (3H, m, H-3", H-4", H-5"), 7.76-7.79 (2H, m, H-2", H-6"), 8.35 (1, s, H-2). $^{13}$C NMR: (75 MHz, $CDCl_3$); δ −5.5/−5.4/−5.3/−4.7/−4.4 (3×Si($CH_3$)$_2$), 17.8/18.0/18.3 (3×SiC($CH_3$)$_3$), 25.7/25.8/25.9 (3×SiC($CH_3$)$_3$), 61.7 (C-5'), 71.7/72.5 (C-2', C-3'), 85.5/88.6 (C-4', C-1'), 119.9 (C-5), 128.7/129.1/129.8/130.3 (phenyl), 150.9/151.9/153.1/155.1 (C-6, C-8, C-2, C-4).

EXAMPLE 26

2',3',5'-Tris-(O-tert-butyldimethylsilyl)-8-(3-thienyl) adenosine (16b)

3-Thiopheneboronic acid (0.14 g, 1.09 mmol) and $Cs_2CO_3$ (0.71 g, 2.18 mmol) were added to a solution of 2',3',5'-tris-(O-tert-butyldimethylsilyl)-8-bromoadenosine (13) (0.50 g, 0.73 mmol) and $Pd(PPh_3)_4$ (0.08 g, 0.07 mmol) in dioxane (7 ml) under argon. The mixture was heated to 100° C. and water (1 ml) added to dissolve all $Cs_2CO_3$. The solution was heated under reflux overnight, cooled to room temperature and EtOAc (20 ml) added. The solution was shaken with water (15 ml), dried ($MgSO_4$) and evaporated at reduced pressure. The product was isolated from the residual material after flash chromatography on silica gel EtOAc:MeOH 99:1; yield 0.43 g (86%). HRMS: M 691.3425. Calc. for $C_{32}H_{57}N_5O_4SSi_3$: 691.3439. $^1$H NMR: ($CDCl_3$, 300 MHz); δ −0.39/−0.11/ −0.01/0.002/0.12/0.13/0.70/0.84/0.91 (45H, s, 3×Si($CH_3$)$_2$ ($CH_3$)$_3$), 3.74 (1H, dd, J 4.0 Hz, J' 10.2 Hz, H-5'), 4.00-4.11 (2H, m, H-5', H-4'), 4.60 (1H, dd, J=2.7 Hz, J' 4.3 Hz, H-3'), 5.58 (1H, dd, J 4.3 Hz, J' 6.0 Hz, H-2'), 5.88 (2H, s, $NH_2$), 6.03 (1H, d, J 6.0 Hz, H-1'), 7.43 (1H, dd, J 2.9 Hz, J' 5.0 Hz, H-5"), 7.54 (1H, dd, J 1.2 Hz, J' 5.0 Hz, H-4"), 7.90 (1H, dd, J 1.2 Hz, J' 2.9 Hz, H-2"). $^{13}$C NMR: ($CDCl_3$, 75 MHz); δ −5.5/−5.4/ −5.2/−4.7/−4.6/−4.5 (6×$SiCH_3$), 17.9/18.0/18.3 (3× $SiCCH_3$), 25.7/25.8/25.8 (9×$SiCCH_3$), 62.5 (C-5'), 72.0/72.3 (C-2', C-3'), 85.2/88.7 (C-1', C-4'), 119.8 (C-5), 126.6/127.9/ 128.4/130.0 (C-2", C-3", C-4", C-5"), 148.6/150.8/152.2/ 155.2 (C-8, C-4, C-2, C-6). MS (EI): 691 (M, 0.6%), 636 (26), 624 (100), 374 (25), 147 (15), 89 (21), 73 (91).

EXAMPLE 27

2',3',5'-Tris-O-(tert-butyldimethylsilyl)-8-(3-pyridinyl)adenosine (16c)

Pyridine-3-boronic acid (0.59 g, 0.48 mmol) and $Cs_2CO_3$ (3.11 g, 9.57 mmol) were added to a solution of 2',3',5'-tris-O-(tert-butyldimethylsilyl)-8-bromoadenosine (13) (2.20 g, 3.19 mmol) and $Pd(PPh_3)_4$ (0.37 g, 0.32 mmol) in dioxane (50 ml) under argon. Water (10 ml) was added to dissolve all $Cs_2CO_3$. The solution was heated under reflux overnight. EtOAc (200 ml) was added to the cold reaction mixture, the resultant solution shaken with water (100 ml), the organic solution dried ($MgSO_4$), evaporated and the residual material subjected to flash chromatography on silica gel using EtOAc: MeOH 99:1; yield 1.76 g (80%). HRESI: M+H 687.3900. Calc. for $C_{33}H_{58}N_6O_4Si_3$+H, 687.3900. $^1$H NMR: (300 MHz, $CDCl_3$); δ −0.41/−0.12/0.01/0.02/0.09/0.11 (18H, s, 3×Si($CH_3$)$_2$), 0.67/0.85/0.86 (27H, s, 3×SiC($CH_3$)$_3$), 3.71-4.12 (3H, m, H-5', H-3' or H-4'), 4.53-4.55 (1H, m, H-4' or H-3'), 5.61-5.65 (1H, m, H-2'), 5.81 (1H, d, J 6.3 Hz, H-1'), 6.02 (2H, s, $NH_2$), 7.38-7.42 (1H, m, H-5"), 8.09-8.12 (1H, m, H-4"), 8.30 (1H, s, H-2), 8.73-8.75 (1H, m, H-6"), 9.04-9.05 (1H, m, H-2"). $^{13}$C NMR: (75 MHz, $CDCl_3$); δ −5.5/−5.4/ −5.3/−4.7/−4.6/−4.5 (3×Si($CH_3$)$_2$), 17.2/18.0/18.3 (3×SiC), 25.6/25.8/25.8 (3×SiC($CH_3$)$_3$), 62.5 (C-5'), 71.7/72.4 (C-2', C-3'), 85.5/88.9 (C-4', C-1'), 120.1/123.1/125.7/136.9/149.9/ 150.4/151.0/151.1/152.6/155.6 (C-5, C-5", C-3", C-4", C-6, C-8, C-6", C-2", C-2, C-4).

EXAMPLE 28

2',3',5'-Tris-(O-tert-butyldimethylsilyl)-8-(4-pyridinyl)adenosine (16d)

A solution of pyridine-4-boronic acid (0.27 g, 2.18 mmol) and $Cs_2CO_3$ (1.42 g, 4.35 mmol) in water (11 ml) was added to a solution of 2',3',5'-tris-(O-tert-butyldimethylsilyl)-8-bromoadenosine (13) (1.0 g, 1.45 mmol) and $Pd(PPh_3)_4$ (0.17 g, 0.15 mmol) in dioxane (25 ml) and the reaction mixture heated at 100° C. overnight. EtOAc (80 ml) was added to the cold reaction mixture and the resultant mixture shaken with water (50 ml). The dried ($MgSO_4$) solution evaporated and the residual material subjected to flash chromatography on silica gel using EtOAc:MeOH 99:1; yield 0.58 g (58%). HRESI: M+H 687.3883. Calc. for $C_{33}H_{58}N_6O_4Si_3$+H, 687.3900. $^1$H NMR: (300 MHz, $CDCl_3$); δ −0.43/−0.12/0.02/ 0.04/0.09/0.11 (18H, s, 3×Si($CH_3$)$_2$), 0.67/0.86/0.87 (27H, s, 3×SiC($CH_3$)$_3$), 3.72-3.76 (1H, m, H-5'), 4.02-4.13 (2H, m, H-4' or H-3' and H-5'), 4.49-4.51 (1H, m, H-3' or. H-4'), 5.61-5.65 (1H, m, H-2'), 5.92 (1H, d, J 6.6 Hz, H-1'), 6.08 (2H, s, $NH_2$), 7.71-7.73 (2H, m, H-2" and H-6"), 8.30 (1H, s, H-2), 8.75-8.77 (2H, m, H-3" and H-5"). $^{13}$C NMR: (75 MHz, $CDCl_3$); δ −5.5/−5.4/−5.3/−4.7/−4.5 (3×Si($CH_3$)$_2$), 17.8/ 17.9/18.3 (3×SiC), 25.6/25.7/25.8 (3×SiC($CH_3$)$_3$), 62.5 (C-5'), 71.6/72.4 (C-2', C-3'), 85.7/88.6 (C-4', C-1'), 120.1/ 123.7/136.9/150.3/151.1/152.9/155.7 (C-5, C-5", C-3", C-6, C-8, C-6", C-2", C-2, C-4, C-1").

EXAMPLE 29

8-(2-Furyl)adenosine (17a) (ester hydrolysis)

A solution of 2',3',5'-tris-(O-acetyl)-8-(2-furyl)adenosine (14b) (1.39 g, 3.03 mmol) and $K_2CO_3$ (0.14 g, 1.01 mmol) in MeOH (50 ml) was stirred at room temperature overnight. Silica gel was added to the solution, the suspension stirred and evaporated to dryness and the residual material applied on top of a column with silica gel for flash chromatography. The column was developed with 15% MeOH in $CH_2Cl_2$; yield 0.68 g (67%).

EXAMPLE 30

8-(2-Furyl)adenosine (17a) (desilylation)

A solution of 2',3',5'-tris-(O-tert-butyldimethylsilyl)-8-(2-furyl)adenosine (15b) (2.78 g, 4.1 mmol) and TBAF×3H$_2$O (5.30 g, 16.8 mmol) in THF (70 ml) was stirred at room temperature for 2 h. The solvent was distilled off and the product purified by flash chromatography using MeOH:CH$_2$Cl$_2$ 1:9 and the product triturated with a small amount of MeOH; yield 1.24 g (90%) of a light tan solid. $^1$H NMR (DMSO-d$_6$, 200 MHz): δ 3.5 3.6 (1H, m), 3.70 (1H, dt), 3.99 (1H, m), 4.20 (1H, m), 5.0-5.2 (2H, m), 5.45 (1H, d), 6.76 (1H, q), 7.13 (1H, dd), 7.56 (2H, br s, NH$_2$), 8.00 (1H, d), 8.14 (1H, s, H-2). $^{13}$C NMR (DMSO-d$_6$, 50 MHz): δ 62.2, 71.0, 71.6, 86.7, 89.3, 112.1, 113.9, 119.4, 141.5, 143.2, 145.5, 149.6, 152.3, 156.2.

EXAMPLE 31

8-(2-Thienyl)adenosine (17b)

A solution of 2',3',5'-tris-(O-acetyl)-8-(2-thienyl)adenosine (14d) and K$_2$CO$_3$ in MeOH was stirred at room temperature overnight, evaporated to dryness at reduced pressure and the title compound isolated from the residual material after flash chromatography on silica gel using 10% MeOH in CH$_2$Cl$_2$; yield >60%. HRMS: M 349.0832. Calc. for C$_{14}$H$_{15}$N$_5$O$_4$S: 349.0845. $^1$H NMR: (300 MHz, DMSO-d$_6$); δ 3.51-3.73 (2H, m, H-5'), 3.98-3.99 (1H, m, H-4'), 4.19-4.20 (1H, m, H-3'), 5.16-5.21 (2H, m, H-2',3'-OH), 5.53 (1H, d, J 6.3 Hz, 2'-OH), 5.80 (1H, dd, J 3.4 Hz, J' 8.9 Hz, 5'-OH), 6.00 (1H, d, J 7.0 Hz, H-1'), 7.28 (1H, dd, J 3.7 Hz, 5.0 Hz, H-4"), 7.51 (2H, s, NH$_2$), 7.65 (1H, dd, J 0.9 Hz, J' 3.7 Hz, H-3"), 7.86 (1H, dd, J 0.9 Hz, J' 5.0 Hz, H-5"), 8.14 (1H, s, H-2). $^{13}$C NMR: (75 MHz, DMSO-d$_6$); δ 62.2 (C-5'), 71.1/71.4 (C-2', C-3'), 86.77 (C-4'), 89.2 (C-1'), 119.2 (C-5), 128.2/129.9/130.0 (C-3", C-4", C-5"), 130.7 (C-2"), 145.0 (C-8), 150.0 (C-4), 152.2 (C-2), 156.0 (C-6). MS (EI): 350 (M, 0.3%), 349 (4), 260 (6), 219 (6), 218 (20), 217 (100), 190 (14), 110 (10).

EXAMPLE 32

8-(3-Furyl)adenosine (17c)

A solution of 2',3',5'-tris-(O-acetyl)-8-(3-furyl)adenosine (14c) (0.95 g, 2.07 mmol) and K$_2$CO$_3$ (0.10 g, 0.69 mmol) in MeOH (35 ml) was stirred at room temperature overnight. Silica gel was added, the suspension stirred and the solvent evaporated off at reduced pressure. The residual material was subjected to flash chromatography on silica gel using 15% MeOH in CH$_2$Cl$_2$; yield 0.50 g (72%). HRESI: M+H 350.0902. Calc. C$_{14}$H$_{15}$N$_5$O$_4$S+H, 350.0917. M+Na: 372.0747. Calc. for C$_{14}$H$_{15}$N$_5$O$_4$S+Na: 372.0736. $^1$H NMR: (300 MHz, DMSO-d$_6$); δ 3.53-3.60 (2H, m, C-5'), 3.99-4.00 (1H, m, H-4'), 4.19-4.22 (1H, m, H-3'), 5.06-5.13 (1H, m, H-2'), 5.24 (1H, d, J 4.6 Hz, 3'-OH), 5.52 (1H, d, J 6.6 Hz, 2'-OH), 5.87-5.94 (2H, m, 5'-OH, H-1'), 6.94 (1H, d, J 1.2 Hz, H-4"), 7.48 (2H, s, NH$_2$), 7.92/8.14 (2H, s, H-1", H-5"), 8.24 (1H, s, H-2). $^{13}$C NMR: (75 MHz, DMSO-d$_6$); δ 62.2 (H-5'), 71.1/71.7/86.9/89.0 (C-2', C-3', C-4', C-1'), 111.1/115.6 (C-4", C-3"), 119.2 (C-5), 143.6/144.2/144.5/149.7/151.9/156.0 (C-2", C-5", C-6, C-8, C-2, C-4).

EXAMPLE 33

8-(3-Thienyl)adenosine (17d)

A solution of 2',3',5'-tris-(O-tert-butyldimethylsilyl)-8-(3-thienyl)adenosine (16b) (1.21 g, 1.75 mmol) and TBAF (1.83 g, 6.99 mmol) in THF (67 ml) was stirred at room temperature overnight. The solvent was distilled off and the residual material subjected to flash chromatography on silica gel using 10% MeOH in CH$_2$Cl$_2$; yield 0.51 g (84%). HRESI: M+H 350.0902. Calc. for C$_{14}$H$_{15}$N$_5$O$_4$S+H, 350.0917. M+Na 372.0747. Calc. for C$_{14}$H$_{15}$N$_5$O$_4$S+Na: 372.0736. $^1$H NMR: (300 MHz, DMSO); δ 3.51-3.73 (2H, m, H-5'), 3.96-3.97 (1H, m, H-4'), 4.17-4.21 (1H, m, H-3'), 5.11-5.18 (1H, m, H-2'), 5.20 (1H, d, J 4.4 Hz, 3'-OH), 5.54 (1H, d, J 6.4 Hz, 2'-OH), 5.85-5.90 (2H, m, 5'-OH or H-1'), 7.47 (2H, s, NH$_2$), 7.52 (1H, dd, J 1.2 Hz, J' 5.0 Hz, H-4"), 7.78 (1H, dd, J 2.9 Hz, J' 5.0 Hz, H-5"), 8.05 (1H, dd, J 1.2 Hz, J' 2.9 Hz, H-2"), 8.14 (1H, s, H-2). $^{13}$C NMR: (75 MHz, DMSO-d$_6$); 62.3 (C-5'), 71.1/71.5 (C-2', C-3'), 86.8/87.0 (C-4', C-1'), 119.0 (C-5), 127.5/128.3/128.4/130.0 (C-2", C-3", C-4", C-5"), 146.7/149.6/152.0/156.1 (C-8, C-4, C-2, C-6).

EXAMPLE 34

8-Phenyladenosine (17e)

A solution of 2',3',5'-tris-(O-acetyl)1-8-phenyladenosine (14a) (0.73 g, 1.56 mmol) and K$_2$CO$_3$ (0.07 g, 0.52 mmol) in MeOH (23 ml) was stirred at room temperature for 24 h. Silica gel (ca. 2 g), was added. The suspension stirred and evaporated to dryness at reduced pressure. The residual material was added on top of a silica gel flash chromatography column and the column developed with 10% MeOH in CH$_2$Cl$_2$; yield 0.48 g (91%). HRMS: M 343.1287. Calc. for C$_{16}$H$_{17}$N$_5$O$_4$: 343.1281. MS (EI): 343 (M, 1%), 254 (9), 240 (7), 212 (25), 211 (100), 184 (12), 104 (12).

EXAMPLE 35

8-(3-Pyridinyl)adenosine (17f)

A solution of 2',3',5'-tris-O-(tert-butyldimethylsilyl)-8-(3-pyridinyl)adenosine (16c) (0.56 g, 0.82 mmol) and TBAF (0.85 g, 3.26 mmol) in THF (31 ml) under argon was stirred at room temperature overnight. The solvent was distilled off and the residual material dissolved in MeOH (10 ml). The solution was left at 0° C. overnight and the title compound isolated by filtration. $^{13}$C NMR: (75 MHz, DMSO); δ 62.27 (C-5'), 71.13/71.62 (C-2', C-3'), 86.95/89.27 (C-4, C-1), 119.33/123.69/125.71/137.20/148.20/149.80/149.85/150.88/152.33/156.34 (C-5, C-5", C-3", C-4", C-6, C-8, C-6", C-2", C-2, C-4). MS (EI): 344 (M, 2%), 255 (5), 241 (5), 213 (22), 212 (100), 211 (5) 185 (12), 104 (12).

EXAMPLE 36

8-(4-Pyridinyl)adenosine (17g)

TBAF (7.39 ml, 1 M, 7.39 mmol) was added to a solution of 2',3',5'-tris-(O-tert-butyldimethylsilyl)-8-(4-pyridinyl)adenosine (16d) (1.27 g, 1.85 mmol) in THF (28 ml) and the solution stirred at room temperature overnight. The solution was evaporated to dryness at reduced pressure and the residual material subjected to flash chromatography on silica gel using 15% MeOH in $CH_2Cl_2$; yield 0.46 g (72%). HRESI: M+H 345.1313. Calc. for $C_{15}H_{16}N_6O_4$+H, 345.1305. $^1H$ NMR: (300 MHz, DMSO); δ 3.51-3.60 (2H, m, H-5'), 3.97-3.98 (1H, m, H-4' or. H-3'), 4.15-4.19 (1H, m, H-3' or H-4'), 5.13-5.19 (1H, m, H-2') 5.22 (1H, d, J 4.4 Hz, 3'-OH), 5.54 (1H, d, J 6.5 Hz, 2'-OH), 5.75 (1H, d, J 7.3 Hz, H-1'), 5.74-5.81 (1H, m, 5'-OH), 7.66 (2H, s, $NH_2$), 7.74-7.76 (2H, m, H-2" and H-6"), 8.19 (1H, s, H-2), 8.80-8.82 (2H, m, H-3" and H-5"). $^{13}C$ NMR: (75 MHz, DMSO); δ 62.2 (C-5'), 71.0/71.4 (C-2', C-3'), 87.0/89.1 (C-4', C-1'), 119.4 (C-5), 123.8 (C-2", C-6"), 150.3 (C-3' and C-5'), 136.9/148.4/150.0/152.7/156.5 (C-6, C-8, C-2, C-4, C-1").

EXAMPLE 37

8-(1-Methyl-2-pyrrolyl)adenosine (17h)

A solution of 2',3',5'-tris-(O-acetyl)-8-(1-methyl-2-pyrrolyl)adenosine (14e) (1.04 g, 2.20 mmol) and $K_2CO_3$ (0.10 g, 0.73 mmol) in MeOH (37 ml) was stirred at room temperature overnight, the solution evaporated at reduced pressure and the residual material subjected to flash chromatography on silica gel using 15% MeOH in $CH_2Cl_2$; yield 0.64 g (84%). HRMS: M 346.1371. Calc. for $C_{15}H_{18}N_6O_4$: 346.1390. $^{13}C$ NMR: (75 MHz, DMSO); δ 35.1 ($NCH_3$), 62.4 (C-5'), 71.2/71.4 (C-2', C-3'), 86.6/89.0 (C-4', C-1'), 107.71/113.9 (C-3", C-4"), 119.2/120.4 (C-5, C-2"), 126.8 (C-5"), 144.1 (C-8), 149.2 (C-4), 151.7 (C-2), 155.9 (C-6). MS (EI): M+346 (5%), 215 (11), 214 (100), 213 (60), 129 (12), 128 (8), 115 (35), 97 (9), 69 (12).

EXAMPLE 38

8-Methyladenosine (17i)

A solution of 8-bromo-2',3',5'-tris-(O-tert-butyldimethylsilyl)adenosine (15a) (1.41 g, 2.26 mmol) and TBAF (2.37 g, 9.05 mmol) in THF (30 ml) was stirred at room temperature overnight. The solvent was distilled off and the residual material subjected to flash chromatography on silica gel using 15% MeOH in $CH_2Cl_2$; yield 0.59 g (93%).

EXAMPLE 39

8-Ethyladenosine (17j)

A solution of 2',3',5'-tris-(O-acetyl)-8-ethyladenosine (14f) (0.63 g, 1.5 mmol) and $K_2CO_3$ (0.07 g, 0.50 mmol) in MeOH (19 ml) was stirred at room temperature for 18 h. Silica gel was added, the suspension stirred and the solvent evaporated off at reduced pressure. The residual material was applied on top of a silica gel flash chromatography column and the column developed 15% MeOH in $CH_2Cl_2$; yield 0.23 g, 52%.

EXAMPLE 40

8-(1-Ethoxyvinyl)adenosine (17k)

A solution of 2',3',5'-tris-(O-acetyl)-8-(1-ethoxyvinyl)adenosine (14g) (0.53 g, 1.15 mmol) and $K_2CO_3$ (0.05 g, 0.38 mmol) in MeOH (17 ml) was stirred at room temperature for 24 h when TLC showed full conversion. Silica gel was added to the solution, the suspension stirred and evaporated to dryness at reduced pressure. The residual material was applied on top of a silica gel flash chromatography column which was developed with 10% MeOH in $CH_2Cl_2$; yield 0.37 g (>95%). HRMS: M 337.1395. Calc. for $C_{14}H_{19}N_5O_5$: 337.1386. $^1H$ NMR: (300 MHz, DMSO-$d_6$); δ 1.31 (3H, t, J 6.9 Hz, $OCH_2CH_3$), 3.53-3.71 (2H, m, H-5'), 3.94 (2H, J 13.9 Hz, J' 6.9 Hz, $OCH_2CH_3$), 3.90-3.98 (1H, m, H-4'), 4.19-4.22 (1H, m, H-3'), 4.76-4.79 (2H, m, $CCH_2$), 5.0-5.02 (1H, m), 5.1 (1H, d, 4.15 Hz), 5.29 (1H, d, J 6.3 Hz), 5.71-5.75 (1H, m, H-2'), 5.97 (1H, d, J 6.8 Hz, H-1'), 7.51 (2H, s, $NH_2$), 8.12 (1H, s, H-2). $^{13}C$ NMR: (75 MHz, DM2 (C-1', C-4', $CCH_2$), 118.5 (C-5), 146.7/149.3/150.6/152.4/156.5 (C-6, C-8, C-2, C-4, $CCH_2$). MS (EI): 337 (M, 8%), 308 (18), 278 (17), 234 (21), 205 (96), 190 (100), 178 (47), 161 (80), 135 (16).

EXAMPLE 41

8-Acetyladenosine (17l)

1 M HCl (10 ml) was added to a solution of 8-ethoxyvinyladenosine (17k) (1.48 g, 4.37 mmol) in THF (40 ml) and the solution stirred at room temperature for 20 h. Aqueous $K_2CO_3$ was added to neutral pH and the mixture applied directly onto a flash chromatography silica gel column which was developed with 15% MeOH in $CH_2Cl_2$; yield 1.17 g (87%). $^1H$ NMR: (300 MHz, DMSO-$d_6$); δ 2.72 (3H, s, $COCH_3$), 3.52-3.71 (2H, m, H-5'), 3.94-3.96 (1H, m, H-4' el. H-3'), 4.10-4.23 (1H, m, H-3' or H-4'), 4.94 (1H, m, H-2'), 5.11 (1H, d, J 4.4 Hz, 3'-OH), 5.24 (1H, d, J 6.1 Hz, 2'-OH), 5.56-5.59 (1H, m, 5'-OH), 6.76 (1H, d, J 6.5 Hz, H-1'), 7.87 (2H, s, $NH_2$), 8.21 (1H, s, H-2). $^{13}C$ NMR: (75 MHz, DMSO-$d_6$); δ 27.9 ($CH_3$), 62.3 (C-5'), 70.9/72.0 (C-2', C-3'), 86.3/89.3 (C-4', C-1'), 118.7 (C-5), 143.7/150.5/154.7/157.7 (C-6, C-8, C-2, C-4), 191.7 (CO).

EXAMPLE 42

8-(1-Hydroxyethyl)adenosine (17m)

$NaBH_4$ (0.19 g, 5.05 mmol) was added to a solution of 8-acetyladenosine (17l) (0.78 g, 2.52 mmol) in THF (35 ml) and MeOH (4 ml) under argon and the mixture stirred at room temperature for 18 h. The mixture was treated dropwise with 1 M HCl until neutral pH and the mixture applied on top of a flash chromatography column which was developed by 30% MeOH in $CH_2Cl_2$; yield 0.46 g (59%). The product was a mixture of the two alcohol epimers, ratio 1:1.

EXAMPLE 43

($R_p$)-Adenosine-3',5'-cyclic phosphorothioic acid O-methyl ester (19)

A solution of adenosine (9) (0.106 g, 0.4 mmol) in dry DMF (7 ml) was added to (0.45 ml, 0.2 mmol) 0.5 M tetrazole in acetonitrile and the solution heated under an argon atmosphere to 60° C. Bis(N,N-diisopropylamino)methoxyphosphine (0.105 g, 0.4 mmol) was then added slowly and the reaction mixture left at this temperature for 15 min. The reaction mixture was cooled to room temperature and sulfur (0.013 g, 0.4 mmol) added. The mixture was stirred at room temperature for 8 h. The reaction mixture was evaporated to dryness at reduced pressure. The residual solid was a mixture of ($R_p$)-adenosine-3',5'-cyclic phosphorothioic acid and its ($S_p$)-isomer in the ratio 2:3. The isomers were separated by preparative HPLC on reverse phase C18-functional silica gel. The isolated yield of the title compound was 0.018 g (12%). $^{31}P$ NMR (DMSO-$d_6$): 66.4 ppm. $^1H$ NMR: 3.83 (d, J 10 Hz, 3H, HMe) 4.2-5.0 (6H, m, H-2', H-3', H 4', H-5', OH), 6.14 (1H, s, H-1'), 8.34 (1H, s, H-2), 8.88 (1H, s, H-8).

EXAMPLE 44

($R_p$)-8-(2-Thienyl)adenosine-3',5'-cyclic phosphorothioic acid S-methyl pivalate (26)

($R_p$)-8-(2-Thienyl)adenosine-3',5'-cyclic phosphorothioic acid ammonium salt (7b) (0.2 mmol) was dissolved in methanol (5 ml) and triethylamine (0.3 mmol) added. Evaporation of the mixture under vacuum left the ($R_p$)-8-(2-thienyl)adenosine-3',5'-cyclic phosphorothioic acid triethylammonium salt. Part of this product (74 mg, 0.14 mmol) and NaI (20 mg, 0.11 mmol) were dissolved in DMF (3 ml) under argon and chloromethyl pivalate (20 mg, 0.11 mmol) added The mixture was stirred at room temperature for 48 h. The solvent was distilled off at reduced pressure and the residual material subjected to flash chromatography on silica gel using $CH_2Cl_2$:MeOH, initially 3:97 and then 5:95; yield 30 mg (40%) of a white solid. $^1$H NMR ($CD_3OD$, 200 MHz): δ 1.22 (9H, s), 4.5-4.8 (3H, m), 5.26 (1H, d), 5.45 (1H, d), 5.49 (1H, s), 5.57 (1H, d), 5.7-5.8 (1H, m), 6.11 (1H, s), 7.26 (1H, dd), 7.65 (1H, dd), 7.75 (1H, dd), 8.22 (1H, s). $^{31}$P NMR ($CDCl_3$, 81 MHz): δ 27.3.

EXAMPLE 45

($R_p$)- and ($S_p$)-8-Phenyladenosine-3',5'-cyclic phosphorothioic acid S-methyl pivalate (27)

A crude 1:1 diastereomeric mixture of ($R_p$)- and ($S_p$)-8-phenyladenosine-3',5'-cyclic phosphorothioic acid (7e) as its sodium salt (150 mg, 0.34 mmol) was dissolved in methanol (5 ml), sodium iodide (51 mg, 0.34 mmol mg) added followed by chloromethyl pivalate (61 mg, 0.41 mmol). The reaction mixture was kept under argon and heated under reflux for 6 h. The mixture was evaporated to dryness at reduced pressure and the solid residue extracted several times with dichloromethane. The extracts were collected and evaporated to yield a brownish coloured solid (142 mg). From phosphorus NMR it was evident that the crude product consisted of only the title compounds in an approximately 1:1 ratio. The diastereoisomers were then separated by silica gel flash chromatography using $CH_2Cl_2$:MeOH 95:1.

($R_p$)-8-Phenyladenosine-3',5'-cyclic phosphorothioic acid S-methyl pivalate (27)

The solid product was isolated in 16% yield (28 mg). $^{31}$P NMR ($CD_3OD$): 27.5 ppm. $^1$H NMR ($CD_3OD$): δ 1.30 (9H, s), 3.01 (2H, q), 3.36 (2H, q), 5.28 (1H, d) 5.54 (1H, d), 5.60 (1H, d), 6.05 (1H, s), 7.2-7.5 (5H, m), 8.40 (1H, s).

($S_p$)-8-Phenyladenosine-3',5'-cyclic phosphorothioic acid S-methyl pivalate (27)

The solid product was isolated in 20% yield (36 mg). $^{31}$P NMR ($CD_3OD$): 24.0 ppm. $^1$H NMR ($CD_3OD$): δ 1.32 (9H, s,), 2.89 (2H, q), 3.46 (2H, q), 5.13 (1H, d) 5.30 (1H, d), 5.40 (1H, d), 6.21 (1H, s), 7.2-7.5 (5H, m), 8.38 (1H, s).

EXAMPLE 46

PKA Iα Enzymatic Activity

Rp-8-carbylated cAMPS were tested for their potency in a coupled Cook calorimetric assay for PKA type Iα enzymatic activity relative to the known Rp-8-Br-cAMPS. The results are set out in Table 1 below:

TABLE 1

| Compound | Potency |
|---|---|
| Rp 8-(2-furyl)-cAMPS | 4.24 |
| Rp 8-(2-thienyl)-cAMPS | 3.01 |
| Rp 8-(3-furyl)-cAMPS | 2.23 |
| Rp 8-(3-thienyl)-cAMPS | 1.83 |
| Rp 8-(phenyl)-cAMPS | 1.28 |
| Rp 8-bromo-cAMPS | 1.00 |

EXAMPLE 47

8-Bromoadenosine-3',5'-cyclic phosphoric acid (1)

Bromine (15.4 ml, 0.30 mol) was added with stirring to a solution of cAMP (98.8 g, 0.30 mol) and sodium acetate trihydrate (81.6 g, 0.60 mol) in water (1.5 l) over 1 h at room temperature. After 24 h, sodium sulfite was added slowly until disappearance of the dark red colour. The precipitate was collected by filtration, the solid washed with water, isopropyl alcohol and diethyl ether before being dried at reduced pressure. The product was dispersed in water (500 ml) and dissolved by slow addition of sodium bicarbonate (1 equiv.). When all the material had dissolved, small portions of sodium sulfite were added to remove the dark red colour of the solution. Precipitation of the product was effected by dropwise addition of 1.0 M hydrobromic acid under vigorous stirring. The precipitate was collected, washed with water, isopropyl alcohol, diethyl ether and the bright yellow powder dried under high vacuum; yield 92.0 g (76%). $^1$HNMR was in accordance with the literature.

EXAMPLE 48

(Sp)-8-Bromoadenosine-2'O-(tert-butyldimethylsilyl)-3',5'-cyclic N-phenylphosphoramidate (4)

Dry DMF (0.289 g, 3.96 mmol) in dry THF (20 ml) was placed under an atmosphere of argon gas and cooled to 0° C. before oxalyl chloride in dichloromethane (2 ml, 2 M, 4 mmol) was added slowly. The cooling bath was removed and the suspension left stirring at room temperature for 30 min, the reaction mixture cooled to −7° C. and added to a solution of tributylammonium 8-bromoadenosine-2O-TBDMS-3,5-cyclic monophosphate (1) (2.55 g, 3.60 mmol) in dry dichloromethane (8 ml). The mixture was stirred at this temperature for 1 h, allowed to reach room temperature and dry ($CaH_2$) aniline (3.35 g, 36 mmol) added. After 3 h, the turbid reaction mixture was diluted to 100 ml with dichloromethane and washed with cold, saturated sodium hydrogen carbonate (3×25 ml). The organic phase was then dried over $MgSO_4$, the solvent removed at reduced pressure and the residual material added slowly with vigorous stirring to cyclohexane (100 ml). The precipitate was dried and subjected to flash chromatography on silica gel using 7% methanol in dichloromethane as eluent; yield 1.46 g (68%). $^1$HNMR was in accordance with the literature.

EXAMPLE 49

(Sp)-8-(5-Methyl-2-furyl)adenosine-2'O-(tert-butyldimethylsilyl)-3',5'-cyclic N-phenylphosphoramidate (5e)

Dry degassed DMF (6 ml), palladium acetate (0.0169 g, 0.07 mmol) and triphenylphosphine (0.041 g, 0.158 mmol)

were heated together at 50° C. under argon until a deep red and homogenous solution resulted (ca. 15 min). 2-Tributylstannyl-5-methylfurane (0.904 mmol) and (Sp)-8-bromoadenosine-2'O-(tert-butyldimethylsilyl) 3',5'-cyclic N-phenylphosphoramidate (0.450 g, 0.753 mmol) were added, and the mixture heated at 80° C. for 4 h. The solvent was distilled off, the residue dissolved in dichloromethane (3 ml) and the solution added with vigorous stirring to hexane (50 ml). Flash chromatography of the precipitate on silica gel with 7% methanol in dichloromethane furnished the product, yield: 0.405 g (90%). HRMS (electrospray): (M+H) 599.2181. Calc. for $C_{21}H_{31}N_6O_6PSi+H$, 599.2197. $^{31}P$ NMR ($CDCl_3$, 81 MHz): $^1H$ NMR (DMSO-$d_6$, 300 MHz): δ −0.130 (3H, s, $CH_3Si$), −0.09 (3H, s, $CH_3Si$), 0.730 (9H, s, $(CH_3)_3C$), 2.40 (3H, s, $CH_3$-Fur), 4.3-4.7 (3H, m, H4' H5'), 5.21 (1H, d, J 5.2 Hz, H2'), 5.6-5.7 (1H, m, H3'), 6.30 (1H, s, H1'), 6.41 (1H, d, $J_{PH}$ 3.3 Hz, NH), 6.9-7.2 (6H, m, H—Ar), 8.23 (1H, s, H2), 7.52 (2H, br.s, $NH_2$), 8.54 (1H, d, J 9.4 Hz, H-Fur). $^{13}C$ NMR ($CDCl_3$, 75 MHz): δ −5.5, −5.0, 13.4, 17.7, 25.4, 68.3, 70.1, 72.2, 76.3, 93.5, 108.6, 115.0, 118.4, 118.5, 119.0, 128.8, 139.5, 140.5, 141.5, 149.8, 153.1, 154.8, 155.9

EXAMPLE 50

(Sp)-8-(5-Methoxy-2-furyl)adenosine-2'O-(tert-butyldimethylsilyl)-3',5'-cyclic N-phenylphosphoramidate (5f)

A solution of palladium acetate (16.9 mg, 0.075 mmol) and triphenylphosphine (41.5 mg, 0.158 mmol) in dry degassed DMF (6 ml) was heated at 50° C. under argon for 15 min (deep red colour) before 2-(tributylstannyl)-5-methoxyfurane (0.387 g, 1.00 mmol) and (Sp)-8-bromoadenosine-2'O-(tert-butyldimethylsilyl)-3',5'-cyclic N-phenylphosphoramidate (4) (0.450 g, 0.753 mmol) were added. The mixture was heated at 85° C. for 4 h. The solvent was removed under vacuum, the residual material dissolved in dichloromethane (3 ml), the solution added slowly to vigorously stirred hexane (50 ml) and the precipitated material subjected to flash chromatography on silica using 7% methanol in dichloromethane; yield 310 mg (67%). HRMS (electrospray): (M+H) 615.2118. Calc. for $C_{27}H_{31}N_6O_7PSi+H$, 615.2146. $^{31}P$ NMR ($CDCl_3$, 81 MHz): δ 3.05. $^1H$ NMR ($CDCl_3$, 200 MHz): δ −0.02 (1H, s, $CH_3Si$), 0.00 (3H, s, $CH_3Si$), 0.82 (9H, s, $(CH_3)_3C$), 3.96 (3H, s, $CH_3O$), 4.5-4.7 (3H, m, H4' H5'), 5.30 (1H, d, J 5.1 Hz, H2'), 5.40 (1H, d, J 3.6 Hz, NH), 5.8-5.9 (1H, m, H3'), 6.32 (1H, s, H1'), 6.65 (2H, br.s, $NH_2$), 7.0-7.3 (6H, m, H—Ar), 7.68 (1H, d, J 9.4 Hz, H-Fur), 8.39 (1H, s, H2). $^{13}C$ NMR ($CDCl_3$, 75 MHz): δ −5.4, −4.8, 18.0, 25.5, 58.1, 69.1, 70.6, 72.9, 82.6, 94.2, 116.7, 119.4, 119.6, 122.8, 129.1, 133.2, 138.7, 141.8, 150.2, 152.9, 155.3, 163.3, 174.0.

EXAMPLE 51

(Sp)-8-(5-(tert-Butyldimethylsilyloxymethyl)-2-furyl)adenosine-2'O-(tert-butyldimethylsilyl)-3',5'-cyclic N-phenylphosphoramidate (5g)

A solution of palladium acetate (16.9 mg, 0.075 mmol) and triphenylphosphine (41.5 mg, 0.158 mmol) in dry degassed DMF (6 ml) was heated at 50° C. under argon for 15 min (deep red colour) before 2-tributylstannyl-5-(tert-butyldimethylsilyloxymethyl)furane (0.478 g, 0.904 mmol) and (Sp)-8-bromoadenosine-2'O-(tert-butydimethylsilyl)-3',5'-cyclic N-phenylphosphoramidate (4) (0.450 g, 0.753 mmol) were added. The mixture was heated at 85° C. for 4 h. The solvent was removed under vacuum, the residual material dissolved in dichloromethane (3 ml), the solution added slowly to vigorously stirred hexane (50 ml) and the precipitated material subjected to flash chromatography on silica gel using 7% methanol in dichloromethane; yield 461 mg (84%). HRMS (electrospray): (M+H) 729.3001. Calc. for $C_{33}H_{49}N_6O_7PSi_2+H$, 729.3011. $^{31}P$ NMR ($CDCl_3$, 81 MHz): δ 3.05. $^1H$ NMR ($CDCl_3$, 200 MHz): δ −0.01 (3H, s, $CH_3SiOCH$), 0.00 (3H, s, $CH_3SiOCH$), 0.17 (6H, s, $CH_3SiOCH_2$), 0.81 (9H, s, $(CH_3)_3CSiOCH$), 0.98 (9H, s, $(CH_3)_3CSiOCH_2$), 4.5-4.7 (3H, m, H4' H5'), 4.78 (2H, s, $OCH_2Fur$), 5.31 (1H, d, J 5.2 Hz, H2'), 5.8-5.9 (1H, m, H3'), 6.40 (1H, s, H1'), 6.47 (1H, d, J 3.4 Hz, NH), 6.61 (2H, br.s, $NH_2$), 7.1-7.3 (6H, m, H—Ar), 7.63 (1H, d, J 9.4 Hz, H-Fu), 8.42 (1H, s, H2). $^{13}C$ NMR ($CDCl_3$, 75 MHz): δ −5.3, −4.7, 18.0, 18.3, 25.6, 25.8, 58.2, 69.1, 70.7, 72.8, 94.2, 109.1, 115.1, 119.5, 119.7, 122.8, 129.2, 138.7, 141.8, 142.5, 150.2, 153.3, 155.6, 157.6.

EXAMPLE 52

($S_p$)-8-(2-Benzofuryl)adenosine-2'O-(tert-butyldimethylsilyl)-3',5'-cyclic N-phenylphosphoroamidate (5h)

A solution of palladium acetate (16.9 mg, 0.075 mmol) and triphenylphosphine (41.5 mg, 0.158 mmol) in dry degassed DMF (6 ml) was heated at 50° C. under argon for 15 min (deep red colour) before 2-(tributylstannyl)benzofurane (0.381 g, 0.936 mmol) and (Sp)-8-bromoadenosine-2'O-(tert-butyldimethylsilyl)-3',5'-cyclic N-phenylphosphoramidate (4) (0.450 g, 0.753 mmol) were added. The mixture was heated at 85° C. for 4 h. The solvent was removed under vacuum, the residual material dissolved in dichloromethane (3 ml) and the solution added slowly to vigorously stirred hexane (50 ml). The precipitate was subjected to flash chromatography on silica gel using 70 methanol in dichloromethane; yield: 439 mg (92%). HRMS (electrospray): (M+H) 635.2171. Calc. for $C_{30}H_{35}N_6O_6PSi+H$, 635.2197. $^{31}P$ NMR ($CDCl_3$, 81 MHz) δ 3.05. $^1H$ NMR ($CDCl_3$, 200 MHz): δ 0.00 (3H, s, $CH_3Si$), 0.03 (3H, s, $CH_3Si$), 0.83 (9H, s, $(CH_3)_3C$), 4.4-4.8 (3H, m, H4' H5'), 5.38 (1H, d, J 5.0 Hz, H2'), 5.9-6.1 (1H, m, H3'), 6.58 (1H, s, H1'), 6.61 (1H, br.s, NH), 7.0-7.8 (12H, m, H—Ar, $NH_2$), 8.46 (1H, s, H2). $^{13}C$ NMR ($CDCl_3$, 75 MHz): δ −5.3, −4.7, 18.1, 25.6, 68.8, 70.8, 73.0, 73.1, 94.3, 110.5, 111.8, 119.5, 119.7, 122.0, 123.0, 123.9, 126.4, 127.4, 129.2, 138.6, 141.7, 144.7, 150.5, 153.8, 155.4, 155.8.

EXAMPLE 53

($S_p$)-8-(2-N-Methylpyrrolyl)adenosine-2'O-(tert-butyldimethylsilyl)-3',5'-cyclic N-phenylphosphoramidate (5l)

A mixture of $Pd(OAc)_2$ (37 mg, 0.166 mmol) and $PPh_3$ (91 mg, 0.348 mmol) in DMF (5 ml) was stirred at 50° C. until the solution had turned dark red. ($S_p$)-8-Bromoadenosine-2'O-(tert-butyldimethylsilyl)-3',5'-cyclic N-phenylphosphoramidate (4) (0.500 g, 0.83 mmol) in DMF (2 ml) and 2-(tributylstannyl)-N-methyl-2-pyrrole (0.461 g, 1.24 mmol) were added. The reaction mixture was stirred at 90° C. for 4 h. The DMF was removed at reduced pressure and the residual material subjected to flash chromatography on silica gel using 7.50% MeOH in $CH_2Cl_2$. The product was a white solid contaminated with traces of organotin residues which were removed by dissolution of the product in $CH_2Cl_2$ and re-precipitation by hexane; yield 0.350 g (70%); HRMS (electrospray): M+H 598.2339. Calc. for $C_{27}H_{36}N_7O_5PSi+H$, 598.2357. $^1H$ NMR (CDCl$_3$, 300 MHz): δ −0.13 (6H, s, 2×CH$_3$), 0.66 (9H, s, C(CH$_3$)$_3$), 3.73 (3H, s, N—CH$_3$), 4.35-4.41 (1H, m, H-4'), 4.50-4.66 (2H, m, O—CH$_2$), 5.06 (1H, d, J 5.3, H-2'), 5.80-5.85 (1H, m, H-3'), 5.99 (1H, s, H-1'), 6.19-6.21 (1H, m, H-pyr.), 6.57-6.59 (1H, m, H-pyr), 6.65 (2H, bs, NH$_2$), 6.76-6.78 (1H, m, H-pyr), 6.95 (1H, t, J 7.3 Hz, H-Ph), 7.05 (2H, d, J 7.6 Hz, 2×H-Ph), 7.17 (2H, t, J 7.9 Hz, 2×H-Ph), 7.83 (1H, d, J 9.5 Hz, NH), 8.31 (1H, s, H-2); ). $^{13}$CNMR (CDCl$_3$, 75 MHz): δ −5.5 and −4.9 (2×CH$_3$), 17.9 (Si—C), 25.5 (3×CH$_3$), 36.3 (N—CH$_3$), 68.9 (d, J 6.6 Hz, OCH$_2$), 70.5 (d, J 4.0 Hz, CH-4'), 72.8 (d. J 8.5 Hz, CH-2'), 77.5 (d, J 3.7 Hz, CH-3'), 94.2 (CH-1'), 108.4, 114.2, 119.4, 119.9, 119.9, 122.7, 126.8, 129.2, 129.2, 138.6, 144.2, 149.8, 152.9, 155.5, 162.5.

EXAMPLE 54

($S_p$)-8-(3-Pyridinyl)adenosine-2'O-(tert-butyldimethylsilyl)-3',5'-cyclic N-phenylphosphoramidate (5j)

A mixture of Pd(OAc)$_2$ (37 mg, 0.166 mmol) and PPh$_3$ (91 mg, 0.348 mmol) in NMP (4 ml) was stirred at 50° C. until the solution had turned dark red. A solution of ($S_p$)-8-bromoadenosine-2'O-(tert-butyldimethylsilyl)-3',5'-cyclic N-phenylphosphoramidate (4) (0.500 g, 0.83 mmol) in NMP (2 ml) and 3-(tributylstannyl)pyridine (0.610 g, 1.66 mmol) were added. The reaction mixture was stirred at 110° C. for 10 h before the NMP was removed at reduced pressure and the residual material subjected to flash chromatography on silica gel using 7.5% MeOH in CH$_2$Cl$_2$. The product was a white solid contaminated with traces of organotin residues which were removed by dissolution of the coupling product in CH$_2$Cl$_2$ and reprecipitation by hexane; yield 0.280 g (57%); HRMS (electrospray): M+H 596.2211. Calc. for $C_{21}H_{34}N_7O_5PSi+H$, 596.2201. $^1H$ NMR (CDCl$_3$, 300 MHz): δ (CDCl$_3$) −0.16 (3H, s, CH$_3$), −0.15 (3H, s, CH$_3$), 0.60 (9H, s, C(CH$_3$)$_3$), 4.30-4.43 (1H, m, H-4'), 4.60-4.68 (2H, m, OCH$_2$), 5.15 (1H, d, J 5.2 Hz, H-2'), 5.69 (1H, s, H-1'), 5.75-5.82 (1H, m, H-3'), 6.37 (2H, bs, NH$_2$), 6.58 (1H, d, J 9.2 Hz, NH), 6.99-7.10 (3H, m, 3×H-Ph), 7.17-7.24 (2H, t, J 7.4 Hz, 2×H-Ph), 7.42-7.48 (1H, m, H-pyr), 8.02-8.06 (1H, m, H-pyr), 8.37 (1H, s, H-2), 8.76-8.79 (1H, m, H-pyr), 8.97 (1H, d, J 1.7 Hz, H-pyr); $^{13}$C NMR (CDCl$_3$, 75 MHz): δ −5.5 and −4.8 (2×CH$_3$), 18.0 (Si—C), 25.4 (3×CH$_3$), 68.9 (d, J 6.8 Hz, OCH$_2$), 71.3 (d, J 4.5 Hz, CH-4'), 73.3 (d. J 8.8 Hz, CH-2'), 77.5 (d, J 3.8 Hz, CH-3'), 94.2 (CH-1'), 119.4, 119.5, 119.6, 122.9, 123.5, 125.0, 129.1, 129.1, 136.8, 138.5, 148.1, 149.8, 150.3, 151.4, 153.5, 155.9.

EXAMPLE 55

($S_p$)-8-(Phenyl)adenosine-2'O-(tert-butyldimethylsilyl)-3',5'-cyclic-N-phenylphosphoramidate (5k)

A mixture of Pd(OAc)$_2$ (37 mg, 0.166 mmol) and PPh$_3$ (91 mg, 0.348 mmol) in DMF (4 ml) was stirred at 50° C. until the solution had turned dark red. A solution of ($R_p$)-8-bromoadenosine-2'O-(tert-butyldimethylsilyl)-3',5'-cyclic N-phenylphosphoramidate (4) (0.500 g, 0.83 mmol) in NMP (2 ml) and phenyltributylstannane (0.609 g, 1.66 mmol) were added. The reaction mixture was stirred at 135° C. for 7 h before the NMP was removed at reduced pressure and the residual material subjected to flash chromatography on silica gel using 7.5V MeOH in CH$_2$Cl$_2$. The product was a white solid contaminated with traces of organotin residues which were removed by dissolution of the product in CH$_2$Cl$_2$ and repre-cipitation by hexane; yield 0.310 g (63%); HRMS (electrospray): M+H 595.2275. Calc. for $C_{28}H_{31}N_6O_5PSi+H$, 595.2248. $^1H$ NMR (CDCl$_3$, 300 MHz) δ −0.21 (6H, s, 2×CH$_3$), 0.57 (9H, s, C(CH$_3$)$_3$), 4.32-4.36 (1H, m, H-4'), 4.52-4.63 (2H, m, OCH$_2$), 4.99 (1H, d, J 5.1 Hz, H-2'), 5.75 (1H, s, H-1'), 5.76-5.83 (1H, m, H-3'), 6.35 (2H, bs, NH$_2$), 6.93 (1H, t, J 7.3 Hz, H-Ph), 7.03 (2H, d, J 8.0 Hz, 2×H-Ph), 7.16 (2H, t, J 7.9 Hz, 2×H-Ph), 7.33 (1H, d, J 9.4 Hz, NH), 7.51-7.54 (3H, m, H-Ph), 7.63 (2H, d, J 7.7 Hz, H-Ph), 8.26 (1H, s, H-2); $^{13}$C NMR (CDCl$_3$, 75 MHz): δ −5.8 and −5.0 (2×CH$_3$), 17.7 (Si—C), 25.2 (3×CH$_3$), 68.9 (d, J 6.7 Hz, OCH$_2$), 70.5 (d, J 4.2 Hz, CH-4$^1$), 72.8 (d. J 8.6 Hz, CH-2'), 76.9 (d, J 3.8 Hz, CH-3'), 94.1 (CH-1'), 118.7, 119.1, 119.1, 119.2, 119.2, 122.8, 127.9, 128.9, 128.9, 129.2, 129.2, 130.8, 138.3, 150.1, 151.2, 152.9, 155.2.

EXAMPLE 56

($S_p$)-8-(4-Methoxyphenyl)adenosine-2'O-(tert-butyldimethylsilyl)-3',5'-cyclic N-phenylphosphoramidate (5l)

A mixture of Pd(OAc)$_2$ (37 mg, 0.166 mmol) and PPh$_3$ (91 mg, 0.348 mmol) in DMF (4 ml) was stirred at 50° C. until the solution had become dark red. A solution of ($S_p$)-8-bromoadenosine-2'O-(tert-butyldimethylsilyl)-3',5'-cyclic N-phenylphosphoramidate (4) (0.500 g, 0.83 mmol) in NMP (2 ml) and 4-(tributylstannyl)anisole (0.666 g, 1.66 mmol) were added. The reaction mixture was stirred at 120-125° C. for 10 h before the NMP was removed at reduced pressure. The residual material was subjected to flash chromatography on silica gel using 7.5w MeOH in CH$_2$Cl$_2$. The product was a white solid which was contaminated with traces of organotin residues which were removed by dissolution in CH$_2$Cl$_2$ and re-precipitation by hexane; yield 0.315 g (61%); HRMS (electrospray): M+H 625.2368. Calc. for $C_{29}H_{37}N_6O_6PSi+H$, 625.2354. $^1H$. NMR (CDCl$_3$, 300 MHz): δ −0.15 (3H, s, CH$_3$), −0.14 (3H, s, CH$_3$), 0.62 (9H, s, C(CH$_3$)$_3$), 3.85 (3H, s, OCH$_3$), 4.32-4.37 (1H, m, H-4'), 4.55-4.69 (2H, m, OCH$_2$), 5.07 (1H, d, J 5.3 Hz, H-2'), 5.78 (1H, s, H-1'), 5.79-5.88 (1H, m, H-3'), 6.20 (2H, bs, NH$_2$), 6.90 (1H, d, J 9.3 Hz, NH), 6.94-7.08 (5H, m, 5×H-Ph), 7.19 (2H, t, J 7.4 Hz, 2×H-Ph), 7.62 (2H, d, J 6.9 Hz, 2×H-Ph), 8.35 (1H, s, H-2); $^{13}$C NMR (CDCl$_3$, 75 MHz): δ −5.4 and −4.7 (2×CH$_3$), 18.0 (Si—C), 25.5 (3×CH$_3$), 55.4 (OCH$_3$), 69.0 (d, J 6.9 Hz, OCH$_2$), 70.7 (d, J 4.2 Hz, CH-4'), 72.8 (d, J 8.6 Hz, CH-2'), 76.9 (d, J 3.8 Hz, CH-3'), 94.3 (CH-1'), 114.5, 114.5, 119.3, 119.5, 119.5, 119.6, 119.6, 120.7, 123.0, 129.2, 129.2, 130.9, 130.9, 138.4, 150.4, 151.5, 152.8, 155.2, 161.5.

EXAMPLE 57

($S_p$)-8-(2-Thiazolyl)adenosine-2'O-(tert-butyldimethylsilyl)-3',5'-cyclic N-phenylphosphoramidate (5m)

A solution of Pd(OAc)$_2$ (27 mg, 0.10 mmol) and PPh$_3$ (62 mg, 0.20 mmol) in DMF (5 ml) was stirred at 50° C. for 30 min before 2-(tributylstannyl)thiazole (260 mg, 0.70 mmol) was added followed by ($S_p$)-8-bromadenosine-2'O-(tert-butyldimethylsilyl)-3',5'-cyclic N-phenylphosphoramidate (4) (340 mg, 0.58 mmol). The mixture was stirred at 85° C. for 3 h. The solvent was evaporated and the residue purified by flash chromatography on silica gel using CH$_2$Cl$_2$:MeOH 3:97 and 5:9, yield: 160 mg (47%) of a tan solid. MS (electrospray) 602.2; $^{31}$P NMR (CDCl$_3$, 81 MHz): δ 2.71; $^1H$ NMR (CDCl$_3$, 200 MHz): δ −0.04 (6H, s, SiMe), 0.75 (9H, s, Si-tBu), 4.44-4.77 (3H, m, 5.42 (d, J 5.1 Hz), 5.77-5.85 (1H, m), 5.96 (1H, s), 6.44 (2H, br.s, NH$_2$), 6.96-7.35 (6H, m), 8.40 (1H, s), 8.47 (1H, s), 9.06 (1H, s,).

EXAMPLE 58

(R$_p$)-8-(2-Thiazolyl)adenosine-3',5'-cyclic phosphorothioic acid ammonium salt (7m)

A 1.0 M solution of t-BuOK in THF (0.29 ml, 0.29 mmol) was added to a solution of (S$_p$)-8-(2-thiazolyl)adenosine-2'O-(tert-butyldimethylsilyl)-3',5'-cyclic N-phenyl-phosphoramidate (5m) (136 mg, 0.23 mmol) in THF (3 ml) at room temperature. The mixture was stirred for 1 h before carbon disulfide (0.04 ml, 0.7 mmol) was added. The mixture stirred for another 3 h at room temperature. The volume of the solvent was reduced to about 1 ml before hexane (30 ml) was added. The precipitate formed and was isolated by filtration. The crude product was dissolved in DMF (2 ml), NH$_4$F (52 mg, 1.4 mmol) added and the mixture stirred under argon at 40° C. for 48 h. The solvent was evaporated off and the crude product was purified by flash chromatography on silica gel, using iPrOH:EtOAc:H$_2$O:NH$_3$(aq) 7:7:1:1; yield 54 mg (53%) of a white solid. HRMS (electrospray) M 427.0047. Calc. for C$_{13}$H$_{12}$N$_6$O$_5$PS$_2$: 427.0048. $^{31}$P NMR (DMSO-d$_6$, 81 MHz): δ 54.02; $^1$H NMR (DMSO-d$_6$, 200 MHz): δ 3.95-4.15 (3H, m), 4.92-5.12 (2H, m), 6.60-7.30 (4H, br.s), 7.50 (2H, s,), 8.22 (1H, s), 8.34 (1H, s), 9.36 (1H, d, J 0.5 Hz).

EXAMPLE 59

(Rp)-8-(5-Methyl-2-furyl)adenosine-3',5'-cyclic phosphorothioic acid tributylammonium salt (8e)

1 M Sodium t-butoxide (0.60 ml) was added to a solution of (Sp)-8-(5-methyl-2-furyl)-adenosine-2'O-(tert-butyldimethylsilyl)-3',5'-cyclic N-phenylphosphoramidate (5e) (0.350 g, 0.552 mmol) in dry THF (7 ml) under argon gas. The mixture was stirred for 30 min before carbon disulphide (0.126 g, 1.66 mmol) was added and the stirring continued for 3 h. The reaction mixture was added slowly to hexane, the precipitate filtered off and dissolved in water (10 ml). 1 M HCl was added dropwise with vigorous stirring to the ice-cold reaction mixture until pH 3. The precipitated thioic acid 6e was filtered off, washed with cold water and dried under high vacuum; yield 0.270 g of a yellow solid. The acid (6e) was then dissolved in DMF (3 ml) under argon and ammonium fluoride (0.056 g, 1.5 mmol) added. The mixture was stirred for 3 d at 40° C. when excess tributylamine was added. All volatile materials were distilled off at reduced pressure and the residual material subjected to flash chromatography on silica gel using 1% tributylamine and 5% methanol in dichloromethane. The thioate product contained some free tributylamine which was removed by repeated washings with hexane; yield: 0.276 g (82%). HRMS (electrospray): M 424.0488. Calc. for C$_{15}$H$_{15}$N$_5$O$_6$PS$^-$: 424.0487. $^{31}$P NMR (CDCl$_3$, 81 MHz): δ 57.0. $^1$H NMR (CDCl$_{31}$ 200 MHz): δ 1.00 (9H, t, J 7.2 Hz, CH$_2$CH$_3$), 1.3-1.5 (6H, m, CH$_2$), 1.7-1.9 (6H, m, CH$_2$), 2.44 (3H, s, CH$_3$Fur), 3.05 (6H, t, J 6.5 Hz, NCH$_2$), 4.4-4.6 (3H, m, H4' H5'), 5.24 (1H, d, J 4.8 Hz, H2'), 5.5-5.6 (1H, m, H3'), 6.20-6.24 (4H, m, H1' H-Fur NH$_2$), 7.06 (1H, d, J 3.3 Hz, H-Fu), 8.24 (1H, s, H2). $^{13}$C NMR (CDCl$_3$, 75 MHz): δ 13.4, 19.7, 24.9, 30.6, 51.7, 67.0, 71.1, 71.2, 71.5, 92.2, 108.1, 115.2, 119.0, 140.7, 142.4, 149.9, 152.0, 154.8, 155.3.

EXAMPLE 60

(Rp)-8-(5-Methoxy-2-furyl)adenosine-3',5'-cyclic phosphorothioic acid tributylammonium salt (8f)

1 M Sodium t-butoxide (0.50 ml) was added to a solution of (Sp)-8-(5-methoxy-2-furyl)-adenosine-2'O-(tert-butyldimethylsilyl)-3',5'-cyclic N-phenylphosphoramidate (5f) (0.280 g, 0.456 mmol) in dry THF (6 ml) under argon gas. The mixture was stirred for 30 min before carbon disulphide (0.104 g, 1.3 mmol) was added and the stirring continued for 3 h. The reaction mixture was added slowly to hexane, the precipitate filtered off and dissolved in water (10 ml). 1 M HCl was added dropwise with vigorous stirring to the ice cold reaction mixture until pH 3. The precipitated thioic acid 6f was filtered off, washed with cold water and dried under high vacuum; yield 0.127 g of a brown solid. The thioic acid 6f was dissolved in dry DMF (2 ml) under argon and ammonium fluoride (0.037 g, 1 mmol) added. The mixture was stirred for 3 d at 40° C. before excess tributylamine was added. Evaporation under reduced pressure removed all volatile materials. The residual material was subjected to flash chromatography on silica gel using 1l tributylamine and 5% methanol in dichloromethane. Free tributylamine present in the thioate product removed by repeated washing with hexane; yield: 0.109 g (29%). HRMS (electrospray): M 440.0427. Calc. for C$_{15}$H$_{15}$N$_5$O$_7$PS$^-$: 440.0436. $^{31}$P NMR (CDCl$_3$, 81 MHz): δ 57.0. $^1$H NMR (CDCl$_3$, 200 MHz): δ 0.99 (9H, t, J 7.2 Hz, CH$_2$CH$_3$), 1.3-1.5 (6H, m, CH$_2$), 1.7-1.9 (m, 6H, CH$_2$), 3.05 (t, J 6.5 Hz, 6H, NCH$_2$), 3.89 (3H, s, CH$_3$O), 4.3-4.5 (3H, m, H4' H5'), 5.24 (1H, d, J 5.2 Hz, H2'), 5.6-5.7 (1H, m, H3'), 6.21 (1H, s, H1'), 6.41 (2H, br.s, NH$_2$), 6.89 (1H, d, J 8.4 Hz, H-Fur), 7.66 (1H, d, J 8.6 Hz, H-Fur), 8.35 (1H, s, H2). $^{13}$CNMR (CDCl$_3$, 75 MHz): δ 13.3, 19.8, 24.8, 51.6, 69.2, 70.6, 72.8, 76.4, 83.0, 94.2, 116.9, 119.4, 132.7, 138.7, 150.0, 152.8, 155.1, 163.3.

EXAMPLE 61

(Rp)-8-(2-Hydroxymethyl-5-furyl)adenosine-3',5'-cyclic phosphorothioic acid tributylammonium salt (8g)

1 M Sodium t-butoxide (0.62 ml) was added to a solution of (Sp)-8-(5-tert-butyldimethylsilyloxymethyl)-2-furyl)adenosine-2'O-(tert-butyldimethylsilyl)-3',5'-cyclic N-phenylphosphoramidate (5g) (0.410 g, 0.563 mmol) in dry THF (7 ml) under argon. The mixture was stirred for 30 min before carbon disulfide (0.128 g, 1.69 mmol) was added. The reaction mixture was stirred for 3 h before being added dropwise to hexane. The precipitate formed was re-dissolved in water. Slow addition of 1 M HCl to the ice cold vigorously stirred aqueous solution until pH 3 precipitated the thioic acid 6g which was filtered off, washed with cold water and dried under high vacuum to yield the thioic acid as a brown solid (0.294 g). The product was redissolved in dry DMF (3 ml) under argon and ammonium fluoride (0.097 g, 2.63 mmol) added. The mixture was stirred at 40° C. for 3 d before excess tributylamine was added. Distillation under reduced pressure removed all volatile material and the residual material was subjected to flash chromatography on silica gel using 1% tributylamine and 5% methanol in dichloromethane. The product contained some free tributylamine which was removed by repeated washings with hexane; yield 0.243 g (69%). HRMS (electrospray): M 440.043. Calc. for $C_{15}H_{15}N_5O_7PS^-$: 440.0436. $^{31}P$ NMR (CDCl$_3$, 81 MHz): δ 57.0. $^1H$ NMR (CDCl$_3$, 200 MHz): δ 1.00 (9H, t, J 7.1 Hz, CH$_2$CH$_3$), 1.3-1.5 (6H, m, CH$_2$), 1.7-1.9 (6H, m, CH$_2$), 2.9-3.1 (6H, m, NCH$_2$), 4.4-4.6 (3H, m, H4' H5'), 4.85 (2H, s, HOCH$_2$Fur), 5.26 (1H, d, J 5.0 Hz, H2'), 5.5-5.6 (1H, m, H3'), 6.2-6.3 (4H, m, H1' H-Fur NH$_2$), 7.12 (1H, d, J 8.3 Hz, H-Fur), 8.22 (1H, s, H2). $^{13}C$ NMR (CDCl$_3$, 75 MHz): δ: 13.4, 19.7, 24.9, 57.2, 51.7, 67.7, 71.1, 72.6, 75.9, 94.3, 108.8, 115.5, 119.1, 141.2, 149.5, 141.6, 150.2, 153.7, 155.2.

EXAMPLE 62

(Rp)-8-(2-Benzofuryl)adenosine-3',5'-cyclic phosphorothioic acid tributylammonium salt (8h)

1 M Sodium t-butoxide (0.69 ml) was added to a solution of (Sp)-8-(2-benzofuryl)-adenosine-2'O-(tert-butyldimethylsilyl)-3',5'-cyclic N-phenylphosphoramidate (5h) (0.400 g, 0.631 mmol) in dry THF (8 ml) under argon. The mixture was stirred for 30 min before carbon disulphide (0.143 g, 1.89 mmol) was added and the stirring continued for 3 h. The reaction mixture was slowly added to hexane, the precipitate filtered off and dissolved in water (4 ml). Slow addition of 1 M HCl to the ice cold vigorously stirred aqueous solution until pH 3 precipitated the thioic acid 6h which was filtered off, washed with cold water and dried under high vacuum to furnish a brown solid (0.221 g). The product was redissolved in dry DMF (2 ml) under argon and ammonium fluoride (0.043 g, 1.1 mmol) added. The mixture was stirred at 40° C. for 3 d and excess tributylamine added. The volatile materials were removed by distillation at reduced pressure and the residual material subjected to flash chromatography on silica gel using 1% tributylamine and 5% methanol in dichloromethane. The product was washed repeatedly with hexane to remove free tributylamine; yield 0.155 g (38%). HRMS (electrospray): M 460.0461. Calc. for $C_{18}H_{15}N_5O_6PS^-$: 460.0487. $^{31}P$ NMR (CDCl$_3$, 81 MHz): δ 57.0. $^1H$ NMR (CDCl$_3$, 200 MHz): δ 1.00 (9H, t, J 7.2 Hz, CH$_2$CH$_3$), 1.3-1.5 (6H, m, CH$_2$), 1.7-1.9 (6H, m, CH$_2$), 3.08 (6H, t, J 6.4 Hz, NCH$_2$), 4.4-4.6 (3H, m, H4' H5'), 5.33 (1H, d, J 5.2 Hz, H2'), 5.9-6.1 (1H, m, H3'), 6.43 (1H, s, H1'), 7.3-7.7 (5H, m, H—Ar), 8.31 (1H, s, H2). $^{13}C$ NMR (CDCl$_3$, 75 MHz): δ 13.4, 19.8, 24.8, 51.6, 66.3, 72.4, 72.8, 75.5, 94.6, 111.8, 112.6, 120.0, 123.7, 124.3, 127.0, 128.3, 126.4, 149.9, 153.1, 154.2, 154.4, 155.8

EXAMPLE 63

($R_p$)-8-(2-N-Methylpyrrolyl)adenosine-3',5'-cyclic phosphorothioic acid tributylammonium salt (8i)

A mixture of ($S_p$)-8-(2-N-methylpyrrolyl) adenosine-2'O-(tert-butyldimethylsilyl)-3,5'-cyclic N-phenyl-phosphoramidate (Si) (0.300 g, 0.5 mmol) in dry THF (6 ml) and potassium tert-butoxide (0.62 ml, 0.62 mmol, 1 M in THF) was stirred under argon at room temperature for 1 h before carbon disulfide (0.09 ml, 1.5 mmol) was added. The reaction mixture was stirred at room temperature for 3 h before most of the solvent was distilled off at reduced pressure. Addition of diethyl ether gave a solid precipitate which was dissolved in water (9 ml) and 1.2 M HCl (1.25 ml) added at 0° C. The precipitate was the silylated (R)-8-(2-N-methylpyrrolyl)adenosine-3',5'-cyclic phosphorothioic acid 61. The product was well dried in vacuum before the solid (0.170 g, 0.3 mmol) was dissolved in DMF (1.5 ml) under argon and ammonium fluoride (0.075 g, 2.0 mmol) added. The reaction mixture was stirred at room temperature for 5 d before tributylamine (0.111 g, 0.6 mmol) was added to generate a clear solution. The volatile materials were removed at reduced pressure, the residue triturated with hexane to remove any tributylamine and the residual material subjected to flash chromatography on silica gel using CH$_2$Cl$_2$:CH$_3$OH:NBu$_3$ 100:10:1. The ammonium salt, which contained some free tributylamine, was further purified by dissolution in CH$_2$Cl$_2$ and precipitation with hexane; yield 0.105 g (34% from Si) of a white solid. HRMS (electrospray): M-NHBu$_3$ 423.0647. Calc. for $C_{27}H_{44}N_7O_5PS$—NH(C$_4$H$_9$)$_3$: 423.0646. $^1H$ NMR (CDCl$_3$, 300 MHz, CH$_3$OD): δ 0.93 (9H, t, J 7.3 Hz, 3×CH$_3$), 1.29-1.41 (6H, m, 3×CH$_2$), 1.55-1.65 (6H, m, 3×CH$_2$), 2.98-3.04 (6H, m, 3×CH$_2$), 3.78 (3H, s, N—CH$_3$), 4.12-4.24 (1H, m, H-4'), 4.25-4.30 (2H, m, OCH$_2$), 4.96 (1H, d, J 5.3 Hz, H-2'), 5.49 5.57 (1H, m, H-3'), 5.94 (1H, s, H-1'), 6.25-6.28 (1H, m, H-pyr), 6.60-6.62 (1H, m, H-pyr), 6.93-6.95 (1H, m, H-pyr), 8.13 (1H, s, H-2). $^{13}C$ NMR (CH$_3$OD, 75 MHz): δ 13.9 (3×CH$_3$), 20.9 (3×CH$_2$), 26.9 (3×CH$_2$), 35.7 (N—CH$_3$), 54.0 (3×CH$_2$), 68.5 (d, J 9.8 Hz, OCH$_2$), 72.8 (d, J 7.6 Hz, CH-4'), 73.1 (d. J 5.7 Hz, CH-2'), 77.7 (d, J 6.6 Hz, CH-3'), 94.2 (CH-1'), 109.4, 120.1, 121.1, 128.4, 146.3, 151.2, 153.6, 156.8.

EXAMPLE 64

($R_p$)-8-(3-Pyridinyl)adenosine-3',5'-cyclic-phosphorothioic acid tributylammonium salt (8j)

A mixture of ($S_p$)-8-(3-pyridinyl)adenosine-2'O-(tert-butyldimethylsilyl)-3',5'-cyclic N-phenylphosphoramidate (5j) (0.300 g, 0.5 mmol) and potassium tert-butoxide (0.62 ml, 0.62 mmol, 1 M in THF) in THF (6 ml) under argon was stirred at room temperature for 1 h before carbon disulfide (0.09 ml, 1.5 mmol) was added. The reaction mixture was stirred at room temperature for 3 h. The solvent was partially removed at reduced pressure and hexane added until precipitation was complete. The precipitate was redissolved in water (9 ml) and 1.2 M HCl (1.25 ml) was added at 0° C. The precipitated silylated ($R_p$)-8-(3-pyridinyl)adenosine-3',5'-cyclic phosphorothioic acid 6j was collected by filtration and dried overnight at high vacuum. Most of this material (0.180 g, 0.33 mmol) was dissolved in dry DMF (1.5 ml) under argon and ammonium fluoride (0.075 g, 2 mmol) added. The mixture was stirred at room temperature for 5 days and filtered. Tributylamine (0.111 g, 0.6 mmol) was added to the filtrate before evaporation at reduced pressure. The residual material was triturated with hexane to remove excess of tributylamine and subjected to flash chromatography on silica gel using CH$_2$Cl$_2$:CH$_3$OH:NBu$_3$ 100:10:1. The ammonium salt, which contains traces of tributylamine, was further purified by dissolution in CH$_2$Cl$_2$ and reprecipitation by addition of diethyl ether; yield 0.100 g (34% from 5j) of a white solid. HRMS (electrospray): M-NHBu$_3$ 421.0492. Calc. for $C_{27}H_{42}N_7O_5PS$—NH(C$_4$H$_9$)$_3$: 421.0489. $^1H$ NMR (CDCl$_3$, 300 MHz): δ 0.93 (9H, t, J 7.2 Hz, 3×CH$_3$), 1.29-1.43 (6H, m, 3×CH$_2$), 1.67-1.79 (6H, m, 3×CH$_2$), 2.98 3.06 (6H, m, 3×CH$_2$), 4.30-4.44 (3H, m, H-4' and OCH$_2$), 5.14 (1H, d, J 5.2 Hz, H-2'), 5.50-5.57 (1H, m, H-3'), 5.71 (1H, s, H-1'), 6.00 (2H, bs, NH$_2$), 7.38-7.45 (1H, m, H-pyr), 8.03-8.09 (1H, m, H-pyr), 8.19 (1H, s, H-2), 8.70-8.73 (1H, m, H-pyr), 9.01 (1H, d, J 1.6 Hz, H-pyrid) $^{13}C$ NMR (CDCl$_3$, 75 MHz): δ 13.6 (3×CH$_3$), 20.1 (3×CH$_2$), 25.2 (3×CH$_2$), 51.9 (3×CH$_2$), 67.2 (d, J 9.7 Hz, OCH$_2$), 71.6 (d, J 7.4 Hz, CH-4'), 71.8 (d. J 6.5 Hz, CH-2'), 77.2 (d, J 6.2 Hz, CH-3'), 92.6 (CH-1'), 120.1, 124.0, 125.7, 137.3, 149.3, 150.6, 151.1, 151.7, 153.3, 155.8.

EXAMPLE 65

($R_p$)-8-Phenyladenosine-3',5'-cyclic phosphorothioic acid tributylammonium salt (8k)

A mixture of ($S_p$)-8-(phenyl)adenosine-2'O-(tert-butyldimethylsilyl)-3',5'-cyclic N-phenylphosphoramidate (5k) (0.250 g, 0.42 mmol) and potassium tert-butoxide (0.52 ml, 0.52 mmol, 1 M in THF (6 ml) was stirred under argon at room temperature for 1 h before carbon disulfide (0.08 ml, 1.26 mmol) was added. The reaction mixture was stirred at room temperature for 3 h and most of the solvent was evaporated off. Hexane was added to the residue until precipitation was complete. The solid precipitate was dissolved in water (9 ml) and 1.2 M HCl (1.05 ml) was added at 0° C. The product was the silylated ($R_p$)-8-phenyladenosine-3',5'-cyclic phosphorothioic acid. Part of this material (0.210 g, 0.39 mmol) was dissolved in dry DMF (2 ml) under argon and ammonium fluoride (0.100 g, 2.73 mmol) added. The mixture was stirred at room temperature for 5 days. The reaction mixture was filtered and tributylamine (0.144 g, 0.78 mmol) added to the filtrate. The volatile materials were distilled off at reduced pressure and the residual material triturated with hexane to remove any free tributylamine. The remaining material was subjected to flash chromatography on silica gel using $CH_2Cl_2:CH_3OH:NBu_3$ 100:10:1. The ammonium salt, which contained tributylamine, was further purified by dissolution in $CH_2Cl_2$ and reprecipitation with hexane; yield 0.100 g (39% from 5k) of a white solid. HRMS (electrospray): M-NHBu$_3$ 420.0534. Calc. for $C_{21}H_{43}N_6O_5PS$—NH($C_4H_9$)$_3$: 420.0537. $^1$H NMR (CH$_3$OD, 300 MHz): δ 0.94 (9H, t, J 7.3 Hz, 3×CH$_3$), 1.32-1.41 (6H, m, 3×CH$_2$), 1.59-1.66 (6H, m, 3×CH$_2$), 3.03-3.09 (6H, m, 3×CH$_2$), 4.10-4.15 (1H, m, H-4'), 4.25-4.33 (2H, m, OCH$_2$), 4.98 (1H, d, J 5.3 Hz, H-2'), 5.47-5.54 (1H, m, H-3'), 5.71 (1H, s, H-1'), 7.52-7.55 (3H, m, H-Ph), 7.72-7.75 (2H, m, H-Ph), 8.17 (1H, s, H-2). $^{13}$C NMR (CH$_3$OD, 75 MHz): δ 13.9 (3×CH$_3$), 20.9 (3×CH$_2$), 26.9 (3×CH$_2$), 54.0 (3×CH$_2$), 68.4 (d, J 9.7 Hz, OCH$_2$), 72.8 (d, J 7.6 Hz, CH-4'), 73.2 (d. J 5.7 Hz, CH-2'), 77.7 (d, J 6.6 Hz, CH-3'), 94.2 (CH-1'), 130.0, 130.1, 130.1, 130.7, 130.7, 131.9, 151.7, 153.1, 153.9, 157.0.

EXAMPLE 66

($R_p$)-8-(4-Methoxyphenyl)adenosine-3',5'-cyclic phosphorothioic acid tributylammonium salt (8l)

A mixture of ($R_p$)-8-(4-methoxyphenyl)adenosine-2O-(tert-butyldimethylsilyl)-3',5'-cyclic N-phenylphosphoramidate (5l) (0.300 g, 0.48 mmol) and potassium tert-butoxide (0.6 ml, 0.6 mmol, 1 M in THF) in THF (6 ml) under argon was stirred at room temperature for 1 h before carbon disulfide (0.09 ml, 1.44 mmol) was added. The reaction mixture was stirred at room temperature for 3 h when most of the solvent was distilled off at reduced pressure and diethyl ether added until the precipitation was complete. The precipitate was redissolved in water (9 ml) and 1.2 M HCl (1.2 ml) added at 0° C. The silylated ($R_p$)-8-(4-methoxyphenyladenosine)-3',5'-cyclic phosphorothioic acid 6l was collected by filtration and dried overnight at high vacuum. A part of the dried product (0.250 g, 0.44 mmol) was dissolved in dry DMF (2 ml) under argon and ammonium fluoride (0.104 g, 2.8 mmol) added. The mixture was stirred at room temperature for 5 days and filtered. Tributylamine (0.163 g, 0.88 mmol) was added to the filtrate and the solvent removed at reduced pressure. The residual material was extracted with hexane to remove any excess of tributylamine and the residue subjected to flash chromatography on silica gel using $CH_2Cl_2:CH_3OH:NBu_3$ 100:10:1. The ammonium salt, which contained some free tributylamine, was further purified by dissolution in $CH_2Cl_2$ and precipitation with hexane; yield 0.130 g (426 from 5l) of a white solid. HRMS (electrospray): M-NHBu$_3$ 450.0648. Calc. for $C_{29}H_{45}N_6O_6PS$—NH($C_4H_9$)$_3$: 450.0642. $^1$H NMR (CH$_3$OD, 300 MHz): δ 0.93 (9H, t, J 7.3 Hz, 3×CH$_3$), 1.29-1.42 (6H, m, 3×CH$_2$), 1.58-1.69 (6H, m, 3×CH$_2$), 3.04-3.24 (6H, m, 3×CH$_2$), 3.81 (3H, s, OCH$_3$), 4.10-4.17 (1H, m, H-4'), 4.25-4.33 (2H, m, O—CH$_2$), 4.97 (1H, d, J 5.3, H-2'), 5.46-5.52 (1H, m, H-3'), 5.71 (1H, s, H-1'), 7.0 (2H, d, J 8.6 Hz, 2×H-Ph), 7.6 (2H, d, J 8.6 Hz, 2×H-Ph), 8.14 (1H, s, H-2); $^{13}$C NMR (CH$_3$OD, 75 MHz): δ 14.0 (3×CH$_3$), 21.0 (3×CH$_2$), 26.9 (3×CH$_2$), 54.0 (3×CH$_2$), 56.1 (OCH$_3$), 68.5 (d, J 9.7 Hz, OCH$_2$), 72.8 (d, J 7.6 Hz, CH-4'), 73.2 (d. J 5.7 Hz, CH-2'), 77.7 (d, J 6.6 Hz, CH-3'), 94.4 (CH-1'), 115.6, 115.6, 119.8, 121.9, 132.2, 151.7, 153.3, 153.4, 156.6, 163.3.

EXAMPLE 67

($R_p$)-8-(2-N-Methylpyrrolyl)-3',5'-cyclic phosphorothioic acid sodium salt (9i)

($R_p$)-8-(N-Methyl-2-pyrrolyl)-3,5'-cyclic phosphorothioic acid ammonium salt (5i) (0.100 g, 0.16 nmol) was dissolved in 0.1 M NaOH in MeOH (1.7 ml). The sodium salt was precipitated by addition of diethyl ether and collected by filtration; yield 0.060 g (84%) of a white solid material. HRMS (electrospray): M-Na 423.0630. Calc. for $C_{15}H_{16}N_6O_5PS$—Na: 423.0646. $^1$H NMR (CH$_3$OD, 300 MHz): δ 3.86 (3H, s, N—CH$_3$), 4.22-4.41 (3H, m, H-4' and OCH$_2$), 5.04 (1H, d, J 5.3 Hz, H-2'), 5.49-5.56 (1H, m, H-3'), 5.93 (1H, s, H-1'), 6.25-6.29 (1H, m, H-Pyr), 6.67-6.70 (1H, m, H-Pyr), 7.01-7.03 (1H, m, H-Pyr), 8.22 (1H, s, H-2); $^{13}$C NMR (CH$_3$OD, 75 MHz): δ 35.7 (N—CH$_3$), 68.5 (d, J 9.8 Hz, OCH$_2$), 72.8 (d, J 7.6 Hz, CH-4'), 73.1 (d. J 5.7 Hz, CH-2'), 77.7 (d, J 6.6 Hz, CH-3'), 94.2 (CH-1'), 109.4, 120.1, 121.1, 128.4, 146.3, 151.2, 153.6, 156.8.

EXAMPLE 68

($R_p$)-8-(3-Pyridinyl)adenosine-3',5'-cyclic phosphorothioic acid sodium salt (9j)

($R_p$)-8-(3-Pyridinyl)adenosine-3',5'-cyclic phosphorothioic acid tributylammonium salt (8j) (0.100 g, 0.16 mmol) was dissolved in 0.1 M NaOH in MeOH (1.7 ml). Addition of diethyl ether precipitated the sodium salt; yield 0.057 g (80%) of a white solid material. HRMS (electrospray): M-Na 421.0495. Calc. for $C_{15}H_{14}N_6O_5PS$—Na: 421.0489. $^1$H NMR (CH$_3$OD, 300 MHz): δ 4.16-4.31 (3H, m, H-4' and OCH$_2$), 5.03 (1H, d, J 5.1 Hz, H-2'), 5.41-5.45 (1H, m, H-3'), 5.64 (1H, s, H-1'), 7.57-7.61 (1H, m, H-pyrid), 8.18-8.22 (1H, m, H-pyrid), 8.19 (1H, s, H-2), 8.68-8.71 (1H, m, H-pyrid), 8.92 (1H, d, J 1.4 Hz, H-pyrid). $^{13}$C NMR (CH$_3$OD, 75 MHz): δ 68.3 (d, J 9.4 Hz, OCH$_2$), 72.7 (d, J 7.7 Hz, CH-4'), 73.3 (d. J 5.6 Hz, CH-2'), 77.6 (d, J 6.4 Hz, CH-3'), 94.2 (CH-1'), 120.3, 125.3, 127.2, 138.9, 149.7, 150.6, 151.8, 151.9, 154.3, 157.3.

EXAMPLE 69

($R_p$)-8-Phenyladenosine-3',5'-cyclic phosphorothioic acid sodium salt (9k)

($R_p$)-8-Phenyladenosine-3',5'-cyclic phosphorothioic acid tributylammonium salt (8k) (0.100 g, 0.16 mmol) was dissolved in 0.1 M NaOH in MeOH (1.7 ml). The sodium salt was precipitated on addition of diethyl ether; yield 0.053 g (75%) of a white solid. HRMS (electrospray): M-Na 420.0529. Calc. for $C_{16}H_{15}N_5O_5PS$—Na: 420.0537. $^1$H NMR (CH$_3$OD, 300 MHz): δ 4.16-4.40 (3H, m, H-4' and OCH$_2$), 5.03 (1H, d, J 5.3 Hz, H-2'), 5.50-5.58 (1H, m, H-3'), 5.76 (1H, s, H-1'), 7.57-7.60 (3H, m, H-Ph), 7.76-7.81 (2H, m, H-Ph), 8.21 (1H, s, H-2). $^{13}$C NMR (CH$_3$OD, 75 MHz): δ 68.4 (d, J 9.7 Hz, OCH$_2$), 72.8 (d, J 7.6 Hz, CH-4'), 73.3 (d. J 5.7 Hz, CH-2'), 77.7 (d, J 6.4 Hz, CH-3'), 94.2 (CH-1'), 130.0, 130.1, 130.1, 130.7, 130.7, 131.9, 151.7, 153.1, 154.0, 157.0.

EXAMPLE 70

($R_p$)-8-(4-Methoxyphenyl)adenosine-3',5'-cyclic-phosphorothioic acid sodium salt (9l)

($R_p$)-8-(4-Methoxyphenyl)adenosine-3',5'-cyclic phosphorothioic acid tributylammonium salt (8l) (0.090 g, 0.14 mmol) was dissolved in 0.1 M NaOH in MeOH (1.5 ml). The sodium salt was precipitated by addition of diethyl ether; yield 0.050 g (75%) of a white solid. HRMS (electrospray): M-Na 450.0648. Calc. for $C_{17}H_{17}N_5O_6PS$—Na: 450.0642. $^1$H NMR (CH$_3$OD, 300 MHz): δ 3.88 (3H, s, OCH$_3$), 4.20-4.24 (1H, m, H-4'), 4.25-4.39 (2H, m, OCH$_2$), 5.02 (1H, d, J 5.3 Hz, H-2'), 5.51-5.57 (1H, m, H-3'), 5.76 (1H, s, H-1'), 7.12 (2H, d, J 8.6 Hz, 2×H-Ph), 7.73 (2H, d, J 8.6 Hz, 2×H-Ph), 8.21 (1H, s, H-2). $^{13}$C NMR (CH$_3$OD, 75 MHz): δ 56.0 (OCH$_3$), 68.3 (d, J 9.7 Hz, OCH$_2$), 72.8 (d, J 7.6 Hz, CH-4'), 73.2 (d. J 5.7 Hz, CH-2'), 77.7 (d, J 6. Hz, CH-3'), 94.4 (CH-1'), 115.5, 115.5, 119.7, 121.9, 132.1, 132.1, 151.7, 153.2, 153.4, 156.7, 163.2.

EXAMPLE 71

($S_p$)-8-Bromoadenosine-2'O-(tert-butyldimethylsilyl)-3',5'-cyclic N-benzyl phosphoramidate (10)

A solution of 8-bromadenosine-2'O-(tert-butyldimethylsilyl)-3',5'-cyclic phosphoric acid tributylammonium salt (2) (2.14 g, 3.0 mmol) in CH$_2$Cl$_2$ (5 ml) was added dropwise to a solution of oxalyl chloride (0.31 ml, 3.6 mmol) and DMF (0.28 ml, 3.6 mmol) in THF (15 ml) at 0° C. Benzylamine (15 mmol, 1.64 ml) was added after 30 min. and the mixture stirred for 10 min at 0° C. and for 2 h at room temperature, diluted with CHCl$_3$ (50 ml) and washed with saturated NaHCO$_3$(aq) (2×15 ml). The organic phase was dried (MgSO$_4$), the solvent distilled off and the residue purified by flash chromatography using CH$_2$Cl$_2$:MeOH 3:97 and 5:95; yield 1.28 g (67%) of a white solid. MS (electrospray): 611.2/613.2; $^{31}$P NMR (CDCl$_3$, 121 MHz): δ 8.29; $^1$H NMR (CDCl$_3$, 300 MHz): δ 0.011 (3H, s, Si-Me), 0.014 (3H, s, Si-Me), 0.82 (9H, s, Si-tBu), 4.12-4.21 (3H, m), 4.39-4.68 (3H, m), 4.97 (1H, d, J 5.1 Hz), 5.54-5.60 (1H, m), 5.88 (1H, s), 6.50 (2H, br.s, NH$_2$), 7.19-7.33 (5H, m), 8.04 (1H, s, H-2). $^{13}$C NMR (CDCl$_3$, 75 MHz): δ 5.2, –4.8, 18.0, 25.5, 45.2, 68.2 ($J_p$ 6.9 Hz), 71.2 ($J_p$ 4.2 Hz), 72.9 ($J_p$ 8.3 Hz), 76.2 ($J_p$ 3.6 Hz), 93.4, 118.3, 127.0, 127.4, 128.5, 137.3, 138.7 ($J_p$ 6.5 Hz), 149.9, 153.4, 154.6.

EXAMPLE 72

($S_p$)-8-(2-Furyl)adenosine-2'O-(tert-butyldimethylsilyl)-3',5'-cyclic N-benzyl phosphoramidate (11a)

A solution of Pd(OAc)$_2$ (60 mg, 0.27 mmol) and PPh$_3$ (142 mg, 0.54 mmol) in DMF (8 ml) under argon was stirred at 50° C. for 15 min before 2-(tri-n-butylstannyl)furane (0.63 ml, 2.0 mmol) was added. Subsequently, a solution of ($S_p$)-8-bromoadenosine-2'O-(tert-butyldimethylsilyl)-3',5'-cyclic N-benzylphosphoramidate (10) (800 mg, 1.3 mmol) in DMF (10 ml) was added. The mixture was stirred at 85° C. for 2.5 h. The solvent was distilled off and the residue purified by flash chromatography on silica gel, using CH$_2$Cl$_2$:MeOH 3:97 and 5:95; yield 636 mg (80%) of a white solid. MS (electrospray): 599.2; $^{31}$P NMR (CDCl$_3$, 121 MHz): δ 8.08; $^1$H NMR (CDCl$_3$, 300 MHz): δ 0.00 (3H, s, Si-Me), 0.04 (3H, s, Si-Me), 0.82 (9H, s, Si-tBu), 4.02-4.09 (1H, m) 4.17-4.29 (3H m), 4.41-4.65 (2H m), 5.16 (d, J 5.2 Hz), 5.79 (1H, J 1.8, 5.2 Hz,), 6.31-6.34 (3H, s+br.s,), 6.62 (1H, q, J 1.8 Hz,), 7.14 (1H, dd, J 0.6, 3.5 Hz,), 7.25-7.38 (5H, m), 7.65 (1H, dd, J 0.6, 1.8 Hz), 8.25 (1H, s, H-2); $^{13}$C NMR (CDCl$_3$, 75 MHz): δ –5.3, –4.7, 18.0, 25.5, 45.3, 68.4 ($J_p$ 7.2 Hz), 71.3 ($J_p$ 4.3 Hz), 73.1 ($J_p$ 8.5 Hz), 77.2, 94.2, 112.1, 114.1, 119.7, 127.1, 127.5, 128.6, 138.8 ($J_p$ 6.5 Hz), 141.7, 143.5, 144.8, 150.2, 153.1, 155.3.

EXAMPLE 73

($R_p$)-8-(2-Furyl)adenosine-3',5'-cyclic phosphorothioic acid ammonium salt (7a)

A 1.6 M solution of nBuLi in hexane (0.25 ml, 0.39 mmol) was added to a solution of ($S_p$)-8-(2-furyl)adenosine-2'O-(tert-butyldimethylsilyl)-3',5'-cyclic N-benzyl phosphoramidate (11a) (200 mg, 0.33 mmol) in THF (4 ml) at –78° C. The mixture was stirred for 10 min at this temperature before carbon disulfide (0.06 ml, 1.0 mmol) was added and the cooling bath removed. The mixture was stirred for 3 h at room temperature. The volume of the solvent was reduced to about 1 ml before hexane (40 ml) was added. The precipitate was collected and dissolved in dry DMF (2 ml) and ammonium fluoride (75 mg, 2.0 mmol) added. The mixture was stirred under argon at 40° C. for 48 h. The solvent was distilled off and the crude product purified by flash chromatography on silica gel using iPrOH:EtOAc:H$_2$O:NH$_3$(aq) 7:7:1:1; yield: 106 mg (74%) of a white solid. Spectroscopic data were as previously recorded.

EXAMPLE 74

S-4-(Isobutyryloxy)benzyl ($R_p$)-8-(3-furyl)adenosine-3',5'-cyclic phosphorothioate (12)

($R_p$)-8-(3-Furyl)adenosine-3',5'-cyclic phosphorothioic acid ammonium salt (7c) (0.2 mmol) was dissolved in methanol (5 ml) and triethylamine (0.3 mmol) added. Evaporation of the mixture under vacuum left the ($R_p$)-8-(3-furyl)adenosine-3',5'-cyclic phosphorothioic acid triethylammonium salt. Part of this product (70 mg, 0.16 mmol) and 4-(isobutyryloxy)benzyl iodide (73 mg, 0.24 mmol) in DMF (2 mL) was stirred at room temperature for 48 h. The solvent was evaporated off, and the residue purified by flash chromatography on silica gel using CH$_2$Cl$_2$:MeOH 3:97 and 5:95; yield: 38 mg (40%) of a white solid. MS (electrospray): 588.2; $^{31}$P NMR (CDCl$_{31}$ 81 MHz): δ 27.1; $^1$H NMR (CDCl$_3$, 200 MHz): δ 1.26 (6H, d, J 7.0 Hz), 2.75 (1H, sep, J 7.0 Hz), 4.08 (1H, s), 4.16 (1H, s), 4.34-4.50 (3H, m), 5.26 (1H, d, J 4.8 Hz), 5.67-5.74 (1H, m), 5.91 (1H, s), 6.46 (2H, br.s,), 6.80 (1H, s,), 6.98 (2H, d, J 8.5 Hz,), 7.34 (2H, d, J 8.5 Hz,), 7.92 (1H, s), 8.13 (1H s).

EXAMPLE 75

($R_p$)-8-(4-Fluorophenyl)adenosine-2'O-(tert-butyldimethylsilyl)-3',5'-cyclic N-benzylphosphoramidate 11m A mixture of Pd(OAc)$_2$ (0.037 g, 0.163 mmol) and PPh$_3$ (0.091 g, 0.348 mmol) in NMP (4 ml) was stirred at 50° C. until the solution had become dark red. A solution of 8-bromoadenosine-2'O-(tert-butyldimethylsilyl)-3',5'-cyclic-N-benzylphosphoramidate (10) (0.500 g, 0.81 mmol) in NMP (2 ml) and 1-tributylstannyl-4-fluorobenzene (0.623 g, 1.62 mmol) were added. The reaction mixture was stirred at 130-135° C. for 8 h, allowed to cool to room temperature, the NMP removed at reduced pressure and the residual material subjected to flash chromatography on silica gel using 7.5% MeOH in CH$_2$Cl$_2$. The product was a white solid material which contained traces of organotin residues which were removed by dissolution of the product in CH$_2$Cl$_2$ and reprecipitation by addition of hexane; yield 0.248 g (49%); $^1$H NMR (CH$_3$OD, 300 MHz): δ −0.17 (3H, s, CH$_3$), −0.11 (3H, s, CH$_3$), 0.62 (9H, s, C(CH$_3$)$_3$), 4.06 (2H, d, J 12.5 Hz, C$_6$H$_5$CH$_2$), 4.12-4.21 (1H, m, H-4'), 4.44-4.59 (2H, m, OCH$_2$), 5.05 (1H, d, J 5.3 Hz, H-2'), 5.63-5.70 (1H, m, H-3'), 5.71 (1H, s, H-1'), 7.15-7.33 (7H, m, 7×H-Ph), 7.71-7.76 (2H, m, 2×H-Ph), 8.21 (1H, s, H-2). $^{13}$C NMR (MeOH, 75 MHz): δ −5.2 and −4.5 (2×CH$_3$), 18.9 (Si—C), 25.9 (3×CH$_3$), 45.9 (NHCH$_2$), 69.8 (d, J 7.2 Hz, OCH$_2$), 72.5 (d, J 4.4 Hz, CH-4'), 74.2 (d. J 8.3 Hz, CH-2'), 78.1 (d, J 3.8 Hz, CH-3'), 95.6 (CH-1'), 117.1, 117.4, 120.0, 126.1, 126.1, 128.1, 128.1, 128.4, 132.9, 133.0, 140.8, 140.85, 151.5, 151.6, 154.2, 157.2, 164.0.

EXAMPLE 76

($R_p$)-8-(4-Fluorophenyl)-3',5'-cyclic phosphorothioic acid tributylammonium salt 8m 1.6 M nBuLi in hexane (0.27 ml, 0.43 mmol) was added to a solution of ($R_p$)-8-(4-fluorophenyl)adenosine-2'O-(tert-butyldimethylsilyl)-3',5'-cyclic-N-benzylphosphoramidate (11m) (0.250 g, 0.39 mmol) in THF (6 ml) at −78° C. The mixture was stirred under argon, at −78° C., for 10 min before CS$_2$ (0.08 ml, 1.24 mmol) was added. The reaction mixture was stirred at −78° C. for 20 min and at room temperature for 2 h. Most of the solvent was distilled off and hexane was added until precipitation was complete. The precipitate was dissolved in water (9 ml) and 1.2 M HCl (1.1 ml) was added at 0° C. ($R_p$)-8-(4-Fluorophenyl)-2'O-(tert-butyldimethylsilyl)-3',5'-cyclic phosphorothioic acid (6m) was precipitated. The dried thioic acid (0.150 g, 0.27 mmol) was dissolved in dry DMF (1.5 ml), ammonium fluoride (0.070 g, 1.9 mmol) added and the mixture stirred at room temperature for 5 days. The reaction mixture was filtered and tributylamine was added to the filtrate until a clear solution resulted. The volatile material was distilled off from the filtrate, the residual material extracted with hexane to remove excess tributylamine and the remaining material subjected to flash chromatography on silica gel using CH$_2$Cl$_2$:CH$_3$OH:NBu$_3$ 100:10:1. The ammonium salt, which contained tributylamine, was further purified by dissolution in CH$_2$Cl$_2$ and reprecipitation by addition of hexane; yield 0.065 g (386 from 11m) of a white solid material. $^1$HNMR (CH$_3$OD, 300 MHz): δ 0.90 (9H, t, J 7.3 Hz, 3×CH$_3$), 1.31-1.40 (6H, m, 3×CH$_2$), 1.56-1.65 (6H, m, 3–CH$_2$), 3.04-3.15 (6H, m, 3–CH$_2$), 3.87-3.92 (1H, m, H-4'), 4.04-4.32 (2H, m, OCH$_2$), 5.02 (1H, d, J 5.3 Hz, H-2'), 5.40-5.48 (1H, m, H-3'), 5.68 (1H, s, H-1'), 7.22-7.27 (2H, m, 2×H-Ph), 7.73-7.78 (2H, m, 2×H-Ph), 8.16 (1H, s, H-2). $^{13}$CNMR (MeOD, 75 MHz): δ −5.2 (CH$_3$OD) 13.9 (3×CH$_3$), 20.9 (3×CH$_2$), 26.7 (3×CH$_2$), 53.9 (3×CH$_2$), 68.2 (d, J 9.6 Hz, OCH$_2$), 72.8 (d, J 7.6 Hz, CH-4'), 73.4 (d. J 5.7 Hz, CH-2'), 78.7 (d, J 6.4 Hz, CH-3'), 94.5 (CH-1'), 116.9, 116.9, 119.8, 126.2 132.9, 132.9, 151.6, 153.3, 153.9, 156.9, 163.9.

EXAMPLE 77

($R_p$)-8-(4-Fluorophenyl)-3',5'-cyclic phosphorothioic acid sodium salt (9m)

($R_p$)-8-(4-Fluorophenyl)-3',5'-cyclic phosphorothioic acid tributylammonium salt (8m) (0.050 g, 0.11 mmol) was dissolved in 0.1 M NaOH in MeOH (1.1 ml). The sodium salt was precipitated by addition of hexane; yield 0.027 g (51%) of a white, solid material. $^1$H NMR (CH$_3$OD, 300 MHz): δ 4.20-4.41 (3H, m, H-4' and OCH$_2$), 5.08 (1H, d, J 5.4 Hz, H-2'), 5.51-5.58 (1H, m, H-3'), 5.75 (1H, s, H-1'), 7.29-7.34 (2H, m, 2×H-Ph), 7.80 7.86 (2H, m, 2×H-Ph), 8.23 (1H, s, H-2); $^{13}$CNMR (MeOD, 75MHz): δ 68.3 (d, J 9.3 Hz, OCH$_2$), 72.9 (d, J 7.8 Hz, CH-4'), 73.2 (d, J 5.6 Hz, CH-2'), 77.6 (d, J 6.5 Hz, CH-3'), 94.1 (CH-1'), 116.9, 117.2, 119.8, 126.2, 132.9, 132.9, 151.6, 153.2, 153.9, 156.9, 163.8.

EXAMPLE 78

(Sp) 8-(2-Thienyl)adenosine-2'O-(tert-butyldimethylsilyl)-3',5'-cyclic N-benzylphosphoramidate (11b)

A solution of 2-thienylzinc chloride (0.3 ml, 1 M, 0.300 mmol) in THF (2 ml) was added under argon to a solution of (S) 8-bromoadenosine-2'O-(tert-butyldimethylsilyl)-3',5'-cyclic N-benzylphosphoramidate (10) (0.122 g, 0.200 mmol) and tetrakis(triphenylphosphine)palladium (0.046 g, 0.040 mmol) in THF (2 ml). The reaction mixture was heated under gentle reflux for 3 h. An aqueous saturated solution of ammonium chloride (3 ml) and dichloromethane (10 ml) were added to the cold reaction mixture, and the organic phase extracted with saturated brine (2×3 ml), dried (MgSO$_4$) and the solvents distilled off. The residual material was subjected to flash chromatography on silica gel using MeOH:CH$_2$Cl$_2$ 1:20; yield 0.059 g (48%) 31p NMR (CDCl$_3$, 81 MHz): δ 8.3. $^1$H NMR (CDCl$_3$, 200 MHz) δ 0.11 (6H, s, CH$_3$Si), 0.88 (9H, s, (CH$_3$)$_3$C), 4.2-4.7 (5H, m, H4' H5' PhCH$_2$), 5.08 (1H, d, J 5.1 Hz, H2'), 5.28 (1H, s, NH), 5.5-5.6 (1H, m, H3'), 5.94 (1H, s, H1'), 6.53 (2H, br.s, NH$_2$), 7.09 (1H, dd, J 4.0, 5.6 Hz, H4-thienyl), 7.2-7.4 (7H, m, H—Ar), 8.10 (1H, s, H2). Subsequent reaction, e.g. thiation by carbon disulfide and a strong base and desilylation, leads to the thioic acid 7b.

EXAMPLE 79

Preparation of Capsules for Oral Administration

| | |
|---|---|
| (Rp)-8-(2-furyl)adenosine-3',5'-cyclic phosphorothioic acid ammonium salt (Example 73) | 50 mg |
| Lactose | q.s. |

The powder is mixed and filled into capsules (Capsule size O).

EXAMPLE 80

Preparation of Injection Formulation

| | |
|---|---|
| (Rp)-8-(4-fluorophenyl)-3',5'-cyclic phosphorothioic acid sodium salt (Example 77) | 25 mg |
| Sodium chloride | q.s. |
| Aqua purificata | ad. 5 ml |

An isotonic solution of (Rp)-8-(4-fluorophenyl)-3',5'-cyclic phosphorothioic acid sodium salt is prepared by dissolving this compound and sodium chloride in water. The solution is filled into a 5 ml vial and autoclaved. The product contains 5 mg (Rp)-8-(4-fluorophenyl)-3',5'-cyclic phosphorothioic acid sodium salt per ml.

EXAMPLE 81

Determination of $IC_{50}$ Values of New Rp-cAMPS Analogs in PKA Type Iα Enzyme Activation Assay In Vitro (Cook Kinase Assay)

The purpose of the following analysis was the classification of new Rp-cAMPS analogs as antagonists or agonists of Type I (RIα/Cα) holoenzyme complex of the cAMP-dependent protein kinase and the determination of the $EC_{50}$ values using a suppression or an activation assay based on the spectrophotometric assay by Cook.

Rp-cAMPS Analog Screening for Antagonists and Agonists:

First, new Rp-cAMPS analogs were screened in an activation assay using 10 nM RIα holoenzyme and 10 µM of each Rp-cAMPS analog to test for activation. To characterize in detail the antagonistic properties of the Rp-cAMPS analogs a suppression assay was used. 10 nM RIα holoenzyme was partially (80%) activated by addition of 1 µM Sp-8-Br-cAMPS (in assay mix for three minutes). Then holoenzyme was reconstituted by addition of Rp-cAMPS antagonist (increasing concentrations, five minutes incubation time before starting the assay with kemptide). Antagonists then block binding and activation of PKA by Sp-8-Br-cAMPS by competitive antagonism and result in a decrease in kinase activity.

$EC_{50}$ Determination for Rp-cAMPS Analogs Vs. PKA Type Iα:

$EC_{50}$ values for antagonists were determined using the suppression assay based on the spectrophotometric assay by Cook and different concentrations of Rp-cAMPS analogs ranging from pM to mM. At least 10 measurements in duplicates were performed per analog using partly activated RIα holoenzyme (10 nM) in 1 µM Sp-8-Br cAMPS (80% activation of the complex). Preincubations of five minutes were given before adding kemptide to allow reconstitution of the holoenzyme complex for compounds with antagonistic properties. The new compounds were compared to Rp-8-Br-cAMPS in the testing.

The activation constant of RIα holoenzyme with cAMP was determined. After a 3 minute preincubation of increasing concentrations of cAMP with 10 nM RIα holoenzyme in assay mix the reaction was started by addition of 200 µM kemptide. $OD_{340}$ was monitored for 1 minute and the slope ($8OD_{340}$/min) was plotted as a direct correlation for the relative activity of activated catalytic subunit. $EC_{50}$ was 88 nM.

The reversal of Sp-8-Br-cAMP-mediated PKA activation by Rp-8-(2-furyl)-cAMPS was studied. The half-maximal antagonistic effect ($IC_{50}$ or $EC_{50}$) of Rp-8-(2-furyl)-cAMPS was 238, 337 and 360 nM in three experiments in this test-system.

The reversal of Sp-8-Br-cAMP-mediated PKA activation by Rp-8-(2-thienyl)-cAMPS was studied. The half-maximal antagonistic effect ($IC_{50}$ or $EC_{50}$) of Rp-8-(2-thienyl)-cAMPS was 449 nM in this test-system.

The reversal of Sp-8-Br-cAMP-mediated PKA activation by Rp-8-(3-furyl)-cAMPS was studied. The half-maximal antagonistic effect ($IC_{50}$ or $EC_{50}$) of Rp-8-(3-furyl)-cAMPS was 607 nM in this test-system.

The reversal of Sp-8-Br-cAMP-mediated PKA activation by Rp-8-(3-thienyl)-cAMPS was studied. The half-maximal antagonistic effect ($IC_{50}$ or $EC_{50}$) of Rp-8-(3-thienyl)-cAMPS was 739 nM in this test-system.

The reversal of Sp-8-Br-cAMP-mediated PKA activation by Rp-8-phenyl-cAMPS was studied. The half-maximal antagonistic effect ($IC_{50}$ or $EC_{50}$) of Rp-8-phenyl-cAMPS was 1058 µM in this test-system.

The reversal of Sp-8-Br-cAMP-mediated PKA activation by Rp-8-acetyl-cAMPS was studied. The half-maximal antagonistic effect ($IC_{50}$ or $EC_{50}$) of Rp-8-acetyl-cAMPS was 1.58 µM in this test-system.

The reversal of Sp-8-Br-cAMP-mediated PKA activation by Rp-8-ethoxyvinyl-cAMPS was studied. The half-maximal antagonistic effect ($IC_{50}$ or $EC_{50}$) of Rp-8-ethoxyvinyl-cAMPS was 2.4 µM in this test-system.

The reversal of Sp-8-Br-cAMP-mediated PKA activation by Rp-8-(2-Br-5-furyl)-cAMPS was studied. The half-maximal antagonistic effect ($IC_{50}$ or $EC_{50}$) of Rp-8-(2-Br-5-furyl)-cAMPS was 2.9 µM in this test-system.

The reversal of Sp-8-Br-cAMP-mediated PKA activation by Rp-8-ethyl-cAMPS. The half-maximal antagonistic effect ($IC_{50}$ or $EC_{50}$) of Rp-8-ethyl-cAMPS-cAMPS was 6.13 µM in this test-system.

The reversal of Sp-8-Br-cAMP-mediated PKA activation by Rp-8-methyl-cAMPS was studied. The half-maximal antagonistic effect ($IC_{50}$ or $EC_{50}$) of Rp-8-Me-cAMPS was 8.76 µM in this test-system.

The reversal of Sp-8-Br-cAMP-mediated PKA activation by the previously known compound Rp-8-Br-cAMPS was studied. The half-maximal antagonistic effect ($IC_{50}$ or $EC_{50}$) of Rp-8-Br-cAMPS was 1202 nM in this test-system and 1350 nM on average in several experiments (n=3).

The reversal of Sp-8-Br-cAMP-mediated PKA activation by Rp-8-(3-pyrrol)-cAMPS was studied. The half-maximal antagonistic effect ($IC_{50}$ or $EC_{50}$) of Rp-8-(3-pyr)-cAMPS was 3.61 µM in this test-system.

The reversal of Sp-8-Br-cAMP-mediated PKA activation by Rp-8-(5-methyl-2-furyl)-cAMPS was studied. The half-maximal antagonistic effect ($IC_{50}$ or $EC_{50}$) of Rp-8-(5-Me-2-furyl)-cAMPS was 1.16 µM in this test-system.

The reversal of Sp-8-Br-cAMP-mediated PKA activation by Rp-8-benzofuryl-cAMPS was studied. The half-maximal antagonistic effect ($IC_{50}$ or $EC_{50}$) of Rp-8-Me-cAMPS was 2.78 µM in this test-system.

The reversal of Sp-8-Br-cAMP-mediated PKA activation by Rp-8-(5-hydroxymethyl-2-furyl)-cAMPS was studied. The half-maximal antagonistic effect ($IC_{50}$ or $EC_{50}$) of Rp-8-(5-MeOH-2-furyl)-cAMPS. was 1.98 µM in this test-system.

EXAMPLE 82

Determination of $IC_{50}$ Values of New Rp-cAMPS Analogs in PKA Type IIα Enzyme Activation Assay In Vitro (Cook Kinase Assay)

In order to characterize selectivity profile of antagonist compounds for the preferred drug target (PKA type Iα) versus other PKA enzymes that should preferably not be inhibited when targeting PKA type Iα for immunostimulation, $EC_{50}$ values for some selected compounds versus PKA type IIα were determined using the suppression assay based on the spectrophotometric assay by Cook.

$EC_{50}$ determination for Rp-cAMPS analogs versus PKA type IIα: At least 10 measurements in duplicates were performed per analog using partly activated RIIα holoenzyme (10 nM) in 1 µM Sp-8-Br cAMPS (75% activation of the complex). Preincubations of five minutes were given before adding kemptide to allow reconstitution of the holo complex.

The activation constant of Holo RIIα with agonist Sp-8-Br-cAMPS was determined. After a 3 minute preincubation of increasing concentrations of cAMP with 10 nM Holo RIIα in assay mix the reaction was started by addition of 200 µM kemptide. $OD_{340}$ was monitored for 1 minute and the slope ($\Delta OD_{340}$/min) was plotted as a direct correlation for the relative activity of activated catalytic subunit. $EC_{50}$ was 294 nM.

The reversal of Sp-8-Br-cAMP-mediated PKA type II activation by Rp-8-(2-furyl)-cAMPS was studied. The half-maximal antagonistic effect ($IC_{50}$ or $EC_{50}$) of Rp-8-(2-furyl)-cAMPS was 11.6 and 16.7 µM in two experiments in this test-system.

The reversal of Sp-8-Br-cAMP-mediated PKA type II activation by Rp-8-phenyl-cAMPS was studied. The half-maximal antagonistic effect ($IC_{50}$ or $EC_{50}$) of Rp-8-phenyl-cAMPS was 48.6 µM in this test-system.

The reversal of Sp-8-Br-cAMP-mediated activation of PKA type II by the previously known compound Rp-8-Br-cAMPS was studied. The half-maximal antagonistic effect ($IC_{50}$ or $EC_{50}$) of Rp-8-Br-cAMPS was 14.9 µM in this test-system.

EXAMPLE 83

Determination of $EC_{50}$ Values of New Rp-cAMPS Analogs Binding to PKA Type Iα in Competitive Ligand Binding Assay In Vitro (Biacore Assay)

The purpose of the experiment was to assess properties of cAMP analogs acting as antagonists of type I (RIα/Cα) holo enzyme complex of the cAMP dependent protein kinase in a surface binding and competition assay based on Biacore technology and determine of $EC_{50}$ values for antagonistic effects by this ligand binding method which is independent from the enzyme activity assay.

Surface Competition Assay with Antagonists of Holo RIα:

The Biacore surface competition assay was designed as an alternative method to the activity based assay by Cook. This assay allows measuring of antagonist binding independently from kinase activity in order to determine $EC_{50}$ values for cAMP analogs specifically binding to distinct cAMP-binding domains within the holo enzyme complex. Thus both assays either based on activity or binding yield complementing information about the mechanism how antagonist binding prevents the activation of the holo enzyme complex.

For these studies it was necessary to capture not only the regulatory subunit onto agonist sensor surfaces (i.e. 8-AHA cAMP), but to immobilise the whole holo enzyme complex site-directed via antagonist ligands (i.e. Rp-8AHA cAMPS). This facilitates the determination of $EC_{50}$ values for antagonists binding either to the holo enzyme complex or single sites of the regulatory subunits. The holo enzyme complex will be incubated with different amounts of antagonist prior to injection to the chip surface. Binding of antagonist results in a reduced binding signal on the chip surface (surface competition) yielding $EC_{50}$ values for the antagonists. However, if the holo complex dissociates upon binding to the ligand surface because of partial agonistic properties of the ligand, the resulting binding signal will be lower than expected and the dissociation may alter the observed $EC_{50}$ value for the antagonist. Thus various experiments had to be performed to validate whether holo RIα or only RIα is bound during association to the Rp-8-AHA cAMPS or the 8-AHA cAMP surface.

For that reason the holo RIα was tested for binding on the two different surfaces, the 8-AHA cAMP and the Rp 8AHA-cAMPS surface, using two different conditions. In the presence of ATP and Mg the regulatory and catalytic subunits bind tightly and form the holo enzyme complex, whereas in the presence of EDTA which chelates the Mg ions the affinity is significantly lower and dissociation of the complex is facilitated. During association of a 10 nM RIα holoenzyme solution a response signal of 900 RU was achieved on the Rp-8-AHA cAMPS surface. Less than half of this signal was reached on the 8-AHA cAMP surface, indicating that only the RIα subunit of the holo enzyme was bound to the 8-AHA cAMP surface or that during binding of the holo enzyme the complex was dissociated leaving only the RIα subunit bound to the chip surface. When 10 mM EDTA was added to the holo enzyme to facilitate dissociation of the complex prior to injection only 250 RU were bound on both the Rp-8-AHA cAMPS and the 8-AHA cAMP surfaces, which might be due to binding of RIα subunit alone. When an excess of antagonist (10 µM Rp-8-Br cAMPS or 10 µM Rp-8-(2-Furyl) cAMPS) was added to the holo enzyme, binding of holo complex was completely blocked at the Rp-8-AHA cAMPS surface, whereas no effect in binding to the 8-AHA cAMP surface was observed.

To determine the $EC_{50}$ values of antagonists, different concentrations of antagonists were incubated with 10 nM holo RIα and injected onto the two detection surfaces. Competitive effects of Rp-8-(2Furyl) cAMPS and Rp-8-Br cAMPS were only detectable on the Rp-8AHA cAMPS surface, whereas the binding to 8-AHA cAMP was not affected by any concentration of antagonist. The resulting $EC_{50}$'s were determined on the Rp-8-AHA cAMPS surface. With an $EC_{50}$ of 377 nM for Rp-8-(2-Furyl) cAMPS and an $EC_{50}$ of 2.9 µM for Rp-8-Br cAMPS these data are similar to those $EC_{50}$ values estimated by Cook assay in previous studies ($EC_{50}$=349 nM for Rp-8-(2-Furyl) cAMPS and $EC_{50}$=1.3 µM for Rp-8-Br CAMPS). Rp-8-(3Furyl) cAMPS was analysed in the same way and had an $EC_{50}$ of 743 nM (Cook assay 607 nM). Consequently it can be concluded that the ligand binding antagonist assay on Biacore yields comparable results to the data based on activity assays.

Competition binding assays on Rp-8-AHA cAMPS and 8-AHA cAMP surfaces with 10 nM Holo RIα, Holo RIα in 10 mM EDTA and Holo RIα in the presence of 10 µM of antagonists Rp-8-Br cAMPS or Rp-8-2-Furyl cAMPS were performed. Association and dissociation times of 5 minutes at a flow rate of 10 µl/min were recorded.

Injections of 10 nM Holo RIα with 3.9 nM-8 µM Rp-8-(2-Furyl) cAMPS and 19 nM-38.4 µM Rp-8-Br cAMPS binding to Rp-8-AHA cAMPS and 8-AHA cAMP sensor surfaces gave association and dissociation times of 5 minutes at a flow rate of 10 µl/min.

The $EC_{50}$ values of antagonist Rp-8-(2Furyl) cAMPS on the Rp-8-AHA cAMPS surface were determined; the binding signal of the Holo RIα after an association time of 5 minutes at a flow rate of 10 µl/min was plotted against the log of antagonist concentration. $EC_{50}$ was determined as 377 nM.

The $EC_{50}$ values of antagonist Rp-8-(3Furyl) cAMPS on the Rp-8-AHA cAMPS surface were determined; the binding signal of the Holo RIα after an association time of 5 minutes at a flow rate of 10 μl/min was plotted against the log of antagonist concentration. $EC_{50}$ was determined as 743 nM.

The $EC_{50}$ values of previously known antagonist Rp-8-Br-cAMPS on the Rp-8-AHA cAMPS surface were determined; the binding signal of the Holo RIα after an association time of 5 minutes at a flow rate of 10 μl/min was plotted against the log of antagonist concentration. $EC_{50}$ was determined as 2.6 μM.

Summary of Results from Biological Characterization in Vitro

Table 1 provides an overview of the data from the Cook assay for PKA type Iα enzyme activity.

TABLE 1

| Rp cAMPS analogs | Antagonist | Agonist | $EC_{50}$ inhibition | relative potency* |
|---|---|---|---|---|
| Rp-8-(2-furyl)cAMPS | yes | no | 3.19E−07 | 4.24 |
| Rp-8-(2-thienyl)cAMPS | yes | no | 4.49E−07 | 3.01 |
| Rp-8-(3-furyl)cAMPS | yes | no | 6.07E−07 | 2.23 |
| Rp-8-(3-thienyl)cAMPS | yes | no | 7.39E−07 | 1.83 |
| Rp-8-Phe cAMPS | yes | no | 1.06E−06 | 1.28 |
| Rp-8-(5-Me-2-furyl)cAMPS | yes | no | 1.16E−06 | 1.17 |
| Rp-8-Br cAMPS (3x) | yes | no | 1.35E−06 | 1.00 |
| Rp-8-Acetyl cAMPS | yes | no | 1.58E−06 | 0.86 |
| Rp-8-(5-MeOH-2-furyl)cAMPS | yes | no | 50% inhibition at 1.98E−06 | 0.68 |
| Rp-8-(1-Ethoxyvinyl)cAMPS | yes | no | 2.40E−06 | 0.56 |
| Rp-8-benzofuryl cAMPS | yes | no | 2.78E−06 | 0.49 |
| Rp-8-(2-Br-5-furyl)cAMPS | yes* | no | 50% inhibition at 3E−06 | 0.45 |
| Rp-8-(3-Pyr)cAMPS | yes | no | 3.61E−06 | 0.37 |
| Rp-8-Eth cAMPS | yes | no | 6.13E−06 | 0.22 |
| Rp-8-Me cAMPS | yes | no | 8.72E−06 | 0.16 |

*antagonists relative to Rp-8Br-cAMPS

Table 2 provides an overview of the data from the Cook assay for PKA type IIα enzyme activity compared to the activation data for PKA type Iα for selected compounds and shows the selectivity profiles.

TABLE 2

| | Holo RIIa | | | | | |
|---|---|---|---|---|---|---|
| Rp cAMPS analogs | Antagonist | relative inhibition* | Agonist | $EC_{50}$ inhibition | relative potency** | $EC_{50}$RII/ $EC_{50}$RI*** |
| Sp-8Br cAMPS | no | | yes | 4.65E−07 | | |
| Rp-8(2-furyl) cAMPS | yes | 59% | no | 1.16E−05 | 1.28 | 32 |
| Rp-8Br cAMPS | yes | 79% | no | 1.49E−05 | 1.00 | 12 |
| Rp-8-Phe cAMPS | yes | 61% | no | 4.86E−05 | 0.31 | 46 |

*% antagonist effect with 1 μM Sp-8Br-cAMPS at 250 μM of Rp-cAMPS analog
**antagonists relative to Rp-8-Br-cAMPS
***Selectivity for PKA type I ($EC_{50}$ PKA type II/$EC_{50}$ PKA type I)

Table 3 shows data from Cook assay for PKA type Iα enzyme activity in comparison with data from ligand binding competition assay (Biacore assay) with selected compounds.

TABLE 3

| antagonist | holo RIa Cook | holo RIa Biacore | holo RIIa Cook | holo RIIa Biacore |
|---|---|---|---|---|
| Rp-8(2-furyl)cAMPS | 349 nM | 377 nM* | | |
| Rp-8(3-furyl)cAMPS | 607 nM | 743 nM* | | |
| Rp-8Br cAMPS | 1.3 μM | 2.9 μM* (10 nM holo) | 14.9 μM | 10.8 μM (Rp-8-AHA surface) |
| Rp-8Br cAMPS | 1.3 μM | 2.4 μM* (2 nM holo) | 14.9 μM | 21.2 μM (8-AHA surface) |

EXAMPLE 84

Pre-Clinical Testing in Human T Cells, Ex Vivo Clinical Testing in HIV+ T Cells cAMP analogs were characterized with regard to agonist or antagonist properties, potencies and toxic effects using an assay where it was possible to evaluate the effects of the compounds on T lymphocyte proliferation. Human peripheral T lymphocytes were activated to proliferation in a polyclonal fashion by cross-linking of the CD3 surface markers. The cells were exposed to increasing concentrations of various new cAMP analogs in the absence and presence of the PKA type I agonist Sp-8-Br-cAMPS, added to mimic the elevated level of cAMP in T lymphocytes from HIV-infected individuals.

Based on the Rp configuration of their chiral phosphorus, the compounds would be expected to display antagonist properties. The compounds tested were derivatives of Rp-8-Br-cAMPS with substitutions in the 8-position of the adenine ring. This position is an electron drawing centre that provides drug target selectivity. Modifications in this position were expected to yield compounds with stronger affinity for binding site B on the R subunit of PKA type I and thus higher potency and improved selectivity.

Table 4 summarizes the properties of cAMP analog compounds tested using human primary T lymphocytes. Several modifications of the cAMP molecule have been made at various positions, but so far none has led to any improvement in potency and selectivity compared to the starting compound Rp-8-Br-cAMPS detected using T lymphocyte proliferation assays. However, some compounds (see Table 4) were shown to be more potent than the reference compound Rp-8-Br-cAMPS when tested directly on the PKA type I holoenzyme using an enzymatic assay (see Table 4).

TABLE 4

| | Ex vivo testing in T lymphocytes | | | |
|---|---|---|---|---|
| Compound | Analog number | Antagonist properties | Agonist properties | Relative potency* |
| Rp-8-Br-cAMPS | LA-1001 | Yes | No | 1.00 |
| Sp-8-Br-cAMPS | — | No | Yes | 1.00 |
| Rp-8-(2-FU)-cAMPS | LA-3026 LA-3001 | Yes | No | 0.37 |
| Rp-8-(2-Br-5-FU)-cAMPSx | LA-3027/ LA-3002 | Yes | No | 0.19 |

TABLE 4-continued

Ex vivo testing in T lymphocytes

| Compound | Analog number | Antagonist properties | Agonist properties | Relative potency* |
|---|---|---|---|---|
| Rp-8-cPA-cAMPS | LA-3028 | Yes | No | 0.04 |
| Rp-8-Phe-cAMPS | LA-3003 | Yes | No | 0.09 |
| Rp-8-EthVin-cAMPS | LA-3004 | Yes | No | 0.26 |
| Rp-8-Me-cAMPS | LA-3005 | Yes | No | 0.69 |
| Rp-8-Ac-cAMPS | LA-3006 | Yes | No | 0.43 |
| Rp-8-Eth-cAMPS | LA-3007 | Yes | No | 0.63 |
| Rp-8-(1-OHEth)-cAMPS§ | LA-3008 | | | |
| Rp-8-(3-FU)-cAMPS | LA-3009 | Yes | Not tested | 0.56 |
| Rp-8-(3-TH)-cAMPS | LA-3010 | Yes | Not tested | 0.02 |
| Rp-8-(2-TH)-cAMPS | LA-3011 | Yes | No | 0.24 |
| Rp-8-(3-Pyr)-cAMPS | LA-3012 | Yes | No | 0.11 |
| Rp-8-(5-Me-2-FU)-cAMPS | LA-4006 | Yes | No | 0.35 |
| Rp-8-benzofuryl-cAMPS | LA-4007 | Yes | No | 0.10 |
| Rp-8-(5-MeO-2-FU)-cAMPS | LA-4008 | Yes | No | 0.25 |
| Rp-8-(5-MeOH-2-FU)-cAMPS | LA-4010 | Yes | No | 0.15 |
| Rp-8-(2'N-Me-pyrolo)-cAMPS | LA-4013 | Yes | No | 0.35 |
| Rp-8-(2-thiazole)-cAMPS | LA-4014 | Weak | No | — |
| Rp-8-(3-pyridinyl)-cAMPS | LA-4015 | No | No | — |
| Rp-8-(para-MeOH-Phe)-cAMPS | LA-4016 | No | Yes | — |

EXAMPLE 85

Proof of Principle Experiments in a Mouse Retrovirus-Induced Immunodeficiency, Murine AIDS FIG. 1. Treatment of infected mice with PKA type I antagonists reduces the frequency of TNF-α secreting CD4 T cells. The frequency of TNF-α positive cells was evaluated by intracytoplasmic staining. Cells were analysed after staphylococcal enterotoxin (SEB) or in basal conditions. The effect of Rp-8-Br-cAMP on SEB stimulated secretion was significant with p=0.0012. The effect of Rp-8-Furyl was also significant at p=0.0041.

Treatment of Rp-8-Br-cAMP dramatically reduced TNF-α secretion by CD4 T cells of infected mice (FIG. 1). MAIDS was characterized by a strong increase of the frequency of CD4$^+$ T cells secreting TNF-α, either spontaneously of after stimulation with SEB. In treated mice, this frequency was reduced to near normal values. In the case of Rp-8-Br-cAMP, this could not be attributed to toxic effect since proliferative responses to anti-CD3 mAb were actually increased. Rp-8-Furyl-cAMP inhibited TNF-α secretion by CD4$^+$ T cells from the infected animals. In these experiments, Rp-8-Furyl-cAMP and Rp-8-Br-cAMP had similar effects on spontaneous and SEB-induced secretion of TNF-α by CD4$^+$ T cells (FIG. 1). Rp-8-Br-cAMP and Rp-8-(2-furyl)-cAMPS treatment modified the secretory profile of CD4$^+$ T cells from the infected mice, slightly increasing IFN-γ (botshown) and reducing TNF-α secretion after stimulation with staphylococcal enterotoxin SEB. This indicates that treatment with this class of agents could improve Th1 immune responses directed against opportunistic intracellular pathogens while helping to reduce inflammatory manifestations of the syndrome.

Experimental Details for Examples 81 to 85
Cook Coupled Enzyme Assay for PKA
Preparation of the RIα Holoenzyme Complex:

Holoenzyme formation was performed by overnight dialysis of PKA RIα and PKA Cα in a molar ratio of 1.2 to 1.0. Three 1 l buffer changes (dialysis buffer: 20 mM MOPS pH 7.0, 150 mM NaCl, 5 mM MgCl$_2$, 100 μM ATP, 5 mM β-mercaptoethanol) were carried out to remove the cAMP from the regulatory subunit.

Test of Holoenzyme Complex Formation and Assay Conditions:

Holoenzyme was diluted (dilution buffer: 100 mM MOPS pH 7.0; 10 mM MgCl$_2$, 1 mM ATP, 1 mM DTT) to a 1 μM stock solution and tested for activity in the Cook assay (assay mix: 100 mM MOPS pH 7.0, 10 mM MgCl$_2$, 1 mM phosphoenol pyruvate, 1 mM ATP, 200 μM NADH, 1 mM DTT, 15 U/ml lactate dehydrogenase, 70 U/ml pyruvate kinase). Reaction was started by mixing 1 μl 25 mM kemptide (200 μM final concentration of active peptide) to 1 μl holoenzyme (10 nM final concentration) in 100 μl total volume of assay mix. OD$_{340}$ was monitored for 1 minute and relative activity of Cα was plotted as slope of OD-decay/minute. Only a small residual activity of Cα (<8% of activated complex) showed a nearly complete formation of inactive holo enzyme complex.

Determination of the activation constant of cAMP was performed by increasing concentrations of cAMP in a 3 minute preincubation with 10 nM Holo enzyme in assay mix (EC$_{50}$=88 nM).

Preparation of the RIIα Holo Complex:

Holo enzyme formation was performed by over night dialysis of PKA RIIα and PKA Cα in a molar ratio of 1.2 to 1.0. Although the formation of holo RIIα does not require ATP/Mg, the same dialysis buffer as for holo RIα formation (20 mM MOPS pH 7.0, 150 mM NaCl, 100 μM ATP, 1 mM MgCl$_2$) was used again, because ATP is required in the assay by Cook and this buffer mimics the in vivo conditions. Complete holo formation and holo activation by 1 μM cAMP was checked before and after the titration experiments. Even after four weeks on ice holo RIIα showed the same residual activity of PKA Ca of 21% and could be fully activated by cAMP as freshly prepared.

Preparation of Rp-cAMPS Stock Solutions:

All Rp-cAMPS analogs were dissolved in dilution buffer with 20% DMSO to a final concentration of 10 mM and the concentrations were determined spectrophotometrically using molar extinctions coefficients at λ$_{max}$. Further dilutions of the Rp-cAMPS analogs were prepared by repeated 1:10 fold dilutions in dilution buffer. Preferably 1 μl but not more than 5 μl of Rp-cAMPS analog was added to the assay-mix. Therefore the DMSO concentration in the final assay mix was not higher than 1%. The effect of DMSO on the assay enzymes was tested and the results showed that DMSO concentrations of 1% or more had no effect on the assay enzymes (ADP columns) and Holo RIα (Cα, Holo RIα and cAMP activated Holo RIα columns).

In Vitro Competitive Ligand Binding Assay for cAMP Antagonists (Biacore Assay)
Preparation of the RIα and RIIα Holo Complexes:

Holo enzyme formation was performed by over night dialysis of PKA RIα or RIIα and PKA Cα in a molar ratio of 1.2 to 1.0. Three 1 l buffer changes (dialysis buffer: 20 mM MOPS pH 7.0, 150 mM NaCl, 5 mM MgCl$_2$, 100 μM ATP, 5 mM β-mercapto-ethanol) were carried out to remove the cAMP from the regulatory subunit. Both holo enzyme complexes were used and tested in previous studies.

Preparation of the Rp-8-AHA cAMPS and 8-AHA cAMP Surfaces:

Both nucleotides were dissolved in 100 mM borate buffer pH 8.5 to a concentration of 3 mM and coupled covalently to a CM5 sensor chip by standard amino coupling using EDC/NHS. An untreated CM dextran surface was used as the blank surface.

Experimental Conditions for the Surface Competition Assay:

| Instrument: | Biacore 2000, Biacore AB, Uppsala, Sweden |
|---|---|
| Temperature: | 25° C. |
| CM5 Chip (01.12.03): | FC1: CM dextran (Reference) |
| | FC2: 3 mM Rp-8-AHA cAMPS |
| | FC3: CM dextran |
| | FC4: 3 mM 8-AHA cAMP |
| Surfaces: | FC1-FC2-FC3-FC4, serial flow |
| Reference: | FC1 |

Running Buffer 1: 20 mM MOPS pH 7.4, 150 mM NaCl, 100 µM ATP, 5 mM $MgCl_2$, 0.005% Tween 20, filtered and degassed Running Buffer 2: 20 mM MOPS pH 7.4, 150 mM NaCl, 0.005% Tween 20, filtered and degassed Assay conditions: 10 or 2 nN of holo complex was injected for 5 minutes using the kinject command with a dissociation time of 5 minutes. For holo RIα running buffer 1 and for holo RIIα running buffer 2 was used. Ten to fourteen different concentrations of PKA agonists or antagonists in an appropriate range were used to determine the $EC_{50}$ values of these cAMP analogs. Therefore the binding signal on both the Rp-8-AHA cAMPS and the 8-AHA cAMP surface after 5 minutes of association time was plotted against the log of compound concentration.

| Injection volume: | 50 ul |
|---|---|
| Flow rate: | 10 ul/min |
| Regeneration: | 0.1% SDS, 3 M guanidinium hydrochloride |

Pre-Clinical Testing in Human T Cells, Ex Vivo Clinical Testing in HIV+ T Cells.

Negative Selection of Peripheral Blood Cd3+ T Cells:

Human peripheral blood mononuclear cells (PBMC) were routinely isolated from buffycoat through density gradient centrifugation with lymphoprep solution. The majority of the thrombocytes isolated together with the PBMC were removed through washing in PBS. Isolation of T lymphocytes from PBMC was based on removal of monocytes with the CD14 surface marker and B lymphocytes with the CD19 surface marker using monodisperse magnetic beads coated with antibodies against the respective cell specific markers.

Ten mL buffycoat and 25 mL PBS were added to each 50 mL tube and mixed. Ten mL lymphoprep solution was layered at the bottom of the tubes and they were centrifuged at 800×g for 25 min at 4° C. with minimum brake. The layer of PBMC was isolated and washed twice in PBS (centrifugation at 300×g for 7 min at 4° C.). The pellet was suspended in RPMI 1640/10% FCS/PS, and the number of PBMC was counted. Dynabeads CD14 and CD19 were washed six times in RPMI 1640/10% FCS/PS using a MPC, then mixed with PBMC ($3 \times 10^7$ cells/mL) at a bead to cell ratio of 5:1 (PBMC were estimated to contain 20% monocytes and 20% B lymphocytes) and placed on a rocking platform at 4° C. After 45 min the positively selected cells (monocytes and B lymphocytes) were removed from the cell mixture using a MPC, leaving a suspension of T lymphocytes. The number of T lymphocytes was counted, and the cells were used in experiments or cultured in a suspension of $1-2 \times 10^6$ cells per mL RPMI 1640/10% FCS/PS at 37° C. and 5% $CO_2$.

Proliferation Assays:

Proliferation assays were carried out to study the potency of various cAMP analogs as inhibitors or enhancers of proliferation of T lymphocytes. Hundred thousand negatively selected T lymphocytes were incubated in a total volume of 100 µL RPMI 1640/10% FCS/PS in each well of flat-bottom, 96-well microtiter plates. Activation of the cells was achieved by addition of anti-CD3 antibodies at a final dilution of $1:10^4$ (50 ng/mL) and subsequent cross-linking of the TCR/CD3 complex by addition of magnetic beads coated with Sheep anti-Mouse IgG at a bead to cell ratio of 1:1. The beads were washed six times in RPMI 1640/10% FCS/PS using a MPC prior to addition to the cell suspension. The cells were incubated for 65 h at 37° C. and 5% $CO_2$ and proliferation was examined by adding 5 µCi [methyl-$^3$H]thymidine after 48 h of this period. The cells were harvested onto filter-plates using a multisample harvester, and the filter-plates were dried in a heat incubator at 50° C. for 2 h. 20 µL scintillation liquid was added to each well and proliferation was subsequently measured by β-scintillation counting. All analyses were done in triplicates.

Treatment of Activated T Lymphocytes with cAMP Analogs:

T lymphocytes were treated with increasing concentrations of various cAMP analogs, added 30 min prior to activation of the cells by the addition of anti-CD3 antibodies to allow diffusion of the compounds into the cells. The potency of each analog to inhibit or stimulate cell proliferation was determined by measuring [methyl-$^3$H]thymidine incorporation as a function of cAMP analog concentration.

Proof of Principle Experiments in a Mouse Retrovirus-Induced Immunodeficiency, Murine AIDS Animals:

C57BL6 mice were infected with a viral preparation containing the defective virus responsible for MAIDS (titrated with the XC plaque assay and containing $10^3$ PFU ecotropic virus) and treated by the different pharmacological agents around week 10 post-infection.

Treatments:

The different compounds were administrated during 10 days by iterative IP injections or insertion of osmotic pumps. The following agents were tested:
 Rp-8-Br-cAMP: 1 mg/day/mouse
 Rp-8-Furyl-cAMP: two dosages were tested 1 mg/day/mouse and 2.5 mg/day/mouse
 Rofecoxib: 60 µg/day/mouse Infected mice received intralipid or PBS injections as shams for rofecoxib or Rp-Br/Furyl-cAMP respectively. Usually, each experimental group contained 6 to 9 animals. When the cells were cultured after the sacrifice of the animal, the different agents were added to the culture medium.

Proliferation and Cytokine Assays:

After the sacrifice of the animals, the cells were cultured for 72 hours in the presence of anti-CD3 mAb (2C11: 4 µg/ml). Tritiated thymidine was added at the end of the culture and radioactivity was measured on a scintillation analyzer.

In addition to the proliferation assay performed on lymph nodes lymphocytes in response to the anti-CD3 Ab, we mea-

EXAMPLE 86

(Sp) 8-(2-Thienyl)adenosine-2'O-(tert-butyldimethylsilyl)-3',5'-cyclic N-benzylphosphoramidate (11b A solution of 2-thienylzink chloride (0.3 ml, 1 M, 0.300 mmol) in THF (2 ml) was added under argon to a solution of (S) 8-bromoadenosine-2'O-(tert-butyldimethylsilyl)-3',5'-cyclic N-benzylphosphoramidate (0.122 g, 0.200 mmol) and tetrakis(triphenylphosphine)palladium (0.046 g, 0.040 mmol) in THF (2 ml). The reaction mixture was heated under gentle reflux for 3 h. An aqueous saturated solution of ammonium chloride (3 ml) and dichloromethane (10 ml) were added to the cold reaction mixture, and the organic phase extracted with saturated brine (2×3 ml), dried ($MgSO_4$) and the solvents distilled off. The residual material was subjected to flash chromatography on silica gel using $MeOH:CH_2Cl_2$ 1:20; yield 0.059 g (48%) $^{31}P$ NMR ($CDCl_3$, 81 MHz): δ 8.3. $^1H$ NMR ($CDCl_3$, 200 MHz) δ 0.11 (s, 6H, $CH_3Si$), 0.88 (s, 9H, $(CH_3)_3C$), 4.2-4.7 (m, 5H, H4' H5' $PhCH_2$), 5.08 (d, J 5.1 Hz, 1H, H2'), 5.28 (s, 1H, NH), 5.5-5.6 (m, 1H, H3'), 5.94 (s, 1H, H1'), 6.53 (bs, 2H, $NH_2$), 7.09 (dd, J 4.0, 5.6 Hz, 1H, H4-thienyl), 7.2-7.4 (m, 7H, H—Ar), 8.10 (s, 1H, H2).

The invention claimed is:

1. An 8-carbyl substituted cAMPS compound.
2. The compound as claimed in claim 1, wherein the 8-substituent contains up to 25 non-hydrogen atoms.
3. The compound as claimed in claim 1, wherein the 8-substituent comprises a cyclic group containing 5 to 10 ring atoms.
4. The compound as claimed in claim 1, wherein the 8-substituent is selected from the group consisting of an optionally substituted aryl group and heteroaryl group.
5. The compound of claim 4, wherein said aryl group is benzene, naphthalene, an annulated carboxylic system or an annulated heterocylic system.
6. The compound of claim 5, wherein said annulated heterocyclic system is selected from the group consisting of a pyridine, di-azine, triazine, furan, thiophene, pyrrole, azole, triazole, oxa-diazole, thiadiazole and tetrazole.
7. The compound of claim 4, wherein said heteroaryl group is selected from the group consisting of the six-membered ring azines, pyridine, diazine and triazine.
8. The compound as claimed in claim 1, wherein the 8-substituent comprises a phenyl, furyl or thienyl group.
9. The compound as claimed in claim 1, wherein the compound is protected at one or more members selected from the group consisting of a phosphorothioic sulphur, an adenosine amine group and a furyl hydroxyl group.
10. The compound as claimed in claim 1, wherein the compound is at least 90% mole in the Rp form or at least 90% in the Sp form.
11. A process for the preparation of an 8-carbylated cAMPS or derivative thereof, said process comprising at least one of the following steps:
    a) reacting a 2'-protected 8-carbylated-adenosine 3',5'-cyclic phosphoramidate with carbon disulphide and deprotecting the 2'-hydroxyl;
    b) reacting an 8-carbylated-adenosine with $SPCl_3$ in a dry solvent;
    c) reacting an 8-carbylated-adenosine with a phosphite and subsequently with sulphur;
    d) reacting an optionally 2'-protected-δ-halo-cAMPS with an alkylating agent, and wherein when the 2' hydroxyl is protected, thereafter deprotecting the 2' hydroxyl;
    e) transforming an 8-carbylated cAMPS into a salt thereof;
    f) reacting an 8-carbylated cAMPS with a biologically cleavable protecting group; and
    g) separating $R_p$ and $S_p$ isomers of an $R_p/S_p$ isomer mixture of an 8-carbylated cAMPS.
12. An 8-carbylated adenosine cyclic 3',5'-phosphoramidate.
13. An 8-carbylated-2'-protected adenosine cyclic 3',5'-phosphorothioate.
14. The 8-carbylated-2'-protected adenosine cyclic 3',5'-phosphorothioate as claimed in claim 13, wherein such is 2'-protected with a silyl group.
15. An 8-halo adenosine cyclic 3',5'-phosphoramidate, optionally 2'-protected, wherein the phosphoramidate amino group comprises a hydrogen atom.
16. The 8-halo adenosine cyclic 3',5'-phosphoramidate as claimed in claim 15, wherein such is 2'-protected with a silyl group.
17. A pharmaceutical composition comprising an 8-carbylated cAMPS together with a physiologically tolerable carrier or recipient.
18. A method of treatment of the animal to achieve a cAMP agonist or antagonist effect therein, said method comprising administering to said animal body an effective amount of an 8-carbylated cAMPS according to claim 1.
19. The method of treatment of claim 18, wherein said animal is a mammal.
20. The method of treatment of claim 19, wherein said mammal is a human.
21. An assay method for determining cAMP in a sample, which method comprises contacting said sample with a cAMP-analog and a cAMP binding reagent, wherein said analog is an 8-carbylated cAMPS.
22. The assay method of claim 21, wherein said sample is a biological sample.

* * * * *